(12) United States Patent
Frechette et al.

(10) Patent No.: US 8,030,344 B2
(45) Date of Patent: Oct. 4, 2011

(54) INHIBITORS OF HISTONE DEACETYLASE

(75) Inventors: Sylvie Frechette, Verdun (CA); Lubo Isakovic, Beaconsfield (CA); Isabelle Paquin, LaSalle (CA); Simon Roy, Montreal (CA); Oscar Moradei, Kirkland (CA); Arkadii Vaisburg, Kirkland (CA)

(73) Assignee: MethylGene Inc., Montreal (CA)

( * ) Notice: Subject to any disclaimer, the term of this patent is extended or adjusted under 35 U.S.C. 154(b) by 226 days.

(21) Appl. No.: 12/043,450

(22) Filed: Mar. 6, 2008

(65) Prior Publication Data

US 2008/0227826 A1    Sep. 18, 2008

Related U.S. Application Data

(60) Provisional application No. 60/906,733, filed on Mar. 13, 2007.

(51) Int. Cl.
*A61K 31/40* (2006.01)
*C07D 207/00* (2006.01)

(52) U.S. Cl. ........................ 514/428; 548/566
(58) Field of Classification Search .................. 514/428; 548/566
See application file for complete search history.

(56) References Cited

U.S. PATENT DOCUMENTS

| | | | |
|---|---|---|---|
| 2,754,286 A | 7/1956 | Martin | |
| 3,208,990 A | 9/1965 | Benz et al. | |
| 3,263,924 A | 8/1966 | Kolze | |
| 4,994,479 A | 2/1991 | Mase et al. | |
| 5,332,750 A | 7/1994 | Mederski et al. | |
| 5,366,878 A | 11/1994 | Pederson | |
| 5,635,377 A | 6/1997 | Pederson | |
| 5,652,355 A | 7/1997 | Metelev et al. | |
| 6,034,251 A | 3/2000 | Aslanian et al. | |
| 6,174,905 B1 | 1/2001 | Suzuki et al. | |
| 6,180,844 B1 | 1/2001 | Fujita et al. | |
| 6,541,661 B2 | 4/2003 | Delorme et al. | |
| 6,653,309 B1 | 11/2003 | Saunders et al. | |
| 7,253,204 B2 | 8/2007 | Delorme et al. | |
| 7,595,343 B2 | 9/2009 | Delorme et al. | |
| 2004/0087798 A1 | 5/2004 | Yamada | |
| 2004/0147569 A1 | 7/2004 | Suzuki et al. | |
| 2004/0186148 A1 | 9/2004 | Shankar et al. | |
| 2005/0096222 A1 | 5/2005 | Hidaka et al. | |
| 2005/0222410 A1* | 10/2005 | Stokes et al. ................ | 544/124 |
| 2005/0288282 A1 | 12/2005 | Delorme et al. | |
| 2006/0058298 A1 | 3/2006 | Delorme et al. | |
| 2006/0063210 A1 | 3/2006 | Li et al. | |
| 2007/0173527 A1 | 7/2007 | Bressi et al. | |
| 2007/0213330 A1 | 9/2007 | Delorme et al. | |
| 2008/0132503 A1 | 6/2008 | Moradei et al. | |

FOREIGN PATENT DOCUMENTS

| | | |
|---|---|---|
| CA | 2480356 A1 | 10/2003 |
| CA | 2484065 A1 | 11/2003 |
| CA | 2615105 | 1/2007 |
| EP | 0847992 A1 | 6/1998 |
| JP | 96/258863 A | 9/1996 |
| JP | 11-269146 | 10/1999 |
| JP | 11-302173 A1 | 11/1999 |
| JP | 2000-256194 | 9/2000 |
| JP | 2001131130 | 5/2001 |
| JP | 2002-332267 | 11/2002 |
| WO | 00/71703 | 11/2000 |
| WO | WO 01/38322 A1 | 5/2001 |
| WO | 01/70675 | 9/2001 |
| WO | WO 02/069947 | 9/2002 |
| WO | WO 03/024448 A2 | 3/2003 |
| WO | WO 03/075929 A1 | 9/2003 |
| WO | WO 03/076395 A1 | 9/2003 |
| WO | WO 03/076400 A1 | 9/2003 |
| WO | WO 03/076401 A1 | 9/2003 |
| WO | WO 03/076421 A1 | 9/2003 |
| WO | WO 03/076422 A1 | 9/2003 |
| WO | WO 03/076438 A1 | 9/2003 |
| WO | 03/087057 | 10/2003 |
| WO | WO 03/092686 A1 | 11/2003 |
| WO | 2004005513 | 1/2004 |
| WO | 2004/035525 | 4/2004 |
| WO | 2004/069823 | 8/2004 |
| WO | WO 2005/030705 A1 | 4/2005 |
| WO | 2005/092899 | 10/2005 |
| WO | WO 2006/122319 A | 11/2006 |
| WO | 2007/118137 | 10/2007 |

OTHER PUBLICATIONS

Zhou et al., (2001) "Cloning and Characterization of a Histone Deacetylaes, HDAC9", Proc. Natl. Acad. Sci. U.S.A., 98:10572-10577. Pon, R.T. (1993) "Solid-Phase Supports for Oligonucleotide Synthesis" Methods in Molec. Biol. 20: 465-496.
Csordas, "On the biological Role of histone Acetylation", Biochem. J., 265: 23-38 (1990).
Taunton et al., "A Mammalian Histone Deacetylase Related to the Yeast Transcriptional Regulator Rpd3p", Science, 272:408-411 (1996).
Grozinger et al., "Three Proteins Define a Class of Human Histone Deacetylases Related to Yeast Hda1p", Proc. Natl. Acad. Sci. USA, 96:4868-4873 (1999).
Kao et al., (2000) "Isolation of a Novel Histone Deacetylase Reveals that Class I and Class II Deacetylases Promote SMRT-Mediated Repression", Gene & Development 14:55-66.

(Continued)

*Primary Examiner* — Rei-tsang Shiao
(74) *Attorney, Agent, or Firm* — McDonnell Boehnen Hulbert & Berghoff LLP

(57) ABSTRACT

The invention relates to the inhibition of histone deacetylase. The invention provides compounds and methods for inhibiting histone deacetylase enzymatic activity. The invention also provides compositions and methods for treating cell proliferative diseases and conditions. One aspect of the invention provides compounds of formula (1):

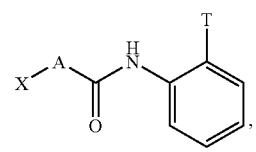

in which T, A and X are as described herein.

17 Claims, No Drawings

OTHER PUBLICATIONS

Hu, et al. (2000) "Cloning and Characterization of a Novel Human class I Histone Deacetylase that Functions as a Transcription Factor" J. Bio. Chem. 275:15254-15264.

Kao et al., (2002) "Isolation and Characterization of Mammalian HDAC10, a Novel Histone Deacetylase", J. Biol. Chem., 277:187-193.

Gao et al, (2002) "Cloning and Functional Characterization of HDAC11, a Novel Member of the Human Histone Deacetylase Family" J. Biol. Chem. 277(28): 25748-25755.

Shore, (2000) "The Sir2 Protein Family: A Novel Deacetylase for Gene Silencing and More" Proc. Natl. Acad. Sci. U.S.A., 97:14030-14032.

Cress et al., (2000) "Histone Deacetylases, Transcriptional Control, and Cancer" J. Cell. Phys., 184:1-16.

Ng et al., (2000) "Histone Deacetylases: Silencers for Hire" TIBS, 25(March):121-126.

Magnaghi Jaulin et al., (2000) "Histone Acetylation and the Control of the Cell Cycle" Prog. Cell Cycle Res., 4:41-47.

Richon et al., (1998) "A Class of Hybrid Polar Inducers of Transformed Cell Differentiation Inhibits Histone Deacetylases" Proc. Natl. Acad. Sci. USA, 95:3003-3007.

Yoshida et al., (1990) "Potent and Specific Inhibition of Mammalian Histone Deacetylase Both in Vivo and in Vitro by Trichostatin A" J. Biol. Chem., 265:17174-17179.

Yoshida et al., (1988) "Reversible Arrest of Proliferation of Rat 3Y1 Fibroblasts in Both the G1 adn G2 Phases by Trichostatin A" Exp. Cell Res., 177:122-131.

Finnin et al., (1999) "Structures of a Histone Deacetylase Homolgue Bound to the TSA and SAHA Inhibitors" Nature, 401:188 193.

Kijima et al., (1993) "Trapoxin, an Antitumor Cyclic Tetrapeptide, is an Irreversible Inhibitor of Mammalian Histone Deacetylase" J. Biol. Chem., 268(30):22429-22435.

Kwon et al., (1998) "Depudecin induces Morphological Reversion of Transformed Fibroblasts via the Inhibition of Histone Deacetylase" Proc. Natl. Acad. Sci. USA 95(7):3356-3361.

Ramchandani et al. (1997) "Inhibition of Tumorigenesis by a Cytosine-DNA, Methyltransferase, Antisense Oligodeoxynucleotide" Proc. Natl. Acad. Sci. USA 94:684-689.

Seto, et al. (1993) "Molecular Self-Assembly Through Hydrogen Bonding: Aggregation of Five Molecules to Form a Discrete Supramolecular Structure", J. Amer. Chem. Soc., 115: 1321-1329.

Harris et al. (1999) "Sequential N-Arylation of Primary Amines as a Route to Alkyldiarylamines" J.Org.Chem., 64: 6019-6022.

Perry et al., Abstract (1992) J Org Chem., 57:2883-2887.

Miletin et al., Abstract (2001) Molecules, 6:603-613.

Beer et al., Abstract (1996) J. Chem Soc., Dalton Trans., vol. 11, pp. 2341-2346.

* cited by examiner

INHIBITORS OF HISTONE DEACETYLASE

This application claims the benefit of U.S. Provisional Application Ser. No. 60/906,733, filed Mar. 13, 2007.

BACKGROUND OF THE INVENTION

1. Field of the Invention

The present invention relates generally to inhibitors of histone deacetylase. The present invention relates more specifically to N-(2-amino- and hydroxyphenyl)amide compounds and pharmaceutical compositions thereof, and their use in the inhibition of histone deacetylase.

2. Technical Background

In eukaryotic cells, nuclear DNA associates with histones to form a compact complex called chromatin. The histones constitute a family of basic proteins which are generally highly conserved across eukaryotic species. The core histones, termed H2A, H2B, H3, and H4, associate to form a protein core. DNA winds around this protein core, with the basic amino acids of the histones interacting with the negatively charged phosphate groups of the DNA. Approximately 146 base pairs of DNA wrap around a histone core to make up a nucleosome particle, the repeating structural motif of chromatin.

Csordas, Biochem. J., 265: 23-38 (1990) teaches that histones are subject to post-translational acetylation of the ε-amino groups of N-terminal lysine residues, a reaction that is catalyzed by histone acetyl transferase (HAT1). Acetylation neutralizes the positive charge of the lysine side chain, and is thought to impact chromatin structure. Indeed, Taunton et al., Science, 272:408-411 (1996), teaches that access of transcription factors to chromatin templates is enhanced by histone hyperacetylation. Taunton et al. further teach that an enrichment in underacetylated histone H4 has been found in transcriptionally silent regions of the genome.

Histone acetylation is a reversible modification, with deacetylation being catalyzed by a family of enzymes termed histone deacetylases (HDACs). The molecular cloning of gene sequences encoding proteins with HDAC activity has established the existence of a set of discrete HDAC enzyme isoforms. Grozinger et al., Proc. Natl. Acad. Sci. USA, 96:4868-4873 (1999), teaches that HDACs may be divided into two classes, the first represented by yeast Rpd3-like proteins, and the second represented by yeast Hd1-like proteins. Grozinger et al. also teaches that the human HDAC-1, HDAC-2, and HDAC-3 proteins are members of the first class of HDACs, and discloses new proteins, named HDAC-4, HDAC-5, and HDAC-6, which are members of the second class of HDACs. Kao et al., Gene & Development 14:55-66 (2000), discloses an additional member of this second class, called HDAC-7. More recently, Hu, E. et al. J. Bio. Chem. 275:15254-13264 (2000) discloses the newest member of the first class of histone deacetylases, HDAC-8. Zhou et al., Proc. Natl. Acad. Sci. U.S.A., 98:10572-10577 (2001) teaches the cloning and characterization of a new histone deacetylase, HDAC-9. Kao et al., J. Biol. Chem., 277:187-93 (2002) teaches the isolation and characterization of mammalian HDAC-10, a novel histone deacetylase. Gao et al, J. Biol. Chem. 277(28): 25748-55 (2002) teaches the cloning and functional characterization of HDAC-11, a novel member of the human histone deacetylase family. Shore, Proc. Natl. Acad. Sci. U.S.A., 97:14030-2 (2000) discloses another class of deacetylase activity, the Sir2 protein family. It has been unclear what roles these individual HDAC enzymes play.

Studies utilizing known HDAC inhibitors have established a link between acetylation and gene expression. Taunton et al., Science, 272:408-411 (1996), discloses a human HDAC that is related to a yeast transcriptional regulator. Cress et al., J. Cell. Phys., 184:1-16 (2000), discloses that, in the context of human cancer, the role of HDAC is as a corepressor of transcription. Ng et al., TIBS, 25(March):121-26 (2000), discloses HDAC as a pervasive feature of transcriptional repressor systems. Magnaghi-Jaulin et al., Prog. Cell Cycle Res., 4:41-47 (2000), discloses HDAC as a transcriptional co-regulator important for cell cycle progression.

Richon et al., Proc. Natl. Acad. Sci. USA, 95:3003-3007 (1998), discloses that HDAC activity is inhibited by trichostatin A (TSA), a natural product isolated from Streptomyces hygroscopicus, which has been shown to inhibit histone deacetylase activity and arrest cell cycle progression in cells in the G1 and G2 phases (Yoshida et al., J. Biol. Chem., 265:17174-17179 (1990); Yoshida et al., Exp. Cell Res., 177: 122-131 (1988), and by a synthetic compound, suberoylanilide hydroxamic acid (SAHA). Yoshida and Beppu, Exper. Cell Res., 177:122-131 (1988), teaches that TSA causes arrest of rat fibroblasts at the $G_1$ and $G_2$ phases of the cell cycle, implicating HDAC in cell cycle regulation. Indeed, Finnin et al., Nature, 401:188-193 (1999), teaches that TSA and SAHA inhibit cell growth, induce terminal differentiation, and prevent the formation of tumors in mice. Suzuki et al., U.S. Pat. No. 6,174,905, EP 0847992, and JP 258863/96, disclose benzamide derivatives that induce cell differentiation and inhibit HDAC. WO 03/087057, WO 03/092686, WO 03/024448, WO 2004/069823, WO 00/71703, WO 01/38322, WO 01/70675, WO 2004/035525, WO 2005/030705, and WO 2005/092899, among others, disclose additional compounds that serve as HDAC inhibitors. Other inhibitors of histone deacetylase activity, including trapoxin, depudecin, FR901228 (Fujisawa Pharmaceuticals), and butyrate, have been found to similarly inhibit cell cycle progression in cells (Taunton et al., Science 272:408-411, (1996); Kijima et al., J. Biol. Chem., 268(30):22429-22435 (1993); Kwon et al., Proc. Natl. Acad. Sci. USA 95(7):3356-61 (1998)).

These findings suggest that inhibition of HDAC activity represents a novel approach for intervening in cell cycle regulation and that HDAC inhibitors have great therapeutic potential in the treatment of cell proliferative diseases or conditions. There is therefore a need to identify additional HDAC inhibitors and to identify the structural features required for potent HDAC inhibitory activity.

BRIEF SUMMARY OF THE INVENTION

One aspect of the invention relates to a compound of formula (1):

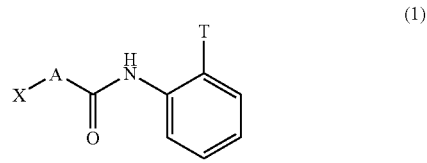

or an N-oxide, hydrate, solvate, pharmaceutically acceptable salt, complex or prodrug thereof, as well as a racemic or scalemic mixture, diastereomer, enantiomer or tautomer thereof, wherein T is $NH_2$ or OH;

A is selected from the group consisting of arylene, heteroarylene, cycloalkylene and heterocyclylene, each of which is optionally substituted; and X is
(a)

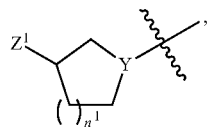

wherein
Y=N or CH,
$n^1$=0-4 and
$Z^1$ is selected from the group consisting of $R^9$—, $R^{13}$—C(O)—, $R^{13}$—C(S)—, $R^7$—N($R^2$)—, $R^6$—O—, $R^{10}$—S—, $R^{13}$—S(O)$_{1-2}$, $R^5$—C(O)—O—, $R^{15}$—O—C(O)—, $R^{15}$—C(O)—S—, $R^{15}$—S—C(O)—, $R^{11}$—C(O)—N($R^2$)—, $R^3$—N($R^2$)—C(O)—, $R^{15}$—C(S)—O—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^5$—O—C(O)—O—, $R^{15}$—O—C(O)—S—, $R^{15}$—S—C(O)—O—, $R^2$—O—C(O)—N($R^2$)—, $R^8$—N($R^2$)—C(O)—O—, $R^5$—O—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^5$—N($R^2$)—C(O)—N($R^2$)—, $R^5$—N($R^2$)—C(S)—N($R^2$)—, $R^{15}$—N($R^2$)C(S)—S—, $R^{15}$—S—C(S)—N($R^2$)—, $R^5$—NH—C(N($R^2$))—NH—, $R^5$—S(O)$_{0-2}$—N($R^2$)—, $R^5$—N($R^2$)—S(O)$_{0-2}$— and $R^{15}$—N($R^2$)—S(O)$_{0-2}$—N($R^2$)—;
with the proviso that if $n^1$ is 1 or 2 and $Z^1$ is $R^9$—, $R^{13}$—C(O)—, $R^7$—N($R^2$)—, $R^6$—O—, $R^{10}$—S—, $R^{13}$—S(O)$_{1-2}$—, $R^{15}$—C(O)—O—, $R^{15}$—C(O)—, $R^{11}$—C(O)—N($R^2$)—, $R^{13}$—N($R^2$)—C(O)—, $R^{12}$—O—C(O)—N($R^2$)—, $R^8$—N($R^2$)—C(O)—O—, $R^5$—S(O)$_2$—N($R^2$)— or $R^5$—N($R^2$)—S(O)$_2$—, then A is not thienyl, thiadiazolyl, thiazolyl, pyrimidyl, pyrazinyl, pyridazinyl, pyridyl, triazinyl or tetrazinyl;
(b)

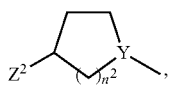

wherein
Y=N or CH,
$n^2$=0 or 2-4 and
$Z^2$ is selected from the group consisting of $R^{15}$—, $R^{15}$—C(O)—, $R^{15}$—C(S)—, $R^{15}$—N($R^2$)—, $R^{15}$—O—, $R^{15}$—S—, $R^{15}$—S(O)$_{1-2}$—, $R^{15}$—C(O)—O—, $R^{15}$—O—C(O)—, $R^{15}$—C(O)—S—, $R^{15}$—S—C(O)—, $R^{15}$—C(O)—N($R^2$)—, $R^{15}$—N($R^2$)—C(O), $R^{15}$—C(S)—O—, $R^{15}$—O—C(S)—, $R^{15}$—C(S)—S—, $R^{15}$—S—C(S)—, $R^{15}$—C(S)—N($R^2$)—, $R^5$—N($R^2$)—C(S)—, $R^{15}$—C(O)—O—, $R^{15}$—O—C(O)—S—, $R^{15}$—S—C(O)—O—, $R^5$—O—C(O)—N($R^2$)—, $R^{15}$—N($R^2$)—C(O)—O—, $R^{15}$—O—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—S—C(O)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0-2}$—N($R^2$)—, $R^{15}$—N($R^2$)—S(O)$_{0-2}$— and $R^{15}$—N($R^2$)—S(O)$_{0-2}$—N($R^2$)—;
with the proviso that if $n^2$ is 2 and $Z^2$ is $R^{15}$—, $R^{15}$—C(O)—, $R^{15}$—N($R^2$)—, $R^{15}$—O—, $R^{15}$—S—, $R^{15}$—S(-)$_{1-2}$, $R^{15}$—C(O)—O—, $R^{15}$—C(O)—, $R^{15}$—C(O)—N($R^2$)—, $R^{15}$—N($R^2$)—C(O)—, $R^{15}$—O—C(O)—N($R^2$)—, $R^{15}$—N($R^2$)—C(O)—O—, $R^{15}$—S(O)$_2$—N($R^2$)— or $R^{15}$—N($R^2$)—S(O)$_2$—, then A is not thienyl, thiadiazolyl, thiazolyl, pyrimidyl, pyrazinyl, pyridazinyl, pyridyl, triazinyl or tetrazinyl;
(c)

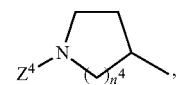

wherein
$n^3$=0-4 and
$Z^3$ is selected from the group consisting of $R^{15}$—, $R^{15}$—C(O)—, $R^{15}$—C(S)—, $R^{15}$—N($R^2$)—, $R^{15}$—O—, $R^{15}$—S—, $R^{15}$—S(O)$_{1-2}$—, $R^{15}$—C(O)—O—, $R^{15}$—O—C(O)—, $R^{15}$—C(O)—S—, $R^{15}$—S—C(O)—, $R^{15}$—C(O)—N($R^2$)—, $R^{15}$—N($R^2$)—C(O), $R^{15}$—C(S)—O—, $R^{15}$—O—C(S)—, $R^{15}$—C(S)—S—, $R^{15}$—S—C(S)—, $R^{15}$—C(S)—N($R^2$)—, $R^5$—N($R^2$)—C(S)—, $R^{15}$—O—C(O)—O—, $R^{15}$—O—C(O)—S—, $R^{15}$—S—C(O)—O—, $R^5$—O—C(O)—N($R^2$)—, $R^{15}$—N($R^2$)—C(O)—O—, $R^{15}$—O—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0-2}$—N($R^2$)—, $R^{15}$—N($R^2$)—S(O)$_{0-2}$— and $R^{15}$—N($R^2$)—S(O)$_{0-2}$—N($R^2$)—;
with the proviso that if $n^3$ is 2 and $Z^3$ is $R^{15}$—, $R^{15}$—C(O)—, $R^{15}$—N($R^2$)—, $R^{15}$—O—, $R^{15}$—S—, $R^{15}$—S(-)$_{1-2}$, $R^{15}$—C(O)—O—, $R^{15}$—O—C(O)—, $R^{15}$—C(O)—N($R^2$)—, $R^{15}$—N($R^2$)—C(O)—, $R^{15}$—O—C(O)—N($R^2$)—, $R^{15}$—N($R^2$)—C(O)—O—, $R^{15}$—S(O)$_2$—N($R^2$)— or $R^{15}$—N($R^2$)—S(O)$_2$— then A is not phenyl, thienyl, thiadiazolyl, thiazolyl, pyrimidyl, pyrazinyl, pyridazinyl, pyridyl, triazinyl or tetrazinyl;
(d)

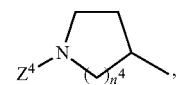

wherein
$n^4$=0, 2, 3 or 4 and
$Z^4$ is selected from the group consisting of $R^{15}$—, $R^{15}$—C(O)—, $R^{15}$—C(S)—, $R^{15}$—N($R^2$)—, $R^{15}$—O—, $R^{15}$—S—, $R^{15}$—S(O)$_{0\text{-}2}$, $R^{15}$—C(O)—O—, $R^{15}$—O—C(O)—, $R^{15}$—C(O)—S—, $R^{15}$—S—C(O)—, $R^{15}$—C(O)—N(R$^2$)—, $R^{15}$—N(R$^2$)—C(O), $R^{15}$—C(S)—O—, $R^{15}$—O—C(S)—, $R^{15}$—C(S)—S—, $R^{15}$—S—C(S)—, $R^{15}$—C(S)—N(R$^2$)—, $R^5$—N(R$^2$)—C(S)—, $R^{15}$—O—C(O)—O—, $R^{15}$—O—C(O)—S—, $R^{15}$—S—C(O)—O—, $R^5$—O—C(O)—N(R$^2$)—, $R^{15}$—N(R$^2$)—C(O)—O—, $R^{15}$—O—C(S)—O—, $R^{15}$—O—C(S)—S—, $R^{15}$—S—C(S)—O—, $R^{15}$—O—C(S)—N(R$^2$)—, $R^{15}$—N(R$^2$)—C(S)—O—, $R^{15}$—S—C(O)—S—, $R^{15}$—S—C(O)—N(R$^2$)—, $R^{15}$—N(R$^2$)—C(O)—S—, $R^{15}$—S—C(S)—S—, $R^{15}$—N(R$^2$)—C(O)—N(R$^2$)—, $R^{15}$—N(R$^2$)—C(S)—N(R$^2$)—, $R^{15}$—N(R$^2$)—C(S)—S—, $R^{15}$—S—C(S)—N(R$^2$)—, $R^{15}$—NH—C(N(R$^2$))—NH—, $R^{15}$—S(O)$_{0\text{-}2}$—N(R$^2$)—, $R^{15}$—N(R$^2$)—S(O)$_{0\text{-}2}$— and $R^{15}$—N(R$^2$)—S(O)$_{0\text{-}2}$—N(R$^2$)—, with the proviso that if $n^4$ is 2 and $Z^4$ is $R^{15}$—, $R^{15}$—C(O)—, $R^{15}$—N(R$^2$)—, $R^{15}$—O—, $R^{15}$—S—, $R^{15}$—S(-)$_{1\text{-}2}$, $R^{15}$—C(O)—O—, $R^{15}$—C(O)—, $R^{15}$—C(O)—N(R$^2$)—, $R^{15}$—N(R$^2$)—C(O)—, $R^{15}$—O—C(O)—N(R$^2$)—, $R^{15}$—N(R$^2$)—C(O)—O—, $R^{15}$—S(O)$_2$—N(R$^2$)— or $R^{15}$—N(R$^2$)—S(O)$_2$— then A is not phenyl, thienyl, thiadiazolyl, thiazolyl, pyrimidyl, pyrazinyl, pyridazinyl, pyridyl, triazinyl or tetrazinyl;

(e)

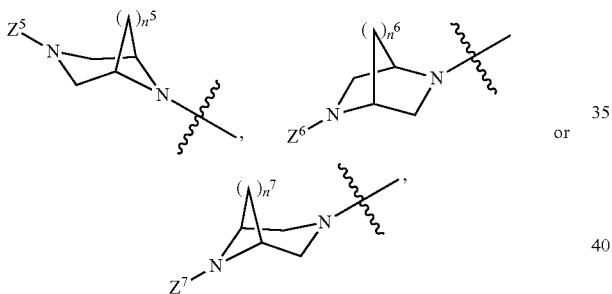

wherein
$n^5$=1-4,
$n^6$=1-4,
$n^7$=1-4,
$Z^5$ is selected from the group consisting of $R^{15}$—, $R^{15}$—C(O)—, $R^{15}$—C(S)—, $R^{15}$—N(R$^2$)—, $R^{15}$—O—, $R^{15}$—S—, $R^{15}$—S(O)$_{1\text{-}2}$, $R^{15}$—C(O)—O—, $R^{15}$—O—C(O)—, $R^{15}$—C(O)—S—, $R^{15}$—S—C(O)—, $R^{15}$—C(O)—N(R$^2$)—, $R^{15}$—N(R$^2$)—C(O), $R^{15}$—C(S)—O—, $R^{15}$—O—C(S)—, $R^{15}$—C(S)—S—, $R^{15}$—S—C(S)—, $R^{15}$—C(S)—N(R$^2$)—, $R^5$—N(R$^2$)—C(S)—, $R^{15}$—O—C(O)—O—, $R^{15}$—O—C(O)—S—, $R^{15}$—S—C(O)—O—, $R^5$—O—C(O)—N(R$^2$)—, $R^{15}$—N(R$^2$)—C(O)—O—, $R^{15}$—O—C(S)—O—, $R^{15}$—O—C(S)—S—, $R^{15}$—S—C(S)—O—, $R^{15}$—O—C(S)—N(R$^2$)—, $R^{15}$—N(R$^2$)—C(S)—O—, $R^{15}$—S—C(O)—S—, $R^{15}$—S—C(O)—N(R$^2$)—, $R^{15}$—N(R$^2$)—C(O)—S—, $R^{15}$—S—C(S)—S—, $R^{15}$—N(R$^2$)—C(O)—N(R$^2$)—, $R^{15}$—N(R$^2$)—C(S)—N(R$^2$)—, $R^{15}$—N(R$^2$)—C(S)—S—, $R^{15}$—S—C(S)—N(R$^2$)—, $R^{15}$—NH—C(N(R$^2$))—NH—, $R^{15}$—S(O)$_{0\text{-}2}$—N(R$^2$)—, $R^{15}$—N(R$^2$)—S(O)$_{0\text{-}2}$— and $R^{15}$—N(R$^2$)—S(O)$_{0\text{-}2}$—N(R$^2$)—;

$Z^6$ is selected from the group consisting of $R^{15}$—, $R^{15}$—C(O)—, $R^{15}$—C(S)—, $R^{15}$—N(R$^2$)—, $R^{15}$—O—, $R^{15}$—S—, $R^{15}$—S(O)$_{0\text{-}2}$, $R^{15}$—C(O)—O—, $R^{15}$—O—C(O)—, $R^{15}$—C(O)—S—, $R^{15}$—S—C(O)—, $R^{15}$—C(O)—N(R$^2$)—, $R^{15}$—N(R$^2$)—C(O), $R^{15}$—C(S)—O—, $R^{15}$—O—C(S)—, $R^{15}$—C(S)—S—, $R^{15}$—S—C(S)—, $R^{15}$—C(S)—N(R$^2$)—, $R^5$—N(R$^2$)—C(S)—, $R^{15}$—O—C(O)—O—, $R^{15}$—O—C(O)—S—, $R^{15}$—S—C(O)—O—, $R^5$—O—C(O)—N(R$^2$)—, $R^{15}$—N(R$^2$)—C(O)—O—, $R^{15}$—O—C(S)—O—, $R^{15}$—O—C(S)—S—, $R^{15}$—S—C(S)—O—, $R^{15}$—O—C(S)—N(R$^2$)—, $R^{15}$—N(R$^2$)—C(S)—O—, $R^{15}$—S—C(O)—S—, $R^{15}$—S—C(O)—N(R$^2$)—, $R^{15}$—N(R$^2$)—C(O)—S—, $R^{15}$—S—C(S)—S—, $R^{15}$—N(R$^2$)—C(O)—N(R$^2$)—, $R^{15}$—N(R$^2$)—C(S)—N(R$^2$)—, $R^{15}$—N(R$^2$)—C(S)—S—, $R^{15}$—S—C(S)—N(R$^2$)—, $R^{15}$—NH—C(N(R$^2$))—NH—, $R^{15}$—S(O)$_{0\text{-}2}$—N(R$^2$)—, $R^{15}$—N(R$^2$)—S(O)$_{0\text{-}2}$— and $R^{15}$—N(R$^2$)—S(O)$_{0\text{-}2}$—N(R$^2$)—; and $Z^7$ is selected from the group consisting of $R^{15}$—, $R^{15}$—C(O)—, $R^{15}$—C(S)—, $R^{15}$—N(R$^2$)—, $R^{15}$—O—, $R^{15}$—S—, $R^{15}$—S(O)$_{0\text{-}2}$, $R^{15}$—C(O)—O—, $R^{15}$—O—C(O)—, $R^{15}$—C(O)—S—, $R^{15}$—S—C(O)—, $R^{15}$—C(O)—N(R$^2$)—, $R^{15}$—N(R$^2$)—C(O), $R^{15}$—C(S)—O—, $R^{15}$—O—C(S)—, $R^{15}$—C(S)—S—, $R^{15}$—S—C(S)—, $R^{15}$—C(S)—N(R$^2$)—, $R^5$—N(R$^2$)—C(S)—, $R^{15}$—O—C(O)—O—, $R^{15}$—O—C(O)—S—, $R^{15}$—S—C(O)—O—, $R^{15}$—O—C(O)—N(R$^2$)—, $R^{15}$—N(R$^2$)—C(O)—O—, $R^{15}$—O—C(S)—O—, $R^{15}$—O—C(S)—S—, $R^{15}$—S—C(S)—O—, $R^{15}$—O—C(S)—N(R$^2$)—, $R^5$—N(R$^2$)—C(S)—O—, $R^{15}$—S—C(O)—S—, $R^{15}$—S—C(O)—N(R$^2$)—, $R^{15}$—N(R$^2$)—C(O)—S—, $R^{15}$—S—C(S)—S—, $R^{15}$—N(R$^2$)—C(O)—N(R$^2$)—, $R^{15}$—N(R$^2$)—C(S)—N(R$^2$)—, $R^{15}$—N(R$^2$)—C(S)—S—, $R^{15}$—S—C(S)—N(R$^2$)—, $R^{15}$—NH—C(N(R$^2$))—NH—, $R^{15}$—S(O)$_{0\text{-}2}$—N(R$^2$)—, $R^{15}$—N(R$^2$)—S(O)$_{0\text{-}2}$— and $R^{15}$—N(R$^2$)—S(O)$_{0\text{-}2}$—N(R$^2$)—; or (f)

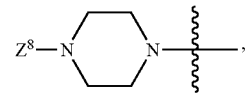

wherein
$Z^8$ is selected from the group consisting of $R^{15}$—, $R^{15}$—C(O)—, $R^{15}$—C(S)—, $R^{15}$—N(R$^2$)—, $R^{15}$—O—, $R^{15}$—S—, $R^{15}$—S(O)$_{1\text{-}2}$, $R^{15}$—C(O)—O—, $R^{15}$—O—C(O)—, $R^{15}$—C(O)—S—, $R^{15}$—S—C(O)—, $R^{15}$—C(O)—N(R$^2$)—, $R^{15}$—N(R$^2$)—C(O), $R^{15}$—C(S)—O—, $R^{15}$—O—C(S)—, $R^{15}$—C(S)—S—, $R^{15}$—S—C(S)—, $R^{15}$—C(S)—N(R$^2$)—, $R^5$—N(R$^2$)—C(S)—, $R^{15}$—O—C(O)—O—, $R^{15}$—O—C(O)—S—, $R^{15}$—S—C(O)—O—, $R^5$—O—C(O)—N(R$^2$)—, $R^{15}$—N(R$^2$)—C(O)—O—, $R^{15}$—O—C(S)—O—, $R^{15}$—O—C(S)—S—, $R^{15}$—S—C(S)—O—, $R^{15}$—O—C(S)—N(R$^2$)—, $R^{15}$—N(R$^2$)—C(S)—O—, $R^{15}$—S—C(O)—S—, $R^{15}$—S—C(O)—N(R$^2$)—, $R^{15}$—N(R$^2$)—C(O)—S—, $R^{15}$—S—C(S)—S—, $R^{15}$—N(R$^2$)—C(O)—N(R$^2$)—, $R^{15}$—N(R$^2$)—C(S)—N(R$^2$)—, $R^{15}$—N(R$^2$)—C(S)—S—, $R^{15}$—S—C(S)—N(R$^2$)—, $R^{15}$—NH—C(N(R$^2$))—NH—, $R^{15}$—S(O)$_{0-2}$—N(R$^2$)—, $R^{15}$—N(R$^2$)—S(O)$_{0-2}$— and $R^{15}$—N(R$^2$)—S(O)$_{0-2}$—N(R$^2$)—, with the proviso that if $Z^8$ is $R^{15}$—, $R^{15}$—C(O)—, $R^{15}$—N(R$^2$)—, $R^{15}$—O—$R^{15}$—S—, $R^{15}$—S(O)$_{1-2}$—, $R^{15}$—C(O)—O—, $R^{15}$—O—C(O)—, $R^{15}$—C(O)—N(R$^2$)—, $R^{15}$—N(R$^2$)—C(O)—, $R^{15}$—O—C(O)—N(R$^2$)—, $R^{15}$—N(R$^2$)—C(O)—O—, $R^{15}$—S(O)$_2$—N(R$^2$)— or $R^{15}$—N(R$^2$)—S(O)$_2$— then A is not phenyl, thienyl, thiadiazolyl, thiazolyl, pyrimidyl, pyrazinyl, pyridazinyl, pyridyl, triazinyl or tetrazinyl, in which each $R^2$ is independently selected from the group consisting of hydrogen, (C$_1$-C$_5$ alkyl)-, Ar—(C$_0$-C$_4$ alkyl)-, Het-(C$_0$-C$_4$ alkyl)-, Hca-(C$_0$-C$_4$ alkyl)-, Cak-(C$_0$-C$_4$ alkyl)-, $R^{14}$—CO—, $R^{14}$—SO2—, $R^{14}$—CO—NH— and $R^{14}$—CO—O—, in which each alkyl is optionally substituted;

each $R^5$ is independently selected from the group consisting of H—, optionally substituted (C$_1$-C$_6$ hydrocarbyl)-, Ar—(C$_1$-C$_6$ hydrocarbyl)-, Het-(C$_1$-C$_6$ hydrocarbyl)-, Hca-(C$_0$-C$_6$ hydrocarbyl)- and Cak-(C$_0$-C$_6$ hydrocarbyl)-;

each $R^6$ is independently selected from the group consisting of H—, substituted (C$_1$-C$_6$ hydrocarbyl)- with the proviso that if the (C$_1$-C$_6$ hydrocarbyl) has only one substituent, it is not halo or amino, Hca-(C$_0$-C$_1$ or C$_3$-C$_6$ hydrocarbyl)- and Cak-(C$_0$-C$_6$ hydrocarbyl)-;

each $R^7$ is independently selected from the group consisting of H, optionally substituted (C$_1$-C$_6$ hydrocarbyl)-, Hca-(C$_0$-C$_1$ or C$_3$-C$_6$ hydrocarbyl)- and Cak-(C$_0$-C$_6$ hydrocarbyl)-;

each $R^8$ is independently selected from the group consisting of optionally substituted (C$_1$-C$_6$ hydrocarbyl)-, Ar—(C$_1$-C$_6$ hydrocarbyl)-, Het-(C$_1$-C$_6$ hydrocarbyl)-, Hca-(C$_0$-C$_6$ hydrocarbyl)- and Cak-(C$_0$-C$_6$ hydrocarbyl)-, with the proviso that $R^8$ is not 2(morpholin-4-yl)ethyl;

each $R^9$ is independently selected from the group consisting of Hca-(C$_0$-C$_6$ hydrocarbyl)- and Cak-(C$_0$-C$_6$ hydrocarbyl)-;

each $R^{10}$ is independently selected from the group consisting of H—, Hca-(C$_0$-C$_6$ hydrocarbyl)- and Cak-(C$_0$-C$_6$ hydrocarbyl)-;

each $R^{11}$ is independently selected from the group consisting of H—, (C$_1$-C$_6$ hydrocarbyl)-, Hca-(C$_0$-C$_6$ hydrocarbyl)- and Cak-(C$_0$-C$_6$ hydrocarbyl)-;

each $R^{12}$ is independently selected from the group consisting of optionally substituted (C$_1$-C$_6$ hydrocarbyl)-, Ar—(C$_1$-C$_6$ hydrocarbyl)-, Het-(C$_1$-C$_6$ hydrocarbyl)-, Hca-(C$_0$-C$_6$ hydrocarbyl)-, Cak-(C$_0$-C$_6$ hydrocarbyl)-;

each $R^{13}$ is independently selected from the group consisting of H—, optionally substituted (C$_1$-C$_6$ hydrocarbyl)-, Hca-(C$_0$-C$_6$ hydrocarbyl)- and Cak-(C$_0$-C$_6$ hydrocarbyl)-;

each $R^{14}$ is independently selected from the group consisting of Ar— and optionally substituted (C$_1$-C$_6$ hydrocarbyl)-; and each $R^{15}$ is independently selected from the group consisting of H—, optionally substituted (C$_1$-C$_6$ hydrocarbyl)-, Ar—(C$_0$-C$_6$ hydrocarbyl)-, Het-(C$_0$-C$_6$ hydrocarbyl)-, Hca-(C$_0$-C$_6$ hydrocarbyl)- and Cak-(C$_0$-C$_6$ hydrocarbyl)-;

in which any (C$_1$-C$_6$ hydrocarbyl)-moiety is optionally substituted, and each Ar is independently an optionally substituted aryl, each Het is independently an optionally substituted heteroaryl, each Hca is independently an optionally substituted heterocycloalkyl, and each Cak is independently an optionally substituted cycloalkyl.

Reference to a compound of formula (1) (or equivalently, a compound according to the first aspect, or a compound according to the present invention, and the like), herein is understood to include reference to N-oxides, hydrates, solvates, pharmaceutically acceptable salts, prodrugs and complexes thereof, and racemic and scalemic mixtures, diastereomers, enantiomers and tautomers thereof, unless otherwise indicated.

In a preferred embodiment of the compounds according to the present invention, hydrocarbyl is alkyl.

In a preferred embodiment of the compounds according to the present invention, C$_0$-C$_6$ hydrocarbyl is substituted with a moiety selected from the group consisting of amino, alkylamino, di-alkylamino, alkoxy and halo.

Another aspect of the invention relates to pharmaceutical compositions comprising a compound according to formula (1) or an N-oxide, hydrate, solvate, pharmaceutically acceptable salt, complex or prodrug thereof, or a racemic mixture, diastereomer, enantiomer or tautomer thereof, and a pharmaceutically acceptable carrier, excipient or diluent.

Another aspect of the invention relates to a method of inhibiting histone deacetylase, preferably in a cell, the method comprising contacting the cell with one or more compounds of formula (1) or N-oxides, hydrates, solvates, pharmaceutically acceptable salts, complexes or prodrugs thereof, or racemic mixtures, diastereomers, enantiomers or tautomers thereof.

Another aspect of the invention relates to a method for treating a cell proliferative disease or condition in an animal in need of such treatment, the method comprising administering to the animal a therapeutically effective amount of one or more compounds of formula (1) or N-oxides, hydrates, solvates, pharmaceutically acceptable salts, complexes or prodrugs thereof, or racemic mixtures, diastereomers, enantiomers or tautomers thereof.

The foregoing merely summarizes certain aspects of the invention and is not intended to be limiting in nature. These aspects and other aspects and embodiments are described more fully below.

DETAILED DESCRIPTION OF THE PREFERRED EMBODIMENTS

The invention provides compounds, compositions and methods for inhibiting histone deacetylase enzymatic activity. The invention also provides compounds, compositions and methods for treating cell proliferative diseases and conditions. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

As used herein, the terms "histone deacetylase" and "HDAC" are intended to refer to any one of a family of enzymes that remove acetyl groups from the ϵ-amino groups of lysine residues at the N-terminus of a histone. Unless otherwise indicated by context, the term "histone" is meant to refer to any histone protein, including H1, H2A, H2B, H3, H4, and H5, from any species. Preferred histone deacetylases include class I and class II enzymes. Examples of preferred human HDACs, include, but are not limited to, HDAC-1, HDAC-2, HDAC-3, HDAC-4, HDAC-5, HDAC-6, HDAC-7, HDAC-8, HDAC-9, HDAC-10, HDAC-11, SirT1, SirT2, SirT3, SirT4, SirT5, SirT6 and SirT7. In some other preferred embodiments of the invention, the histone deacetylase is derived from a plant, protozoal or fungal source.

The terms "histone deacetylase inhibitor" and "inhibitor of histone deacetylase" are used to identify a compound which is capable of interacting with a histone deacetylase and inhibiting its enzymatic activity.

The term "inhibiting histone deacetylase enzymatic activity" is used to mean reducing the ability of a histone deacetylase to remove an acetyl group from a histone. For example, the inhibition of histone deacetylase activity may be at least about 10%. In some preferred embodiments of the invention, such reduction of histone deacetylase activity is at least about 50%, more preferably at least about 75%, and still more preferably at least about 90%. In other preferred embodiments, histone deacetylase activity is reduced by at least 95% and even more preferably by at least 99%. The $IC_{50}$ value is the concentration of histone deacetylase inhibitor which reduces the activity of a histone deacetylase to 50% of the uninhibited enzyme.

The term "inhibiting effective amount" is meant to denote a dosage sufficient to cause inhibition of histone deacetylase activity. The histone deacetylase may be in a cell, which in turn may be in a multicellular organism. The multicellular organism may be, for example, a plant, a fungus or an animal, preferably a mammal and more preferably a human. The fungus may be infecting a plant or a mammal, preferably a human, and could therefore be located in and/or on the plant or mammal. If the histone deacetylase is in a multicellular organism, the method according to this aspect of the invention comprises the step of administering to the organism a compound or composition according to the present invention. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

Preferably, such inhibition is specific, i.e., the histone deacetylase inhibitor reduces the ability of a histone deacetylase to remove an acetyl group from a histone at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect.

Reference to "a compound of the formula (1)" (or equivalently, "a compound according to the first aspect", or "a compound of the present invention", and the like), herein is understood to include reference to N-oxides, hydrates, solvates, pharmaceutically acceptable salts, prodrugs and complexes thereof, and racemic mixtures, diastereomers, enantiomers and tautomers thereof and unless otherwise indicated.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—.

For simplicity, reference to a "$C_n$-$C_m$" heterocyclyl or "$C_n$-$C_m$" heteroaryl means a heterocyclyl or heteroaryl having from "n" to "m" annular atoms, where "n" and "m" are integers. Thus, for example, a $C_5$-$C_6$-heterocyclyl is a 5- or 6-membered ring having at least one heteroatom, and includes pyrrolidinyl ($C_5$) and piperazinyl and piperidinyl ($C_6$); $C_6$-heteroaryl includes, for example, pyridyl and pyrimidyl.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$ hydrocarbyl" includes a covalent bond, methyl, ethyl, ethenyl, ethynyl, propyl, propenyl, propynyl, and cyclopropyl.

The term "alkyl" is intended to mean a straight chain or branched aliphatic group having from 1 to 12 carbon atoms, preferably 1-8 carbon atoms, and more preferably 1-6 carbon atoms. Other preferred alkyl groups have from 2 to 12 carbon atoms, preferably 2-8 carbon atoms and more preferably 2-6 carbon atoms. Preferred alkyl groups include, without limitation, methyl, ethyl, propyl, isopropyl, butyl, isobutyl, sec-butyl, tert-butyl, pentyl, hexyl and the like. A "$C_0$" alkyl (as in "$C_0$-$C_3$alkyl") is a covalent bond.

The term "alkenyl" is intended to mean an unsaturated straight chain or branched aliphatic group with one or more carbon-carbon double bonds, having from 2 to 12 carbon atoms, preferably 2-8 carbon atoms, and more preferably 2-6 carbon atoms. Preferred alkenyl groups include, without limitation, ethenyl, propenyl, butenyl, pentenyl, and hexenyl.

The term "alkynyl" is intended to mean an unsaturated straight chain or branched aliphatic group with one or more carbon-carbon triple bonds, having from 2 to 12 carbon atoms, preferably 2-8 carbon atoms, and more preferably 2-6 carbon atoms. Preferred alkynyl groups include, without limitation, ethynyl, propynyl, butynyl, pentynyl, and hexynyl.

The terms "alkylene," "alkenylene," or "alkynylene" as used herein are intended to mean an alkyl, alkenyl, or alkynyl group, respectively, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "cycloalkyl" is intended to mean a saturated or unsaturated mono-, bi-, tri- or poly-cyclic hydrocarbon group having about 3 to 15 carbons, preferably having 3 to 12 carbons, preferably 3 to 8 carbons, more preferably 3 to 6 carbons, and more preferably still 5 or 6 carbons. In certain preferred embodiments, the cycloalkyl group is fused to an aryl, heteroaryl or heterocyclic group. Preferred cycloalkyl groups include, without limitation, cyclopenten-2-enone, cyclopenten-2-enol, cyclohex-2-enone, cyclohex-2-enol, cyclopropyl, cyclobutyl, cyclobutenyl, cyclopentyl, cyclopentenyl, cyclohexyl, cyclohexenyl, cycloheptyl, cyclooctyl, etc.

The term "heteroalkyl" is intended to mean a saturated or unsaturated, straight chain or branched aliphatic group, wherein one or more carbon atoms in the group are independently replaced by a heteroatom selected from the group consisting of O, S, and N.

The term "aryl" is intended to mean a mono-, bi-, tri- or polycyclic aromatic moiety, preferably a $C_6$-$C_{14}$aromatic moiety, preferably comprising one to three aromatic rings. Preferably, the aryl group is a $C_6$-$C_{10}$aryl group, more preferably a $C_6$aryl group. Preferred aryl groups include, without limitation, phenyl, naphthyl, anthracenyl, and fluorenyl.

The terms "aralkyl" or "arylalkyl" is intended to mean a group comprising an aryl group covalently linked to an alkyl group. If an aralkyl group is described as "optionally substituted", it is intended that either or both of the aryl and alkyl moieties may independently be optionally substituted or unsubstituted. Preferably, the aralkyl group is $(C_1$-$C_6)$alk$(C_6$-$C_{10})$aryl, including, without limitation, benzyl, phenethyl, and naphthylmethyl. For simplicity, when written as "aralkyl" this term, and terms related thereto, is intended to indicate the order of groups in a compound as "aryl-alkyl". Similarly, "alkyl-aryl" is intended to indicate the order of the groups in a compound as "alkyl-aryl".

The terms "heterocyclyl", "heterocyclic" or "heterocycle" are intended to mean a group which is a mono-, bi-, or polycyclic structure having from about 3 to about 14 atoms, wherein one or more atoms are independently selected from the group consisting of N, O, and S. The ring structure may be saturated, unsaturated or partially unsaturated. In certain preferred embodiments, the heterocyclic group is non-aromatic, in which case the group is also known as a heterocycloalkyl. In a bicyclic or polycyclic structure, one or more rings may be aromatic; for example one ring of a bicyclic heterocycle or one or two rings of a tricyclic heterocycle may be aromatic, as in indan and 9,10-dihydro anthracene. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In certain preferred embodiments, the heterocyclic group is a heteroaryl group. As used herein, the term "heteroaryl" is intended to mean a mono-, bi-, tri- or polycyclic group having 5 to 14 ring atoms, preferably 5, 6, 9, or 10 ring atoms; having 6, 10, or 14 pi electrons shared in a cyclic array; and having, in addition to carbon atoms, between one or more heteroatoms independently selected from the group consisting of N, O, and S. For example, a heteroaryl group may be pyrimidinyl, pyridinyl, benzimidazolyl, thienyl, benzothiazolyl, benzofuranyl and indolinyl. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

The terms "arylene," "heteroarylene," or "heterocyclylene" are intended to mean an aryl, heteroaryl, or heterocyclyl group, respectively, as defined hereinabove, that is positioned between and serves to connect two other chemical groups.

Preferred heterocylyls and heteroaryls include, but are not limited to, azepinyl, azetidinyl, acridinyl, azocinyl, benzidolyl, benzimidazolyl, benzofuranyl, benzofurazanyl, benzofuryl, benzothiofuranyl, benzothiophenyl, benzoxazolyl, benzothiazolyl, benzothienyl, benztriazolyl, benztetrazolyl, benzisoxazolyl, benzisothiazolyl, benzimidazolinyl, benzoxazolyl, benzoxadiazolyl, benzopyranyl, carbazolyl, 4aH-carbazolyl, carbolinyl, chromanyl, chromenyl, cinnolinyl, coumarinyl, decahydroquinolinyl, 1,3-dioxolane, 2H,6H-1,5,2-dithiazinyl, dihydrofuro[2,3-b]tetrahydrofuran, dihydroisoindolyl, dihydroquinazolinyl (such as 3,4-dihydro-4-oxo-quinazolinyl), furanyl, furopyridinyl (such as fluor[2,3-c]pyridinyl, furo[3,2-b]pyridinyl or furo[2,3-b]pyridinyl), furyl, furazanyl, hexahydrodiazepinyl, imidazolidinyl, imidazolinyl, imidazolyl, indazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolidinyl, isothiazolyl, isoxazolinyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxetanyl, 2-oxoazepinyl, 2-oxopiperazinyl, 2-oxopiperidinyl, 2-oxopyrrolodinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolopyridyl, 2H-pyrrolyl, pyrrolyl, quinazolinyl, quinolinyl, 4H-quinolizinyl, quinoxalinyl, quinuclidinyl, tetrahydro-1,1-dioxothienyl, tetrahydrofuranyl, tetrahydrofuryl, tetrahydroisoquinolinyl, tetrahydroquinolinyl, tetrahydropyranyl, tetrazolyl, thiazolidinyl, 6H-1,2,5-thiadiazinyl, thiadiazolyl (e.g., 1,2,3-thiadiazolyl, 1,2,4-thiadiazolyl, 1,2,5-thiadiazolyl, 1,3,4-thiadiazolyl), thiamorpholinyl, thiamorpholinyl sulfoxide, thiamorpholuiyl sulfone, thianthrenyl, thiazolyl, thienyl, thienothiazolyl, thienooxazolyl, thienoimidazolyl, thiophenyl, triazinyl, triazinylazepinyl, triazolyl (e.g., 1,2,3-triazolyl, 1,2,4-triazolyl, 1,2,5-triazolyl, 1,3,4-triazolyl), and xanthenyl.

As employed herein, and unless stated otherwise, when a moiety (e.g., alkyl, heteroalkyl, cycloalkyl, aryl, heteroaryl, heterocyclyl, etc.) is described as "optionally substituted" it is meant that the group optionally has from one to four, preferably from one to three, more preferably one or two, independently selected non-hydrogen substituents. Suitable substituents include, without limitation, halo, hydroxy, oxo (e.g., an annular —CH-substituted with oxo is —C(O)—) nitro, halohydrocarbyl, hydrocarbyl, alkyl, cycloalkyl, heterocyclyl, aryl, heteroaryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:
(a) halo, cyano, oxo, carboxy, formyl, nitro, amino, amidino, guanidino,
(b) $C_1$-$C_5$alkyl or alkenyl or arylalkyl imino, carbamoyl, azido, carboxamido, mercapto, hydroxy, hydroxyalkyl, alkylaryl, arylalkyl, $C_1$-$C_8$alkyl, $C_1$-$C_8$alkenyl, $C_1$-$C_8$alkoxy, $C_1$-$C_8$alkyamino, $C_1$-$C_8$alkoxycarbonyl, aryloxycarbonyl, $C_2$-$C_8$acyl, $C_2$-$C_8$acylamino, $C_1$-$C_8$alkylthio, arylalkylthio, arylthio, $C_1$-$C_8$alkylsulfinyl, arylalkylsulfinyl, arylsulfinyl, $C_1$-$C_8$alkylsulfonyl, arylalkylsulfonyl, arylsulfonyl, $C_0$-$C_6$N-alkyl carbamoyl, $C_2$-$C_{15}$N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$heterocycle, $C_5$-$C_{15}$heteroaryl or any of these rings fused or spiro-fused to a cycloalkyl, heterocyclyl, or aryl, wherein each of the foregoing is further optionally substituted with one more moieties listed in (a), above; and (c) —$(CR^{32}R^{33})$, —$NR^{30}R^{31}$, wherein s is from 0 (in which case the nitrogen is directly bonded to the moiety that is substituted) to 6, $R^{32}$ and $R^{33}$ are each independently hydrogen, halo, hydroxyl or $C_1$-$C_4$alkyl, and $R^{30}$ and $R^{31}$ are each independently hydrogen, cyano, oxo, hydroxyl, $C_1$-$C_8$alkyl, $C_1$-$C_8$heteroalkyl, $C_1$-$C_8$alkenyl, carboxamido, $C_1$-$C_3$alkyl-carboxamido, carboxamido-$C_1$-$C_3$alkyl, amidino, $C_2$-$C_8$hydroxyalkyl, $C_1$-$C_3$alkylaryl, aryl-$C_1$-$C_3$alkyl, $C_1$-$C_3$alkylheteroaryl, heteroaryl-$C_1$-$C_3$alkyl, $C_1$-$C_3$alkylheterocyclyl, heterocyclyl-$C_1$-$C_3$alkyl $C_1$-$C_3$alkylcycloalkyl, cycloalkyl-$C_1$-$C_3$alkyl, $C_2$-$C_8$alkoxy, $C_2$-$C_8$alkoxy-$C_1$-$C_4$alkyl, $C_1$-$C_8$alkoxycarbonyl, aryloxycarbonyl, aryl-$C_1$-$C_3$alkoxycarbonyl, heteroaryloxycarbonyl, heteroaryl-$C_1$-$C_3$alkoxycarbonyl, $C_1$-$C_8$acyl, $C_0$-$C_8$alkyl-carbonyl, aryl-$C_0$-$C_8$alkyl-carbonyl, heteroaryl-$C_0$-$C_8$alkyl-carbonyl, cycloalkyl-$C_0$-$C_8$alkyl-carbonyl, $C_0$-$C_8$alkyl-NH-carbonyl, aryl-$C_0$-$C_8$alkyl-NH-carbonyl, heteroaryl-$C_0$-$C_8$alkyl-NH-carbonyl, cycloalkyl-$C_0$-$C_8$alkyl-NH-carbonyl, $C_0$-$C_8$alkyl-O-carbonyl, aryl-$C_0$-$C_8$alkyl-O-carbonyl, heteroaryl-$C_0$-$C_8$alkyl-O-carbonyl, cycloalkyl-$C_0$-$C_8$alkyl-O-carbonyl, $C_1$-$C_8$alkylsulfonyl, arylalkylsulfonyl, arylsulfonyl, heteroarylalkylsulfonyl, heteroarylsulfonyl, $C_1$-$C_8$alkyl-NH-sulfonyl, arylalkyl-NH-sulfonyl, aryl-NH-sulfonyl, heteroarylalkyl-NH-sulfonyl, heteroaryl-NH-sulfonyl aroyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, or protecting group, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents selected from the group consisting of (a) above, a protecting group, and ($X^{30}$—$Y^{31}$—), wherein said heterocyclyl may also be bridged (forming a bicyclic moiety with a methylene, ethylene or propylene bridge); wherein $X^{30}$ is selected from the group consisting of $C_1$-$C_8$alkyl, $C_2$-$C_8$alkenyl-, $C_2$-$C_8$alkynyl-, —$C_0$-$C_3$alkyl-$C_2$-$C_8$alkenyl-$C_0$-$C_3$alkyl, $C_0$-$C_3$alkyl-$C_2$-$C_8$alkynyl-$C_0$-$C_3$alkyl, $C_0$-$C_3$alkyl-O—$C_0$-$C_3$alkyl-, HO—$C_0$-$C_3$alkyl-, $C_0$-$C_4$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkenyl-, N($R^{30}$)($R^{31}$)—$C_0$-$C_3$alkynyl-, $(N(R^{30})(R^{31}))_2$—C=N—, $C_0$-$C_3$alkyl-$S(O)_{0-2}$—$C_0$-$C_3$alkyl-, $CF_3$—CO—$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with from 1 to 3 substituents from (a); and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C(NR$^{30}$)—N($R^{31}$)—, —N($R^{30}$)—C(N$R^{31}$)—, —C(N$R^{31}$)—N($R^{30}$)—, —N($R^{30}$)—C(S)—N($R^{31}$)—, —N($R^{30}$)—C(O)—O—, —O—C(O)—N($R^{31}$)—, —N($R^{30}$)—C(S)—, —O—C(S)—N($R^{31}$)—, —$S(O)_{0-2}$—, —$SO_2$N($R^{31}$)—, —N($R^{31}$)—$SO_2$— and —N($R^{30}$)—$SO_2$N($R^{31}$)—.

A moiety that is substituted is one in which one or more (preferably one to four, preferably from one to three and more preferably one or two), hydrogens have been independently replaced with another chemical substituent. As a non-limiting example, substituted phenyls include 2-fluorophenyl, 3,4-dichlorophenyl, 3-chloro-4-fluoro-phenyl, 2-fluoro-3-propylphenyl. As another non-limiting example, substituted n-octyls include 2,4-dimethyl-5-ethyl-octyl and 3-cyclopentyl-octyl. Included within this definition are methylenes (—CH$_2$—) substituted with oxygen to form carbonyl —CO—.

When there are two optional substituents bonded to adjacent atoms of a ring structure, such as for example a phenyl, thiophenyl, or pyridinyl, the substituents, together with the atoms to which they are bonded, optionally form a 5- or 6-membered cycloalkyl or heterocycle having 1, 2, or 3 annular heteroatoms.

In a preferred embodiment, a hydrocarbyl, heteroalkyl, heterocyclic and/or aryl group is unsubstituted.

In other preferred embodiments, a hydrocarbyl, heteroalkyl, heterocyclic and/or aryl group is substituted with from 1 to 3 independently selected substituents.

Preferred substituents on alkyl groups include, but are not limited to, hydroxyl, halogen (e.g., a single halogen substituent or multiple halo substituents; in the latter case, groups such as $CF_3$ or an alkyl group bearing $Cl_3$), oxo, cyano, nitro, alkyl, cycloalkyl, alkenyl, cycloalkenyl, alkynyl, heterocycle, aryl, —$OR^a$, —$SR^a$, —S(=O)$R^e$, —S(=O)$_2R^e$, —P(=O)$_2R^e$, —S(=O)$_2OR^e$, —P(=O)$_2OR^e$, —$NR^bR^c$, —$NR^b$S(=O)$_2R^e$, —$NR^bP$(=O)$_2R^e$, —S(=O)$_2NR^bR^c$, —P(=O)$_2NR^bR^c$, —C(=O)$OR^e$, —C(=O)$R^a$, —C(=O)$NR^bR^c$, —OC(=O)$R^a$, —OC(=O)$NR^bR^c$, —$NR^bC$(=O)$OR^e$, —$NR^dC$(=O)$NR^bR^c$, —$NR^dS$(=O)$_2NR^bR^c$, —$NR^dP$(=O)$_2NR^bR^c$, —$NR^bC$(=O)$R^a$ or —$NR^bP$(=O)$_2R^e$, wherein $R^a$ is hydrogen, alkyl, cycloalkyl, alkenyl, cycloalkenyl, alkynyl, heterocycle or aryl; $R^b$, $R^c$ and $R^d$ are independently hydrogen, alkyl, cycloalkyl, heterocycle or aryl, or said $R^b$ and $R^c$ together with the N to which they are bonded optionally form a heterocycle; and $R^e$ is alkyl, cycloalkyl, alkenyl, cycloalkenyl, alkynyl, heterocycle or aryl. In the aforementioned exemplary substituents, groups such as alkyl, cycloalkyl, alkenyl, alkynyl, cycloalkenyl, heterocycle and aryl can themselves be optionally substituted.

Preferred substituents on alkenyl and alkynyl groups include, but are not limited to, alkyl or substituted alkyl, as well as those groups recited as preferred alkyl substituents.

Preferred substituents on cycloalkyl groups include, but are not limited to, nitro, cyano, alkyl or substituted alkyl, as well as those groups recited about as preferred alkyl substituents. Other preferred substituents include, but are not limited to, spiro-attached or fused cyclic substituents, preferably spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Preferred substituents on cycloalkenyl groups include, but are not limited to, nitro, cyano, alkyl or substituted alkyl, as well as those groups recited as preferred alkyl substituents. Other preferred substituents include, but are not limited to, spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Preferred substituents on aryl groups include, but are not limited to, nitro, cycloalkyl or substituted cycloalkyl, cycloalkenyl or substituted cycloalkenyl, cyano, alkyl or substituted alkyl, as well as those groups recited above as preferred alkyl substituents. Other preferred substituents include, but are not limited to, fused cyclic groups, especially fused cycloalkyl, fused cycloalkenyl, fused heterocycle, or fused aryl, where the aforementioned cycloalkyl, cylcoalkenyl, heterocycle and aryl substituents can themselves be optionally substituted. Still other preferred substituents on aryl groups (phenyl, as a non-limiting example) include, but are not limited to, haloalkyl and those groups recited as preferred alkyl substituents.

Preferred substituents on heterocylic groups include, but are not limited to, cycloalkyl, substituted cycloalkyl, cycloalkenyl, substituted cycloalkenyl, nitro, oxo (i.e., =O), cyano, alkyl, substituted alkyl, as well as those groups recited as preferred alkyl substituents. Other preferred substituents on heterocyclic groups include, but are not limited to, spiro-attached or fused cyclic substituents at any available point or points of attachment, more preferably spiro-attached cycloalkyl, spiro-attached cycloalkenyl, spiro-attached heterocycle (excluding heteroaryl), fused cycloalkyl, fused cycloakenyl, fused heterocycle and fused aryl, where the aforementioned cycloalkyl, cycloalkenyl, heterocycle and aryl substituents can themselves be optionally substituted.

In certain preferred embodiments, a heterocyclic group is substituted on carbon, nitrogen and/or sulfur at one or more positions. Preferred substituents on nitrogen include, but are not limited to alkyl, aryl, aralkyl, alkylcarbonyl, alkylsulfonyl, arylcarbonyl, arylsulfonyl, alkoxycarbonyl, or aralkoxycarbonyl. Preferred substituents on sulfur include, but are not limited to, oxo and $C_{1-6}$alkyl. In certain preferred embodiments, nitrogen and sulfur heteroatoms may independently be optionally oxidized and nitrogen heteroatoms may independently be optionally quaternized.

Especially preferred substituents on ring groups, such as aryl, heteroaryl, cycloalkyl and heterocyclyl, include halogen, alkoxy and alkyl.

Especially preferred substituents on alkyl groups include halogen and hydroxy.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally optionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" as used herein means a chemical moiety comprising one or more unpaired electrons.

Where optional substituents are chosen from "one or more" groups it is to be understood that this definition includes all substituents being chosen from one of the specified groups or the substituents being chosen from two or more of the specified groups.

In addition, substituents on cyclic moieties (i.e., cycloalkyl, heterocyclyl, aryl, heteroaryl) include 5- to 6-membered mono- and 9- to 14-membered bi-cyclic moieties fused to the parent cyclic moiety to form a bi- or tri-cyclic fused ring system. Substituents on cyclic moieties also include 5- to 6-membered mono- and 9- to 14-membered bi-cyclic moieties attached to the parent cyclic moiety by a covalent bond to form a bi- or tri-cyclic bi-ring system. For example, an optionally substituted phenyl includes, but is not limited to, the following:

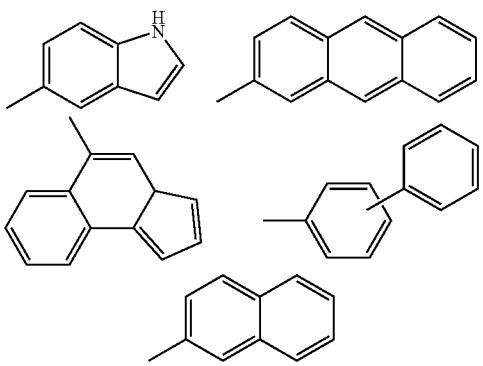

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, "unsubstituted aryl" does not include phenyl substituted with any of the optional substituents for which the definition of the moiety (above) otherwise provides.

Compounds

One aspect of the invention provides compounds of formula (1):

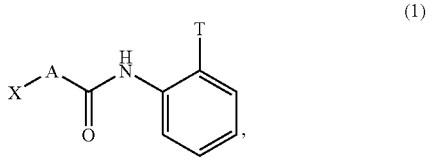

or N-oxides, hydrates, solvates, pharmaceutically acceptable salts, complexes or prodrugs thereof, or racemic or scalemic mixtures, diastereomers, enantiomers or tautomers thereof.

In compounds of formula (1), T may be $NH_2$ or OH. In certain preferred embodiments of the invention, T is $NH_2$—In other preferred embodiments of the invention, T is OH.

In compounds of formula (1), A is selected from the group consisting of aryl, heteroaryl, cycloalkyl and heterocycloalkyl, each of which is optionally substituted. According to one aspect of the invention, A is unsubstituted or optionally substituted arylene. For example, A may be optionally substituted phenylene or naphthylene. In certain desirable embodiments of the invention, A is unsubstituted phenylene. According to other aspects of the invention, A is unsubstituted heteroarylene or optionally substituted heteroarylene. For example, A may be unsubstituted or optionally substituted pyridylene, pyrazinylene, pyrimidylene or pyrazinylene; or may be unsubstituted or optionally substituted thiazinylene thienylene, furylene, selenophenylene, pyrrolylene, imidazolylene, pyrazolylene, pyridylene, pyrazinylene, pyrimidinylene, tetrazolylene, oxazolylene, thiazolylene, pyrazolylene, triazolylene, isothiazolylene, oxadiazolylene, pyrrolylene and isoxazolylene. In certain desirable embodiments of the invention, A is unsubstituted or optionally substituted phenylene, thienylene, thiadiazolylene, thiazolylene, pyrimidylene, pyrazinylene, pyridazinylene, triazinylene or tetrazinylene. When A is a 6-membered ring, the X— and carbonyl moieties are preferably arranged in a 1,4-fashion relative to one another on the ring. When A is a five-membered ring, the X— and carbonyl moieties are preferably arranged in a 1,3-fashion relative to one another on the ring.

According to one aspect of the invention, in compounds of formula (1) X has the structure

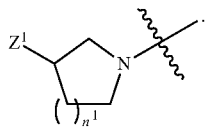

In this aspect of the invention, $n^1=0-4$. In certain desirable embodiments of the invention, $n^1$ is 1 or 2, and is preferably 1. In other embodiments of the invention, $n^1$ is 0 or 3-4. When $n^1$ is 1, the compound desirably has (S)-stereochemical configuration at the carbon to which $Z^1$ is connected. As shown in more detail in the examples, below, the inventors have found that compounds having $n^1=1$ and (S)-stereochemical attachment of $Z^1$ provide very good results with respect to HDAC inhibition. However, in other embodiments of the invention the compound has (R)-stereochemical configuration at the carbon to which $Z^1$ is connected, or exists as a racemic or scalemic mixture. When $n^1$ is 2-4, the compound may have (S)-stereochemical configuration, have (R)-stereochemical configuration, or exist as a racemic or scalemic mixture, at the carbon to which $Z^1$ is attached.

In this aspect of the invention, $Z^1$ is selected from the group consisting of $R^9$—, $R^{13}$—C(O)—, $R^{13}$—C(S)—, $R^7$—N($R^2$)—, $R^6$—O—, $R^{10}$—S—, $R^{13}$—S(O)$_{1-2}$—, $R^5$—C(O)—O—, $R^{15}$—O—C(O)—, $R^{15}$—C(O)—S—, $R^{15}$—S—C(O)—, $R^{11}$—C(O)—N($R^2$)—, $R^{13}$—N($R^2$)—C(O)—, $R^{15}$—C(S)—O—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^5$—O—C(O)—O—, $R^{15}$—O—C(O)—S—, $R^{15}$—S—C(O)—, $R^{12}$—O—C(O)—N($R^2$)—, $R^8$—N($R^2$)—C(O)—O—, $R^5$—O—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—N($R^2$)—, $R^{15}$—N($R^2$)—C(O)—S—, $R^{15}$—S—C(S)—S—, $R^5$—N($R^2$)—C(O)—N($R^2$)—, $R^5$—N($R^2$)—C(S)—N($R^2$)—, $R^{15}$—N($R^2$)—C(S)—S—, $R^{15}$—S—C(S)—N($R^2$)—, $R^5$—NH—C(N($R^2$))—NH—, $R^5$—S(O)$_{0-2}$—N($R^2$)—, and $R^{15}$—N($R^2$)—S(O)$_{0-2}$—N($R^2$)—. However, if $n^1$ is 1 or 2 and $Z^1$ is $R^9$—, $R^{13}$—C(O)—, $R^7$—N($R^2$)—, $R^6$—O—, $R^{10}$—S—, $R^{13}$—S(O)$_{1-2}$—, $R^{15}$—C(O)—O—, $R^{15}$—O—C(O)—, $R^{11}$—C(O)—N($R^2$)—, $R^{13}$—N($R^2$)—C(O)—, $R^{12}$—O—C(O)—N($R^2$)—, $R^8$—N($R^2$)—C(O)—O—, $R^5$—S(O)$_2$—N($R^2$)— or $R^5$—N($R^2$)—S(O)$_2$—, then A is not thienyl, thiadiazolyl, thiazolyl, pyrimidyl, pyrazinyl, pyridazinyl, pyridyl, triazinyl or tetrazinyl.

In certain desirable embodiments according to this aspect of the invention, $Z^1$ is selected from the group consisting of $R^5$—C(O)—O—, $R^{12}$—O—C(O)—N($R^2$)—, $R^{11}$—C(O)—N($R^2$)—, $R^{15}$—C(S)—N($R^2$)—, $R^{15}$—S—C(O)—N($R^2$)—, $R^5$—N($R^2$)—C(O)—N($R^2$), $R^5$—N($R^2$)—C(S)—N($R^2$)—, $R^8$—N($R^2$)—C(O)—O—, $R^{15}$—O—C(S)—N($R^2$)—, $R^{15}$—S—C(S)—N($R^2$)—, $R^5$—N($R^2$)—C(S)—O—, $R^5$—O—C(S)—N($R^2$)—, $R^5$—S(O)$_{0-2}$—N($R^2$)— or $R^5$—N($R^2$)—S(O)$_{0-2}$—. Preferably, $Z^1$ is $R^5$—C(O)—O—, $R^{12}$—O—C(O)—N($R^2$)—, $R^{11}$—C(O)—N($R^2$)—, $R^5$—N($R^2$)—C(O)—N($R^2$), $R^5$—N($R^2$)—C(S)—N($R^2$)—, $R^8$—N($R^2$)—C(O)—O—, $R^5$—N($R^2$)—C(S)—O—, $R^5$—O—C(S)—N($R^2$)—, $R^6$—O— or $R^7$—N($R^2$)—. For example, $Z^1$ may be $R^{12}$—O—C(O)—N($R^2$)—, ($C_1$-$C_6$ hydrocarbyl)-O—($C_1$-$C_6$ hydrocarbyl)-O—C(O)—N($R^2$)—, ($C_1$-$C_6$ hydrocarbyl)-O—C(O)—N($R^2$)—, or $R^{16}$—O—C(O)—N($R^2$)—, in which $R^{16}$ is optionally-substituted ($C_1$-$C_6$ hydrocarbyl)-, optionally substituted Ar—($C_1$-$C_2$ hydrocarbyl)-, optionally substituted Het-($C_1$-$C_2$ hydrocarbyl)-, optionally substituted Hca-($C_0$-$C_2$ hydrocarbyl)- or optionally substituted Cak-($C_0$-$C_2$ hydrocarbyl).

According to another aspect of the invention, in compounds of formula (1) X has the structure

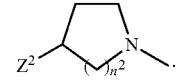

In this aspect of the invention, $n^2$ is 0 or 2-4. In certain desirable embodiments of the invention, $n^2$ is 2. In other embodiments of the invention, $n^2$ is 0 or 3-4. When $n^2$ is 0, 3 or 4, the compound may have (S)-stereochemical configuration, have (R)-stereochemical configuration, or exist as a racemic or scalemic mixture, at the carbon to which $Z^2$ is attached.

In this aspect of the invention, $Z^2$ is selected from the group consisting of $R^{15}$—, $R^{15}$—C(O)—, $R^{15}$—C(S)—, $R^{15}$—N($R^2$)—, $R^{15}$—O—, $R^{15}$—S—, $R^{15}$—S(O)$_{1-2}$, $R^{15}$—C(O)—O—, $R^{15}$—O—C(O)—, $R^{15}$—C(O)—S—, $R^{15}$—S—C(O)—, $R^{15}$—C(O)—N($R^2$)—, $R^{15}$—N($R^2$)—C(O)—, $R^{15}$—C(S)—O—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^{15}$—O—C(S)—O—, $R^{15}$—O—C(O)—S—, $R^{15}$—S—C(O)—O—, $R^{15}$—O—C(O)—N($R^2$)—, $R^{15}$—N($R^2$)—C(O)—O—, $R^{15}$—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0-2}$—N($R^2$)—, $R^{15}$—N($R^2$)—S(O)$_{1-2}$— and $R^{15}$—N($R^2$)—S(O)$_{0-2}$—N($R^2$)—. However, if n2 is 2 and $Z^2$ is $R^{15}$—, $R^{15}$—C(O)—, $R^{15}$—N($R^2$)—, $R^{15}$—O—, $R^{15}$—S—, $R^{15}$—S(O)$_{1-2}$, $R^{15}$—C(O)—O—, $R^{15}$—O—C(O)—, $R^{15}$—C(O)—N($R^2$)—, $R^{15}$—N($R^2$)—C(O)—, $R^{15}$—O—C(O)—N($R^2$)—, $R^{15}$—N($R^2$)—C(O)—O—, $R^{15}$—S(O)$_2$—N($R^2$)— or $R^{15}$—N($R^2$)—S(O)$_2$—, then A is not thienyl, thiadiazolyl, thiazolyl, pyrimidyl, pyrazinyl, pyridazinyl, pyridyl, triazinyl or tetrazinyl.

In certain desirable embodiments according to this aspect of the invention, $Z^2$ is $R^{15}$—C(O)—, $R^{15}$—O—C(O)—N $R^{15}$—N($R^2$)—C(O)—N($R^2$)—, $R^{15}$—C(O)—N($R^2$)—, $R^5$—N($R^2$)—C(O)—N($R^2$), $R^{15}$—N($R^2$)—C(S)—N($R^2$)—, $R^{15}$—N($R^2$)—C(O)—O—, $R^{15}$—N($R^2$)—C(S)—O—, $R^{15}$—O—C(S)—N($R^2$)—, $R^{15}$—O— or $R^{15}$—N($R^2$)—.

According to another aspect of the invention, in compounds of formula (1) X has the structure

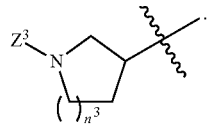

In this aspect of the invention, $n^3$ is 0-4. In certain desirable embodiments of the invention, $n^3$ is 1 or 2. In other embodiments of the invention, $n^3$ is 0 or 3-4. When $n^3$ is 1-4, the compound may have (S)-stereochemical configuration, have (R)-stereochemical configuration, or exist as a racemic or scalemic mixture, at the carbon to which the carbonyl moiety is attached.

In this aspect of the invention, $Z^3$ is selected from the group consisting of $R^{15}$—, $R^{15}$—C(O)—, $R^{15}$—C(S)—, $R^{15}$—N($R^2$)—, $R^{15}$—O—, $R^{15}$—S—, $R^{15}$—S(O)$_{1-2}$, $R^{15}$—C(O)—O—, $R^{15}$—O—C(O)—, $R^{15}$—C(O)—S—, $R^{15}$—S—C(S)—, $R^{15}$—C(O)—N($R^2$)—, —, $R^{15}$—N($R^2$)—C(O)—, $R^{15}$—C(S)—O—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^{15}$—O—C(S)—O—, $R^{15}$—O—C(O)—S—, $R^{15}$—S—C(O)—O—, $R^{15}$—O—C(O)—N($R^2$)—, $R^{15}$—N($R^2$)—C(O)—O—, $R^{15}$—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0-2}$—N($R^2$)—, $R^{15}$—N($R^2$)—S(O)$_{1-2}$— and $R^{15}$—N($R^2$)—S(O)$_{0-2}$—N($R^2$)—. However, if $n^3$ is 2 and $Z^3$ is $R^{15}$—, $R^{15}$—C(O)—, $R^{15}$—N($R^2$)—, $R^{15}$—O—, $R^{15}$—S—, $R^{15}$—S(O)$_{1-2}$, $R^{15}$—C(O)—O—, $R^{15}$—O—C(O)—, $R^{15}$—C(O)—N($R^2$)—, $R^{15}$—N($R^2$)—C(O)—, $R^{15}$—O—C(O)—N($R^2$)—, $R^{15}$—N($R^2$)—C(O)—O—, $R^{15}$—S(O)$_2$—N($R^2$)— or $R^{15}$—N($R^2$)—S(O)$_2$— then A is not phenyl, thienyl, thiadiazolyl, thiazolyl, pyrimidyl, pyrazinyl, pyridazinyl, pyridyl, triazinyl or tetrazinyl. In certain embodiments according to this aspect of the invention, $n^3$ is 1 and $Z^3$ is $R^{15}$—, $R^{15}$—C(O)—, $R^{15}$—N($R^2$)—, $R^{15}$—O—, $R^{15}$—S—, $R^{15}$—S(—)$_{1-2}$, $R^{15}$—C(O)—, $R^{15}$—O—C(O)—, $R^{15}$—C(O)—N($R^2$)—, $R^{15}$—N($R^2$)C(O)—, $R^{15}$—O—C(O)—N($R^2$)—, $R^{15}$—N($R^2$)—C(O)—O—, $R^{15}$—S(O)$_2$—N($R^2$)— or $R^{15}$—N($R^2$)—S(O)$_2$— and A is not phenyl, thienyl, thiadiazolyl, thiazolyl, pyrimidyl, pyrazinyl, pyridazinyl, pyridyl, triazinyl or tetrazinyl.

In certain desirable embodiments according to this aspect of the invention, $Z^3$ is $R^{15}$—C(O)—, $R^5$—O—C(O)—N($R^2$)—, $R^{15}$—C(O)—N($R^2$)—, $R^{15}$—N($R^2$)—C(O)—N($R^2$), $R^{15}$—N($R^2$)—C(S)—N($R^2$)—, $R^{15}$—N($R^2$)—C(O)—O—, $R^{15}$—N($R^2$)—C(S)—O—, $R^{15}$—O—C(S)—N($R^2$)—, $R^{15}$—O— or $R^{15}$—N($R^2$)—.

According to another aspect of the invention, in compounds of formula (1) X has the structure

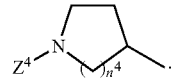

In this aspect of the invention, n4 is 0 or 2-4. In certain desirable embodiments of the invention, n2 is 2. In other embodiments of the invention, n2 is 0 or 3-4. When n4 is 0, 3 or 4, the compound may have (S)-stereochemical configuration, have (R)-stereochemical configuration, or exist as a racemic or scalemic mixture, at the carbon to which the carbonyl moiety is attached.

In this aspect of the invention, $Z^4$ is selected from the group consisting of $R^{15}$—, $R^{15}$—C(O)—, $R^{15}$—C(S)—, $R^{15}$—N($R^2$)—, $R^{15}$—O—, $R^{15}$—S—, $R^{15}$—S(O)$_{1-2}$, $R^{15}$—C(O)—O—, $R^{15}$—O—C(O)—, $R^{15}$—C(O)—S—, $R^{15}$—S—C(S)—, $R^{15}$—C(O)—N($R^2$)—, $R^{15}$—N($R^2$)—C(O)—, $R^{15}$—C(S)—O—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^{15}$—O—C(S)—O—, $R^{15}$—O—C(O)—S—, $R^{15}$—S—C(O)—O—, $R^{15}$—O—C(O)—N($R^2$)—, $R^{15}$—N($R^2$)—C(O)—O—, $R^{15}$—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0-2}$—N($R^2$)—, $R^{15}$—N($R^2$)—S(O)$_{1-2}$— and $R^{15}$—N($R^2$)—S(O)$_{0-2}$—N($R^2$)—. However, if $n^4$ is 2 and $Z^4$ is $R^{15}$—, $R^{15}$—C(O)—, $R^{15}$—N($R^2$)—, $R^{15}$—O—, $R^{15}$—S—, $R^{15}$—S(O)$_{1-2}$, $R^{15}$—C(O)—O—, $R^{15}$—O—C(O)—O—, $R^{15}$—C(O)—N($R^2$)—, $R^{15}$—N($R^2$)—C(O)—, $R^{15}$—O—C(O)—N($R^2$)—, $R^{15}$—N($R^2$)—C(O)—O—, $R^{15}$—S(O)$_2$—N($R^2$)— or $R^{15}$—N($R^2$)—S(O)$_2$— then A is not phenyl, thienyl, thiadiazolyl, thiazolyl, pyrimidyl, pyrazinyl, pyridazinyl, pyridyl, triazinyl or tetrazinyl.

In certain desirable embodiments according to this aspect of the invention, $Z^4$ is $R^{15}$—C(O)—, $R^5$—O—C(O)—N($R^2$)—, $R^{15}$—C(O)—N($R^2$)—, $R^5$—N($R^2$)—C(O)—N($R^2$), $R^{15}$—N($R^2$)—C(S)—N($R^2$)—, $R^{15}$—N($R^2$)—C(O)—O—, $R^{15}$—N($R^2$)—C(S)—O—, $R^{15}$—O—C(S)—N($R^2$)—, $R^{15}$—O— or $R^{15}$—N($R^2$)—.

According to another aspect of the invention, in compounds of formula (1) X has the structure

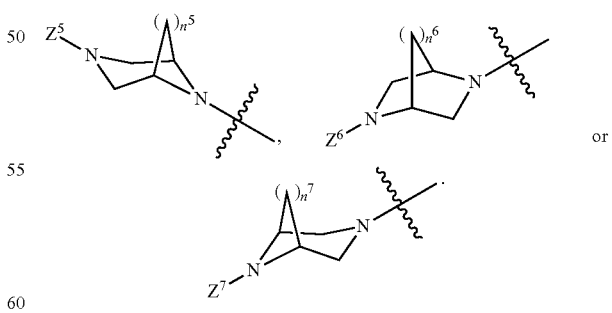

In this aspect of the invention, $n^5$ is 1-4. In certain desirable embodiments of the invention, $n^5$ is 1 or 2.
In this aspect of the invention, $n^6$ is 1-4. In certain desirable embodiments of the invention, $n^6$ is 1 or 2.
In this aspect of the invention, $n^7$ is 1-4. In certain desirable embodiments of the invention, $n^7$ is 1 or 2.

In this aspect of the invention, $Z^5$ is selected from the group consisting of $R^{15}$—, $R^{15}$—C(O)—, $R^{15}$—C(S)—, $R^{15}$—N($R^2$)—, $R^{15}$—O—, $R^{15}$—S—, $R^{15}$—S(O)$_{1-2}$, $R^{15}$—C(O)—O—, $R^{15}$—O—C(O)—, $R^{15}$—C(O)—S—, $R^{15}$—S—C(O)—, $R^{15}$—C(O)—N($R^2$)—, $R^{15}$—N($R^2$)—C(O)—, $R^{15}$—C(S)—O—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^{15}$—O—C(O)—O—, $R^{15}$—O—C(O)—S—, $R^{15}$—S—C(O)—O—, $R^{15}$—O—C(O)—N($R^2$)—, $R^{15}$—N($R^2$)—C(O)—O—, $R^{15}$—O—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0-2}$—N($R^2$)—, $R^{15}$—N($R^2$)—S(O)$_{1-2}$— and $R^{15}$—N($R^2$)—S(O)$_{0-2}$—N($R^2$)—. In certain desirable embodiments according to this aspect of the invention, $Z^5$ is $R^{15}$—C(O)—O—, $R^{15}$—O—C(O)—N($R^2$)—, $R^{15}$—C(O)—N($R^2$)—, $R^{15}$—N($R^2$)—C(O)—N($R^2$), $R^5$—N($R^2$)—C(S)—N($R^2$), $R^{15}$—N($R^2$)—C(O)—O—, $R^{15}$—N($R^2$)—C(S)—O—, $R^{15}$—O—C(S)—N($R^2$)—, $R^{15}$—O— or $R^{15}$—N($R^2$)—.

In this aspect of the invention, $Z^6$ is selected from the group consisting of $R^{15}$—, $R^{15}$—C(O)—, $R^{15}$—C(S)—, $R^{15}$—N($R^2$)—, $R^{15}$—O—, $R^{15}$—S—, $R^{15}$—S(O)$_{1-2}$, $R^{15}$—C(O)—O—, $R^{15}$—O—C(O)—, $R^{15}$—C(O)—S—, $R^{15}$—S—C(O)—, $R^{15}$—C(O)—N($R^2$)—, $R^{15}$—N($R^2$)—C(O)—, $R^{15}$—C(S)—O—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^{15}$—O—C(S)—O—, $R^{15}$—O—C(O)—S—, $R^{15}$—S—C(O)—O—, $R^{15}$—O—C(O)—N($R^2$)—, $R^{15}$—N($R^2$)—C(O)—O—, $R^{15}$—OC(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0-2}$—N($R^2$)—, $R^{15}$—N($R^2$)—S(O)$_{1-2}$— and $R^{15}$—N($R^2$)—S(O)$_{0-2}$—N($R^2$)—. In certain desirable embodiments according to this aspect of the invention, $Z^6$ is $R^{15}$—C(O)—O—, $R^{15}$—O—C(O)—N($R^2$)—, $R^{15}$—C(O)—N($R^2$)—, $R^{15}$—N($R^2$)—C(O)—N($R^2$), $R^5$—N($R^2$)—C(S)—N($R^2$), $R^{15}$—N($R^2$)—C(O)—O—, $R^{15}$—N($R^2$)—C(S)—O—, $R^{15}$—O—C(S)—N($R^2$)—, $R^{15}$—O— or $R^{15}$—N($R^2$)—.

In this aspect of the invention, $Z^7$ is selected from the group consisting of $R^{15}$—, $R^{15}$—C(O)—, $R^{15}$—C(S)—, $R^{15}$—N($R^2$)—, $R^{15}$—O—, $R^{15}$—S—, $R^{15}$—S(O)$_{1-2}$, $R^{15}$—C(O)—O—, $R^{15}$—O—C(O)—, $R^{15}$—C(O)—, $R^{15}$—S—C(S)—, $R^{15}$—C(O)—N($R^2$)—$R^{15}$—N($R^2$)—C(S), $R^{15}$—C(S)—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^{15}$—O—C(S)—O—, $R^{15}$—O—C(O)—S—, $R^{15}$—S—C(O)—O—, $R^{15}$—O—C(O)—N($R^2$)—, $R^{15}$—N($R^2$)—C(O)—O—, $R^{15}$—OC(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^5$—S(O)$_{0-2}$—N($R^2$)—, $R^{15}$—N($R^2$)—S(O)$_{1-2}$— and $R^{15}$—N($R^2$)—S(O)$_{0-2}$—N($R^2$)—. In certain desirable embodiments according to this aspect of the invention, $Z^6$ is $R^{15}$—C(O)—O—, $R^{15}$—O—C(O)—N($R^2$)—, $R^{15}$—C(O)—N($R^2$)—, $R^{15}$—N($R^2$)—C(O)—N($R^2$), $R^{15}$—N($R^2$)—C(S)—N($R^2$), $R^{15}$—N($R^2$)—C(O)—O—, $R^{15}$—N($R^2$)—C(S)—O—, $R^{15}$—O—C(S)—N($R^2$)—, $R^{15}$—O— or $R^{15}$—N($R^2$)—.

According to another aspect of the invention, in compounds of formula (1) X has the structure

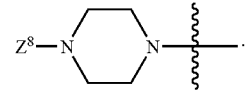

In this aspect of the invention, $Z^8$ is selected from the group consisting of $R^{15}$—, $R^{15}$—C(O)—, $R^{15}$—C(S)—, $R^{15}$—N($R^2$)—, $R^{15}$—O—, $R^{15}$—S—, $R^{15}$—S(O)$_{1-2}$, $R^{15}$—C(O)—O—, $R^{15}$—O—C(O)—, $R^{15}$—C(O)—S—, $R^{15}$—S—C(S)—, $R^{15}$—C(O)—N($R^2$)—, $R^{15}$—N($R^2$)—C(O)—, $R^{15}$—C(S)—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^{15}$—O—C(S)—O—, $R^{15}$—O—C(O)—S—, $R^{15}$—S—C(O)—O—, $R^{15}$—O—C(O)—N($R^2$)—, $R^{15}$—N($R^2$)—C(O)—O—, $R^{15}$—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0-2}$—N($R^2$)—, $R^{15}$—N($R^2$)—S(O)$_{1-2}$— and $R^{15}$—N($R^2$)—S(O)$_{0-2}$—N($R^2$)—. However, if $Z^8$ is $R^{15}$—, $R^{15}$—C(O)—, $R^{15}$—N($R^2$)—, $R^{15}$—O—, $R^{15}$—S—, $R^{15}$—S(O)$_{1-2}$, $R^{15}$—C(O)—O—, $R^{15}$—C(O)—, $R^{15}$—C(O)—N($R^2$)—, $R^{15}$—N($R^2$)—C(O)—, $R^{15}$—O—C(O)—N($R^2$)—, $R^{15}$—N($R^2$)—C(O)—O—, $R^{15}$—S(O)$_2$—N($R^2$)— or $R^{15}$—N($R^2$)—S(O)$_2$— then A is not phenyl, thienyl, thiadiazolyl, thiazolyl, pyrimidyl, pyrazinyl, pyridazinyl, pyridyl, triazinyl or tetrazinyl.

In certain desirable embodiments according to this aspect of the invention, $Z^8$ is $R^5$—C(O)—, $R^5$—O—C(O)—N($R^2$)—, $R^{15}$—C(O)—N($R^2$)—, $R^5$—N($R^2$)—C(O)—N($R^2$), $R^{15}$—N($R^2$)—C(S)—N($R^2$)—, $R^{15}$—N($R^2$)—C(O)—O—, $R^{15}$—N($R^2$)—C(S)—O—, $R^{15}$—O—C(S)—N($R^2$)—, $R^{15}$—O— or $R^{15}$—N($R^2$)—.

In the compounds of formula (1), each $R^2$ is independently selected from the group consisting of hydrogen, ($C_1$-$C_5$ alkyl)-, Ar—($C_0$-$C_4$ alkyl)-, Het-($C_0$-$C_4$ alkyl)-, Hca-($C_0$-$C_4$ alkyl)-, Cak-($C_0$-$C_4$ alkyl)-, $R^{14}$—CO—, $R^{14}$—SO$_2$—, $R^{14}$—CO—NH— and $R^{14}$—CO—O— in which each alkyl, Ar, Het, Hca and Cak is optionally substituted.

In the compounds of formula (1), each $R^5$ is independently selected from the group consisting of H—, ($C_1$-$C_6$ hydrocarbyl)-, Ar—($C_1$-$C_6$ hydrocarbyl)-, Het-($C_1$-$C_6$ hydrocarbyl)-, Hca-($C_0$-$C_6$ hydrocarbyl)- and Cak-($C_0$-$C_6$ hydrocarbyl)-, wherein any ($C_1$-$C_6$ hydrocarbyl)-moiety, Ar, Het, Hca and Cak is optionally substituted.

In the compounds of formula (1), each $R^6$ is independently selected from the group consisting of H—, optionally substituted ($C_1$-$C_6$ hydrocarbyl)- with the proviso that if the ($C_1$-$C_6$ hydrocarbyl)- has only one substituent, it is not halo or amino, Hca-($C_0$-$C_1$ or $C_3$-$C_6$ hydrocarbyl)- and Cak-($C_0$-$C_6$ hydrocarbyl)-, wherein any ($C_1$hydrocarbyl)-, $C_3$-$C_6$ hydrocarbyl moiety, —($C_1$-$C_6$ hydrocarbyl)-moiety, Hca and Cak is optionally substituted.

In the compounds of formula (1), each $R^7$ is independently selected from the group consisting of H, ($C_1$-$C_6$ hydrocarbyl)-, Hca-($C_0$-$C_1$ or $C_3$-$C_6$ hydrocarbyl)- and Cak-($C_0$-$C_6$ hydrocarbyl)-, wherein any ($C_1$-$C_6$ hydrocarbyl)-moiety, ($C_1$ hydrocarbyl)-, $C_3$-$C_6$ hydrocarbyl moiety, Hca and Cak is optionally substituted.

In the compounds of formula (1), each $R^8$ is independently selected from the group consisting of ($C_1$-$C_6$ hydrocarbyl)-, Ar—($C_1$-$C_6$ hydrocarbyl) -, Het-($C_1$-$C_6$ hydrocarbyl)-, Hca-($C_0$-$C_6$ hydrocarbyl)- and Cak-($C_0$-$C_6$ hydrocarbyl) -, wherein any ($C_1$-$C_6$ hydrocarbyl)-moiety, Ar, Het, Hca and Cak is optionally substituted with the proviso that $R^8$ is not 2(morpholin-4-yl)ethyl.

In the compounds of formula (1), each $R^9$ is independently selected from the group consisting of Hca-($C_0$-$C_6$ hydrocarbyl)- and Cak-($C_0$-$C_6$ hydrocarbyl)-, wherein any ($C_1$-$C_6$ hydrocarbyl)-moiety, Hca and Cak is optionally substituted.

In the compounds of formula (1), each $R^{10}$ is independently selected from the group consisting of H—, Hca-($C_0$-$C_6$ hydrocarbyl)- and Cak-($C_0$-$C_6$ hydrocarbyl)-, wherein any ($C_1$-$C_6$ hydrocarbyl)-moiety, Hca and Cak is optionally substituted.

In the compounds of formula (1), each $R^{11}$ is independently selected from the group consisting of H—, ($C_1$-$C_6$ hydrocarbyl)-, Hca-($C_0$-$C_6$ hydrocarbyl)- and Cak-($C_0$-$C_6$ hydrocarbyl)-, wherein any ($C_1$-$C_6$ hydrocarbyl)-moiety, Hca and Cak is optionally substituted.

In the compounds of formula (1), each $R^{12}$ is independently selected from the group consisting of ($C_1$-$C_6$ hydrocarbyl)-, Ar—($C_1$-$C_6$ hydrocarbyl) -, Het-($C_1$-$C_6$ hydrocarbyl)-, Hca-($C_0$-$C_6$ hydrocarbyl)-, Cak-($C_0$-$C_6$ hydrocarbyl) -, wherein any ($C_1$-$C_6$ hydrocarbyl)-moiety, Ar, Het, Hca and Cak is optionally substituted.

In the compounds of formula (1), each $R^{13}$ is independently selected from the group consisting of H—, ($C_1$-$C_6$ hydrocarbyl)-, Hca-($C_0$-$C_6$ hydrocarbyl)- and Cak-($C_0$-$C_6$ hydrocarbyl)-, wherein any ($C_1$-$C_6$ hydrocarbyl)-moiety, Hca and Cak is optionally substituted.

In the compounds of formula (1), each $R^{14}$ is independently selected from the group consisting of optionally substituted Ar— and optionally substituted ($C_1$-$C_6$ hydrocarbyl)-.

In the compounds of formula (1), each $R^{15}$ is independently selected from the group consisting of H—, ($C_1$-$C_6$ hydrocarbyl)-, Ar—($C_0$-$C_6$ hydrocarbyl)-, Het-($C_0$-$C_6$ hydrocarbyl)-, Hca-($C_0$-$C_6$ hydrocarbyl)- and Cak-($C_0$-$C_6$ hydrocarbyl) -, wherein any ($C_1$-$C_6$ hydrocarbyl)-moiety, Ar, Het, Hca and Cak is optionally substituted.

In a preferred embodiment of the compounds according to the present invention,

T is —$NH_2$;

A is phenyl; and

X is

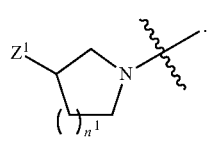

In a preferred embodiment of the compounds according to the present invention,

T is —$NH_2$;

A is phenyl; and

X is

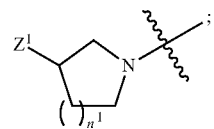

wherein $n^1$=1 and $Z^1$ is selected from the group consisting of $R^7$—N($R^2$)—, $R^6$—O—, $R^{11}$—C(O)—N($R^2$)—, $R^{15}$—C(S)—N($R^2$)—, $R^{12}$—O—C(O)—N($R^2$)—, $R^8$—N($R^2$)—C(O)—O—, $R^{15}$—N($R^2$)—C(S)—O—, $R^5$—N($R^2$)—C(O)—N($R^2$)—, $R^5$—N($R^2$)—C(S)—N($R^2$)—, $R^{15}$—O—C(S)—N($R^2$)— and $R^5$—S(O)$_{0-2}$—N($R^2$)—.

In a preferred embodiment of the compounds according to the present invention,

T is —$NH_2$;

A is phenyl; and

X is

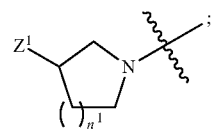

wherein $n^1$=1 and $Z^1$ is selected from the group consisting of $R^7$—N($R^2$)—, $R^6$—O—, $R^{11}$—C(O)—N($R^2$)—, $R^{15}$—C(S)—N($R^2$)—, $R^{12}$—O—C(O)—N($R^2$)—, $R^8$—N($R^2$)—C(O)—O—, $R^{15}$—N($R^2$)—C(S)—O—, $R^5$—N($R^2$)—C(O)—N($R^2$)—, $R^5$—N($R^2$)—C(S)—N($R^2$)—, $R^{15}$—O—C(S)—N($R^2$)— and $R^5$—S(O)$_{0-2}$—N($R^2$)—;

wherein $R^2$ is H, optionally substituted ($C_1$-$C_5$ alkyl)-, or optionally substituted Het-($C_0$-$C_4$ alkyl)-, preferably H;

$R^5$ is optionally substituted Het-($C_1$-$C_6$ hydrocarbyl)-;

$R^6$ is H;

$R^7$ is H or optionally substituted ($C_1$-$C_6$ hydrocarbyl)-;

$R^8$ is optionally substituted ($C_1$-$C_6$ hydrocarbyl)-;

$R^{11}$ is optionally substituted Hca-($C_0$-$C_6$ hydrocarbyl)- or optionally substituted ($C_1$-$C_6$ hydrocarbyl)-;

$R^{12}$ is ($C_1$-$C_6$ hydrocarbyl)-, Ar—($C_1$-$C_6$ hydrocarbyl) -, Het-($C_1$-$C_6$ hydrocarbyl)-, Hca-($C_0$-$C_6$ hydrocarbyl)- or Cak-($C_0$-$C_6$ hydrocarbyl)-, each of which is optionally substituted; and $R^{15}$ is optionally substituted ($C_1$-$C_6$ hydrocarbyl)- or optionally substituted Hca-($C_0$-$C_6$ hydrocarbyl) -.

In a preferred embodiment of the compounds according to the present invention,

T is —$NH_2$;

A is phenyl; and

X is

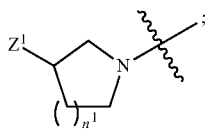

wherein
n$^1$=1 and
Z$^1$ is selected from the group consisting of R$^7$—N(R$^2$)—, R$^{11}$—C(O)—N(R$^2$)— and R$^{12}$—O—C(O)—N(R$^2$)—.

In a preferred embodiment of the compounds according to the present invention,
T is —NH$_2$;
A is phenyl; and
X is

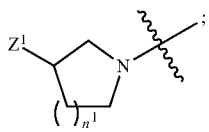

wherein
n$^1$=1 and
Z$^1$ is selected from the group consisting of R$^7$—N(R$^2$)—, R$^{11}$—C(O)—N(R$^2$)— and R$^{12}$—O—C(O)—N(R$^2$)—; wherein
R$^2$ is H, optionally substituted (C$_1$-C$_5$ alkyl)-, or optionally substituted Het-(C$_0$-C$_4$ alkyl)-, preferably H;
R$^7$ is H or optionally substituted (C$_1$-C$_6$ hydrocarbyl)-;
R$^{11}$ is optionally substituted Hca-(C$_0$-C$_6$ hydrocarbyl)- or optionally substituted (C$_1$-C$_6$ hydrocarbyl)-; and
R$^{12}$ is (C$_1$-C$_6$ hydrocarbyl)-, Ar—(C$_1$-C$_6$ hydrocarbyl)-, Het-(C$_1$-C$_6$ hydrocarbyl)-, Hca-(C$_0$-C$_6$ hydrocarbyl)- or Cak-(C$_0$-C$_6$ hydrocarbyl)-, each of which is optionally substituted.

In a preferred embodiment of the compounds according to the present invention,
T is —NH$_2$;
A is phenyl; and
X is

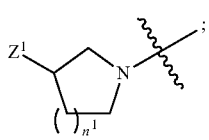

wherein
n$^1$=1 and
Z$^1$ is R$^{12}$—O—C(O)—N(R$^2$)—; wherein
R$^2$ is H or optionally substituted Het-(C$_0$-C$_4$ alkyl)-, preferably H; and
R$^{12}$ is (C$_1$-C$_6$ hydrocarbyl)-, Ar—(C$_1$-C$_6$ hydrocarbyl)-, Het-(C$_1$-C$_6$ hydrocarbyl)-, Hca-(C$_0$-C$_6$ hydrocarbyl)- or Cak-(C$_0$-C$_6$ hydrocarbyl)-, preferably (C$_1$-C$_6$ hydrocarbyl)-, each of which is optionally substituted.

In a preferred embodiment of the compounds according to the present invention,
T is —NH$_2$;
A is phenyl; and
X is

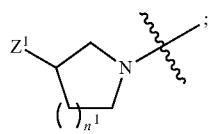

wherein
n$^1$=1 and
Z$^1$ is R$^{12}$—O—C(O)—N(R$^2$)—; wherein
R$^2$ is H or optionally substituted Het-(C$_0$-C$_4$ alkyl)-, preferably H; and
R$^{12}$ is (C$_1$-C$_6$ hydrocarbyl)-, Ar—(C$_1$-C$_6$ hydrocarbyl)-, Het-(C$_1$-C$_6$ hydrocarbyl)-, Hca-(C$_0$-C$_6$ hydrocarbyl)- or Cak-(C$_0$-C$_6$ hydrocarbyl)-, preferably (C$_1$-C$_6$ hydrocarbyl)-, each of which is optionally substituted with a substituent selected from the group consisting of alkyl, amino, alkylamino, di-alkylamino, alkoxy, —CF$_3$ and halo.

In a preferred embodiment of the compounds according to the present invention,
T is —NH$_2$;
A is phenyl; and
X is

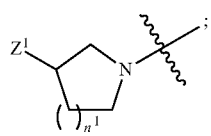

wherein
n$^1$=1 and
Z$^1$ is R$^{12}$—O—C(O)—N(R$^2$)—; wherein
R$^2$ is H or optionally substituted Het-(C$_0$-C$_4$ alkyl)-, preferably H; and
R$^{12}$ is (C$_1$-C$_6$ hydrocarbyl)- optionally substituted with a substituent selected from the group consisting of alkyl, amino, alkylamino, di-alkylamino, alkoxy, —CF$_3$ and halo.

In a preferred embodiment of the compounds according to the present invention,
T is —NH$_2$;
A is phenyl; and
X is

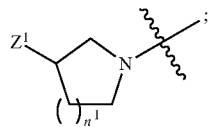

wherein
n$^1$=1 and
Z$^1$ is R$^7$—N(R$^2$)—; wherein
R$^2$ is optionally substituted Het-(C$_0$-C$_4$ alkyl)-; and
R$^7$ is H or optionally substituted (C$_1$-C$_6$ hydrocarbyl)-.

In the definitions of R$^2$ and R$^5$-R$^{15}$ above, each Ar is independently an optionally substituted aryl, each Het is independently an optionally substituted heteroaryl, each Hca is inde-

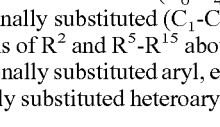

pendently an optionally substituted heterocycloalkyl, and each Cak is independently an optionally substituted cycloalkyl.

In a preferred embodiment of the present invention the compound is selected from the group consisting of
(S)-2-(Dimethylamino)ethyl-1-(4-(2-aminophenylcarbamoyl) -phenyl)pyrrolidin-3-ylcarbamate;
(S)-Methyl 1-(4-(2-aminophenylcarbamoyl)phenyl)pyrrolidin-3-yl carbamate;
(S)-Ethyl 1-(4-(2-aminophenylcarbamoyl)phenyl)pyrrolidin-3-yl carbamate;
(S)-tert-Butyl 1-(4-(2-aminophenylcarbamoyl)phenyl)pyrrolidin-3-yl carbamate;
(S)-Isobutyl 1-(4-(2-aminophenylcarbamoyl)phenyl)pyrrolidin-3-yl carbamate;
(S)-Benzyl 1-(4-(2-aminophenylcarbamoyl)phenyl)pyrrolidin-3-yl carbamate;
(S)-N-(1-(4-(2-Aminophenylcarbamoyl)phenyl)pyrrolidin-3-yl)morpholine-4-carboxamide;
((S)-Pyridin-3-ylmethyl-1-(4-(2-aminophenylcarbamoyl)phenyl)pyrrolidin-3-yl carbamate;
(S)-N-(2-Aminophenyl)-4-(3-(3-(pyridin-3-ylmethyl)ureido)pyrrolidin-1-yl)benzamide;
(S)-2-Methoxyethyl-1-(4-(2-aminophenylcarbamoyl)phenyl)pyrrolidin-3-yl carbamate;
(R)-2-Methoxyethyl 1-(5-(2-aminophenylcarbamoyl)pyridin-2-yl)pyrrolidin-3-yl carbamate;
(S)-N-(2-Aminophenyl)-4-(3-(3-(pyridin-3-ylmethyl)thioureido)pyrrolidin-1-yl)benzamide;
(S)-O-Methyl 1-(4-(2-aminophenylcarbamoyl)phenyl)pyrrolidin-3-ylcarbamothioate;
(S)-2,2,2-Trifluoroethyl 1-(4-(2-aminophenylcarbamoyl)phenyl) -pyrrolidin-3-ylcarbamate;
(S)-N-(2-Aminophenyl)-4-(3-(2-(dimethylamino)acetamido) pyrrolidin-1-yl)benzamide;
(S)-Pyridin-4-ylmethyl 1-(4-(2-aminophenyl carbamoyl)phenyl)pyrrolidin-3-yl carbamate;
(S)-Pyridin-2-ylmethyl 1-(4-(2-aminophenyl carbamoyl)phenyl)pyrrolidin-3-yl carbamate;
(S)-3-(Dimethyl amino)propyl 1-(4-(2-amino phenylcarbamoyl)phenyl)pyrrolidin-3-yl carbamate;
(S)-Furan-3-ylmethyl 1-(4-(2-aminophenylcarbamoyl)phenyl) pyrrolidin-3-yl carbamate;
(R)-1-Methylpyrrolidin-3-yl (S)-1-(4-(2-aminophenylcarbamoyl)phenyl)pyrrolidin-3-yl carbamate;
(S)-1-(4-(2-Aminophenylcarbamoyl)phenyl)pyrrolidin-3-yl acetate;
(S)-N-(2-Aminophenyl)-4-(3-hydroxypyrrolidin-1-yl)benzamide;
(S)-1-(4-(2-Aminophenylcarbamoyl)phenyl)pyrrolidin-3-yl ethyl carbamate;
(S)-O-1-(4-(2-Aminophenylcarbamoyl)phenyl)pyrrolidin-3-yl 2-morpholinoethylcarbamothioate;
(S)-N-(2-Aminophenyl)-4-(3-(dimethylamino)pyrrolidin-1-yl)benzamide;
(S)-N-(2-Aminophenyl)-4-(3-(phenylmethylsulfonamido) pyrrolidin-1-yl)benzamide;
(S)-2-morpholinoethyl 1-(4-(2-aminophenylcarbamoyl)phenyl)pyrrolidin -3-ylcarbamate;
(S)-methyl 1-(4-(2-aminophenylcarbamoyl)phenyl)pyrrolidin-3-yl(pyridin-3-ylmethyl)carbamate;
(S)-benzyl 1-(4-(2-aminophenylcarbamoyl)phenyl)pyrrolidin-3-yl(3,4,5-trimethoxybenzyl)carbamate;
(S)-isopropyl 1-(4-(2-aminophenylcarbamoyl)phenyl)pyrrolidin-3-ylcarbamate;
(S)-cyclopropylmethyl 1-(4-(2-aminophenylcarbamoyl)phenyl)pyrrolidin-3-ylcarbamate;
(S)-tetrahydro-2H-pyran-4-yl 1-(4-(2-aminophenylcarbamoyl)phenyl)pyrrolidin-3-ylcarbamate,
(R)—N-(2-Aminophenyl)-4-(3-hydroxypyrrolidin-1-yl) benzamide,
(S)-N-(2-Aminophenyl)-4-(3-(pyridin-2-ylamino)pyrrolidin-1-yl)benzamide and
(S)-N-(2-aminophenyl)-4-(3-(pyridin-4-ylamino)pyrrolidin-1-yl)benzamide.

In another preferred embodiment of the present invention, the compound is selected from the group consisting of:
(S)-Ethyl 1-(4-(2-aminophenylcarbamoyl)phenyl)pyrrolidin-3-yl carbamate;
(S)-2-Methoxyethyl-1-(4-(2-aminophenylcarbamoyl)phenyl)pyrrolidin-3-yl carbamate; and
(S)-N-(2-Aminophenyl)-4-(3-(pyridin-2-ylamino)pyrrolidin-1-yl)benzamide.

Throughout the specification, preferred embodiments of one or more chemical groups are identified. Also preferred are combinations of preferred embodiments. It is understood that any and all embodiments of the present invention may be taken in conjunction with any other embodiment to describe additional even more preferred embodiments of the present invention. For example, the invention describes preferred embodiments of group A in the compounds and describes preferred embodiments of group $Z^1$. Thus, as an example, also contemplated as within the scope of the invention are compounds in which preferred examples of group A are as described and in which preferred examples of group $Z^1$ are as described. The invention may be embodied in other specific forms without departing from the spirit or essential attributes thereof. Furthermore, any elements of an embodiment are meant to be combined with any and all other elements from any of the embodiments to describe additional embodiments.

Some compounds of the invention may have chiral centers and/or geometric isomeric centers (E- and Z-isomers), and it is to be understood that the invention encompasses all such optical, enantiomeric, diastereoisomeric and geometric isomers. The invention also comprises all tautomeric forms of the compounds disclosed herein. Where compounds of the invention include chiral centers, the invention encompasses the enantiomerically and/or diastereomerically pure isomers of such compounds, the enantiomerically and/or diastereomerically enriched mixtures of such compounds, and the racemic and scalemic mixtures of such compounds. For example, a composition may include a mixture of enantiomers or diastereomers of compound of formula (1) in at least about 30% diastereomeric or enantiomeric excess. In certain embodiments of the invention, the compound is present in at least about 50% enantiomeric or diastereomeric excess, in at least about 80% enantiomeric or diastereomeric excess, or even in at least about 90% enantiomeric or diastereomeric excess. In certain more preferred embodiments of the invention, the compound is present in at least about 95%, even more preferably in at least about 98% enantiomeric or diastereomeric excess, and most preferably in at least about 99% enantiomeric or diastereomeric excess.

The chiral centers of the present invention may have the S or R configuration. The racemic forms can be resolved by physical methods, such as, for example, fractional crystallization, separation or crystallization of diastereomeric derivates or separation by chiral column chromatography. The individual optical isomers can be obtained either starting from chiral precursors/intermediates or from the racemates by any suitable method, including without limitation, conventional methods, such as, for example, salt formation with an optically active acid followed by crystallization.

Another aspect of the invention provides N-oxides, hydrates, solvates, pharmaceutically acceptable salts, complexes and prodrugs of the compounds of formula (1) described above.

The compounds of the present invention form salts which are also within the scope of this invention. Reference to a compound of the formula (1) herein is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic (exhibiting minimal or no undesired toxicological effects), physiologically acceptable) salts are preferred, although other salts are also useful, e.g., in isolation or purification steps which may be employed during preparation. Salts of the compounds of the invention may be formed, for example, by reacting a compound of the present invention with an amount of acid or base, such as an equivalent amount, in a medium such as one in which the salts precipitates or in an aqueous medium followed by lyophilization. In certain cases more than one equivalent of an acid (base) could be used thus providing, for example, di- or tri-salts.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonotes (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl and butyl chlorides, bromides and iodides), dialkyl sulfates (e.g. dimethyl, diethyl, dibutyl and diamyl sulfates), long chain halides (e.g. decyl, lauryl, myristyl and stearyl chlorides, bromides and iodides), aralkyl halides (e.g. benzyl and phenethyl bromides), and others.

As used herein, the term "pharmaceutically acceptable salts" refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, and nitric acid)), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula (—NR)$^+$+Z$^-$, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, or diphenylacetate).

The present invention also includes prodrugs of compounds of the invention. The term "prodrug" is intended to represent a compound covalently bonded to a carrier, which prodrugs are capable of releasing the active ingredient of the prodrug when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the present invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of the invention, amides (e.g., trifluoroacetylamino, acetylamino, and the like), and the like.

The compounds of the invention may be administered in the form of an in vivo hydrolyzable ester or in vivo hydrolyzable amide. An in vivo hydrolyzable ester of a compound of the invention containing carboxy or hydroxy group is, for example, a pharmaceutically acceptable ester which is hydrolyzed in the human or animal body to produce the parent acid or alcohol. Suitable pharmaceutically acceptable esters for carboxy include $C_{1-6}$-alkoxymethyl esters (e.g., methoxymethyl), $C_{1-6}$-alkanoyloxymethyl esters (e.g., for example pivaloyloxymethyl), phthalidyl esters, $C_{3-8}$-cycloalkoxycarbonyloxy$C_{1-6}$-alkyl esters (e.g., 1-cyclohexylcarbonyloxyethyl); 1,3-dioxolen-2-onylmethyl esters (e.g., 5-methyl-1,3-dioxolen-2-onylmethyl; and $C_{1-6}$-alkoxycarbonyloxyethyl esters (e.g., 1-methoxycarbonyloxyethyl) and may be formed at any carboxy group in the compounds of this invention An in vivo hydrolyzable ester of a compound of the invention containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substituents on benzoyl include morpholino and piperazino linked from a ring nitrogen atom via a methylene group to the 3- or 4-position of the benzoyl ring. A suitable value for an in vivo hydrolyzable amide of a compound of the invention containing a carboxy group is, for example, a N—$C_1$-$C_6$alkyl or N,N-di-$C_1$-$C_6$alkyl amide such as N-methyl, N-ethyl, N-propyl, N,N-dimethyl, N-ethyl-N-methyl or N,N-diethyl amide.

Upon administration to a subject, the prodrug undergoes chemical conversion by metabolic or chemical processes to yield a compound of the present invention, or a salt and/or solvate thereof. Solvates of the compounds of the present invention include, for example, hydrates.

The compounds of the present invention may be prepared using the synthetic methods described in the Examples, below. Certain compounds may also be made using methods familiar to the skilled artisan, such as those described in U.S. Patent Application Publication No. 2005/0245518, International Patent Application Publication No. WO 03/092686, and International Patent Application Publication No. WO 03/087057, each of which is hereby incorporated by reference herein.

Another aspect of the invention provides compositions including a compound, N-oxide, hydrate, solvate, pharmaceutically acceptable salt, complex or prodrug of formula (1) as described above, or a racemic mixture, diastereomer, enantiomer or tautomer thereof. For example, in one embodiment of the invention, a composition comprises a compound, N-oxide, hydrate, solvate, pharmaceutically acceptable salt, complex or prodrug of formula (1) present in at least about 30% enantiomeric or diastereomeric excess. In certain desirable embodiments of the invention, the compound, N-oxide, hydrates, solvate, pharmaceutically acceptable salt, complex or prodrug of formula (1) is present in at least about 50%, at least about 80%, or even at least about 90% enantiomeric or diastereomeric excess. In certain other desirable embodiments of the invention, the compound, N-oxide, hydrate, solvate, pharmaceutically acceptable salt, complex or prodrug of formula (1) is present in at least about 95%, more preferably at least about 98% and even more preferably at least about 99% enantiomeric or diastereomeric excess. In other embodiments of the invention, a compound, N-oxide, hydrate, solvate, pharmaceutically acceptable salt, complex or prodrug of formula (1) is present as a substantially racemic mixture.

Another aspect of the invention provides compositions including a compound, N-oxide, hydrate, solvate, pharmaceutically acceptable salt, complex or prodrug thereof, or a racemic mixture, diastereomer, enantiomer or tautomer thereof, having formula (2),

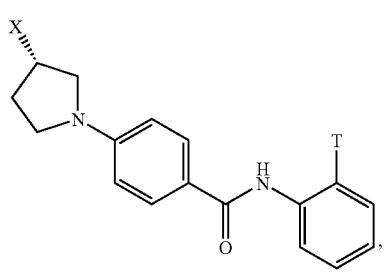

(2)

in which T is $NH_2$ or OH, and X is as described above with respect to formula (1). Compounds of formula (2) have (S)-stereochemical configuration at the carbon to which the X moiety is attached. For example, in one embodiment of the invention, a composition comprises a compound, N-oxide, hydrate, solvate, pharmaceutically acceptable salt, complex or prodrug of formula (2) present in at least about 30% enantiomeric or diastereomeric excess. In certain desirable embodiments of the invention, the compound, N-oxide, hydrate, solvate, pharmaceutically acceptable salt, complex or prodrug of formula (2) is present in at least about 50%, at least about 80%, or even at least about 90% enantiomeric or diasteromeric excess. In certain other desirable embodiments of the invention, the compound, N-oxide, hydrate, solvate, pharmaceutically acceptable salt, complex or prodrug of formula (2) is present in at least about 95%, more preferably at least about 98% and even more preferably at least about 99% enantiomeric or diastereomeric excess.

Pharmaceutical Compositions

Another aspect of the invention provides pharmaceutical compositions comprising a compound, N-oxide, hydrate, solvate, pharmaceutically acceptable salt, complex or prodrug thereof, or a racemic mixture, diastereomer, enantiomer or tautomer thereof, or composition of the invention as described above and in the Examples below, and a pharmaceutically acceptable carrier, excipient, or diluent. The pharmaceutical compositions of the invention may be formulated by any method well known in the art and may be prepared for administration by any route, including, without limitation, parenteral, oral, sublingual, transdermal, topical, intranasal, intratracheal, or intrarectal. In certain preferred embodiments, the pharmaceutical compositions of the invention are administered intravenously in a hospital setting. In certain other preferred embodiments, administration may preferably be by the oral route. The pharmaceutical compositions may be in any form, including but not limited to liquid solutions or suspensions. For oral administration, formulations may be in the form of tablets or capsules. For intranasal administration, the pharmaceutical composition may be in the form of powders, nasal drops, or aerosols. The pharmaceutical compositions may be administered locally or systemically.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., *Remington's Pharmaceutical Sciences*, 18th Edition, ed. A. Gennaro, Mack Publishing Co., Easton, Pa., 1990.

The compound, N-oxide, hydrate, solvate, pharmaceutically acceptable salt, complex, prodrug or mixture, or racemic mixture, diastereomer, enantiomer or tautomer thereof, is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

Depending on the particular condition, or disease, to be treated, additional therapeutic agents, that could be normally administered to treat that condition, or disease, may also be present in the compositions of this invention. Alternatively, administration of such agents may be done sequentially or concurrently with administration of a composition according to the present invention. In other words, compounds of this invention can be administered as the sole pharmaceutical agent or in combination with one or more other additional therapeutic (pharmaceutical) agents where the combination causes no unacceptable adverse effects. This may be of particular relevance for the treatment of hyper-proliferative diseases such as cancer. In this instance, the compound of this invention can be combined with a known anti-cancer agent(s), as well as with admixtures and combinations thereof. As used herein, additional therapeutic agents that are normally administered to treat a particular disease, or condition, are known as "appropriate for the disease, or condition, being treated". As used herein, "additional therapeutic agents" is meant to include, for example, chemotherapeutic agents and other anti-proliferative agents. In certain preferred embodiments of the present invention the composition comprises one or more compound(s) according to the present invention. In certain preferred embodiments of the present invention the composition comprises one or more compound(s) according to the present invention and/or another HDAC inhibitor known in the art or which will be discovered. The active ingredients of such compositions preferably act synergistically to produce a therapeutic effect.

In certain embodiments, the known HDAC inhibitor is selected from the group consisting of, but not limited to, trichostatin A, depudecin, trapoxin, suberoylanilide hydroxamic acid, FR901228, MS-27-275, CI-994 sodium butyrate, MGCD0103, and those compounds found in WO 2003/024448, WO 2004/069823, WO 2001/038322, U.S. Pat. No. 6,541,661, WO 01/70675, WO 2004/035525 and WO 2005/030705.

In certain preferred embodiments of the second aspect of the invention, the additional agent is an antisense oligonucleotide that inhibits the expression of a histone deacetylase gene. The combined use of a nucleic acid level inhibitor (e.g., antisense oligonucleotide) and a protein level inhibitor (i.e., inhibitor of histone deacetylase enzyme activity) results in an improved inhibitory effect, thereby reducing the amounts of the inhibitors required to obtain a given inhibitory effect as compared to the amounts necessary when either is used individually. The antisense oligonucleotide according to this aspect of the invention is complementary to regions of RNA or double-stranded DNA that encode one or more of HDAC-1, HDAC-2, HDAC-3, HDAC-4, HDAC-5, HDAC-6, HDAC-7, HDAC-8, HDAC-9, HDAC-10, HDAC-11, SirT1, SirT2, SirT3, SirT4, SirT5, SirT6 and SirT7 (see e.g., GenBank Accession Number U50079 for HDAC-1, GenBank Accession Number U31814 for HDAC-2, and GenBank Accession Number U75697 for HDAC-3).

Inhibition of Histone Deacetylase

In another aspect, the present invention provides a method of inhibiting activity of one or more histone deacetylase, comprising contacting the one or more histone deacetylase with an inhibition effective amount of a compound according to the present invention, or a composition thereof.

Another aspect of the invention provides a method of inhibiting histone deacetylase in a cell, comprising contacting a cell in which inhibition of histone deacetylase is desired with an inhibition effective amount of a compound according to formula (1) as described above, or a composition thereof. Because compounds of the invention inhibit histone deacetylase, they are useful research tools for in vitro study of the role of histone deacetylase in biological processes. Accordingly, in one aspect of the invention, the step of contacting the cell is performed in vitro.

The term "inhibition effective amount" is meant to denote a dosage sufficient to cause inhibition of activity of one or more histone deacetylase in a cell, which cell can be in a multicellular organism. The multicellular organism can be a plant, a fungus, or an animal, preferably a mammal, more preferably a human. The fungus may be infecting a plant or a mammal, preferably a human, and could therefore be located in and/or on the plant or mammal. If the histone deacetylase is in a multicellular organism, the method according to this aspect of the invention comprises administering to the organism a compound or composition according to the present invention. If, for example, the histone deacetylase is a fungal histone deacetylase, and the fungus is infecting a plant or a mammal, preferably a human, the method comprises administering to the plant or mammal a compound or composition according to the present invention. Administration may be by any appropriate route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

In certain preferred embodiments of these aspects of the invention, the methods further comprise contacting a histone deacetylase enzyme or a cell expressing histone deacetylase activity with an additional inhibitory agent, or administering to the organism an additional inhibitory agent. The combined use of separate agents results in an improved inhibitory effect, thereby reducing the amounts of individual inhibitors required to obtain a given inhibitory effect as compared to the amounts necessary when either is used alone. Administration of such separate agents may be done sequentially or concurrently. When co-administered, the separate agents preferably act synergistically to produce a therapeutic effect.

Measurement of the enzymatic activity of a histone deacetylase can be achieved using known methodologies. For example, Yoshida et al., *J. Biol. Chem.*, 265: 17174-17179 (1990), describes the assessment of histone deacetylase enzymatic activity by the detection of acetylated histones in trichostatin A treated cells. Taunton et al., *Science*, 272: 408-411 (1996), similarly describes methods to measure histone deacetylase enzymatic activity using endogenous and recombinant HDAC-1. Other methods include for example those described in US 2006/0063210.

In some preferred embodiments, the compound according to formula (1) interacts with and reduces the activity of all histone deacetylases in the cell. In some other preferred embodiments according to this aspect of the invention, the compound according to formula (1) interacts with and reduces the activity of fewer than all histone deacetylases in the cell. In certain preferred embodiments, the compound interacts with and reduces the activity of one histone deacetylase (e.g., HDAC-1) or a sub-group of histone deacetylases (e.g., HDAC-1, HDAC-2, and HDAC-3) to a greater extent than other histone deacetylases. Where the compound preferentially reduces the activity of a sub-group of histone deacetylases, the reduction in activity of each member of the sub-group may be the same or different. As discussed below, certain particularly preferred compounds according to formula (1) are those that interact with, and reduce the enzymatic activity of, histone deacetylases that are involved in tumorigenesis. Certain other compounds according to formula (1) interact with and reduce the enzymatic activity of a fungal histone deacetylase.

Preferably, the method according to this aspect of the invention causes an inhibition of cell proliferation of the contacted cells. The phrase "inhibition of cell proliferation" is used to denote an ability of a compound according to formula (1) to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer. Where the cells are in a solid growth (e.g., a solid tumor or organ), such an assessment of cell proliferation can be made by measuring the growth with calipers and comparing the size of the growth of contacted cells with non-contacted cells.

Preferably, growth of cells contacted with the compound is retarded by at least 50% as compared to growth of non-contacted cells. More preferably, cell proliferation is inhibited by 100% (i.e., the contacted cells do not increase in number). Most preferably, the phrase "inhibiting cell proliferation" includes a reduction in the number or size of contacted cells, as compared to non-contacted cells. Thus, a compound according to formula (1) that inhibits cell proliferation in a contacted cell may induce the contacted cell to undergo growth retardation, to undergo growth arrest, to undergo programmed cell death (i.e., to apoptose), or to undergo necrotic cell death.

The cell proliferation inhibiting ability of the compounds according to formula (1) allows the synchronization of a population of asynchronously growing cells. For example, the compounds according to formula (1) of the invention may be used to arrest a population of non-neoplastic cells grown in vitro in the G1 or G2 phase of the cell cycle. Such synchronization allows, for example, the identification of gene and/or gene products expressed during the G1 or G2 phase of the cell cycle. Such synchronization of cultured cells may also be useful for testing the efficacy of a new transfection protocol, where transfection efficiency varies and is dependent upon the particular cell cycle phase of the cell to be transfected. Use of the compounds according to formula (1) allows the synchronization of a population of cells, thereby aiding detection of enhanced transfection efficiency.

In some preferred embodiments, the contacted cell is a neoplastic cell. The term "neoplastic cell" is used to denote a cell that shows aberrant cell growth. Preferably, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth. In some embodiments, the compound according to formula (1) induces cell differentiation in the contacted cell. Thus, a neoplastic cell, when contacted with an inhibitor of histone deacetylase may be induced to differentiate, resulting in the production of a non-neoplastic daughter cell that is phylogenetically more advanced than the contacted cell.

In some preferred embodiments, the contacted cell is in an animal. Thus, the invention provides a method for treating a fungal infection or a cell proliferative disease or condition in an animal, comprising administering to an animal in need of such treatment a therapeutically effective amount of a compound according to formula (1) or a composition thereof. Preferably, the animal is a mammal, more preferably a domesticated mammal. Most preferably, the animal is a human.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In particularly preferred embodiments, the invention provides a method for inhibiting neoplastic cell proliferation in an animal comprising administering to an animal having at least one neoplastic cell present in its body a therapeutically effective amount of a compound according to formula (1), or a composition thereof.

It is contemplated that some compounds of the invention have inhibitory activity against a histone deacetylase from a protozoal source. Thus, the invention also provides a method for treating or preventing a protozoal disease or infection, comprising administering to an animal in need of such treatment a therapeutically effective amount of a compound according to formula (1). Preferably the animal is a mammal, more preferably a human. Preferably, the compound used according to this embodiment of the invention inhibits a protozoal histone deacetylase to a greater extent than it inhibits mammalian histone deacetylases, particularly human histone deacetylases.

The present invention further provides a method for treating a fungal disease or infection comprising administering to an animal in need of such treatment a therapeutically effective amount of a compound according to formula (1). Preferably the animal is a mammal, more preferably a human. Preferably, the compound used according to this embodiment of the invention inhibits a fungal histone deacetylase to a greater extent than it inhibits mammalian histone deacetylases, particularly human histone deacetylases.

The term "therapeutically effective amount" as that term is used herein refers to an amount which elicits the desired therapeutic effect. The therapeutic effect is dependent upon the disease being treated and the results desired. As such, the therapeutic effect can be a decrease in the severity of symptoms associated with the disease and/or inhibition (partial or complete) of progression of the disease, or reversal or regression of the disease-state, preferably eliminating or curing of the disease. In other embodiments, the therapeutic effect can be preventing the disease-state from occurring, in particular, when an animal is predisposed to the disease-state but has not yet been diagnosed as having it. Further, the therapeutic effect can be inhibition of histone deacetylase activity in a cell, which cell is preferably in a multicellular organism. The multicellular organism can be a plant, a fungus or an animal, preferably a mammal, more preferably a human. The amount needed to elicit the therapeutic effect can be determined based on the age, health, size and sex of the patient. Optimal amounts can also be determined based on monitoring of the patient's response to treatment. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

When administered systemically, the compound is preferably administered at a sufficient dosage to attain a blood level of the inhibitor from about 0.01 µM to about 100 µM, more preferably from about 0.05 µM to about 50 µM, still more preferably from about 0.1 µM to about 25 µM, and still yet more preferably from about 0.5 µM to about 25 µM. For localized administration, much lower concentrations than this may be effective, and much higher concentrations may be tolerated. One of skill in the art will appreciate that the dosage of histone deacetylase inhibitor necessary to produce a therapeutic effect may vary considerably depending on the disease, tissue, organ, or the particular animal or patient to be treated.

In certain preferred embodiments of the methods for treating a particular disease or condition, the method further comprises administering to the organism in need of treatment an additional therapeutic agent. The combined use of separate agents results in an improved therapeutic effect, thereby reducing the amounts of individual therapeutic agents required to obtain a given therapeutic effect as compared to the amounts necessary when either is used alone. Administration of such separate agents may be done sequentially or concurrently. When co-administered, the separate agents preferably act synergistically to produce a therapeutic effect.

In certain preferred embodiments of this aspect of the invention, the additional therapeutic agent is an antisense oligonucleotide that inhibits the expression of a histone deacetylase. The combined use of a nucleic acid level inhibitor (e.g., antisense oligonucleotide) and a protein level inhibitor (i.e., inhibitor of histone deacetylase enzyme activity) results in an improved therapeutic effect, thereby reducing the amounts of the inhibitors required to obtain a given therapeutic effect as compared to the amounts necessary when either is used individually. The antisense oligonucleotides according to this aspect of the invention are complementary to regions of RNA or double-stranded DNA that encode HDAC-1, HDAC-2, HDAC-3, HDAC-4, HDAC-5, HDAC-6, HDAC-7, HDAC-8, HDAC-9, HDAC-1, HDAC-11, SirT1, SirT2, SirT3, SirT4, SirT5, SirT6 and/or SirT7 (see e.g., GenBank Accession Number U50079 for HDAC-1, GenBank Accession Number U31814 for HDAC-2, and GenBank Accession Number U75697 for HDAC-3).

For purposes of the invention, the term "oligonucleotide" includes polymers of two or more deoxyribonucleosides, ribonucleosides, or 2'-substituted ribonucleoside residues, or any combination thereof. Preferably, such oligonucleotides have from about 6 to about 100 nucleoside residues, more preferably from about 8 to about 50 nucleoside residues, and most preferably from about 12 to about 30 nucleoside residues. The nucleoside residues may be coupled to each other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane.

For purposes of the invention the term "2'-substituted ribonucleoside" includes ribonucleosides in which the hydroxyl group at the 2' position of the pentose moiety is substituted to produce a 2'-O-substituted ribonucleoside. Preferably, such substitution is with a lower alkyl group containing 1-6 saturated or unsaturated carbon atoms, or with an aryl or allyl group having 2-6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups. The term "2'-substituted ribonucleoside" also includes ribonucleosides in which the 2'-hydroxyl group is replaced with an amino group or with a halo group, preferably fluoro.

Particularly preferred antisense oligonucleotides utilized in this aspect of the invention include chimeric oligonucleotides and hybrid oligonucleotides.

For purposes of the invention, a "chimeric oligonucleotide" refers to an oligonucleotide having more than one type of internucleoside linkage. One preferred example of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region (see e.g., Pederson et al. U.S. Pat. Nos. 5,635,377 and 5,366,878). Preferably, such chimeric oligonucleotides contain at least three consecutive internucleoside linkages selected from phosphodiester and phosphorothioate linkages, or combinations thereof.

For purposes of the invention, a "hybrid oligonucleotide" refers to an oligonucleotide having more than one type of nucleoside. One preferred example of such a hybrid oligonucleotide comprises a ribonucleotide or 2'-substituted ribonucleotide region, preferably comprising from about 2 to about 12 2'-substituted nucleotides, and a deoxyribonucleotide region. Preferably, such a hybrid oligonucleotide contains at least three consecutive deoxyribonucleosides and also contains ribonucleosides, 2'-substituted ribonucleosides, preferably 2'-O-substituted ribonucleosides, or combinations thereof (see e.g., Metelev and Agrawal, U.S. Pat. No. 5,652,355).

The exact nucleotide sequence and chemical structure of an antisense oligonucleotide utilized in the invention can be varied, so long as the oligonucleotide retains its ability to inhibit expression of the gene of interest. This is readily determined by testing whether the particular antisense oligonucleotide is active. Useful assays for this purpose include quantitating the mRNA encoding a product of the gene, a Western blotting analysis assay for the product of the gene, an activity assay for an enzymatically active gene product, or a soft agar growth assay, or a reporter gene construct assay, or an in vivo tumor growth assay, all of which are described in detail in this specification or in Ramchandani et al. (1997) Proc. Natl. Acad. Sci. USA 94: 684-689.

Antisense oligonucleotides utilized in the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG) (see, e.g., Pon, R. T. (1993) Methods in Molec. Biol. 20: 465-496).

Particularly preferred oligonucleotides have nucleotide sequences of from about 13 to about 35 nucleotides which include the nucleotide sequences described in for example US 2003/0078216 and US 2002/0061860, both of which are incorporated by reference herein. Yet additional particularly preferred oligonucleotides have nucleotide sequences of from about 15 to about 26 nucleotides.

The foregoing merely summarizes various aspects, and examples thereof, of the invention, and is not intended to be limiting in nature. Certain aspects and embodiments of the invention are described in more detail in the Examples, below.

EXAMPLES

Synthetic Examples sealed flask, cooled to room temperature, diluted with dichloromethane (300 mL) and successively washed with saturated aqueous NaHCO$_3$ and water, dried over MgSO$_4$, filtered and concentrated in vacuo to afford title compound 17 (1.22 g, 91% yield). $^1$H NMR: (DMSO-d$_6$) δ(ppm): 7.65 (d, J=8.8 Hz, 2H), 6.47 (d, J=9.0 Hz, 2H), 3.65 (quint, J=5.3 Hz, 1H), 3.40 (t, J=9.8 Hz, 1H), 3.38 (t, J=9.8 Hz, 1H), 3.29-3.23 (m, 1H),

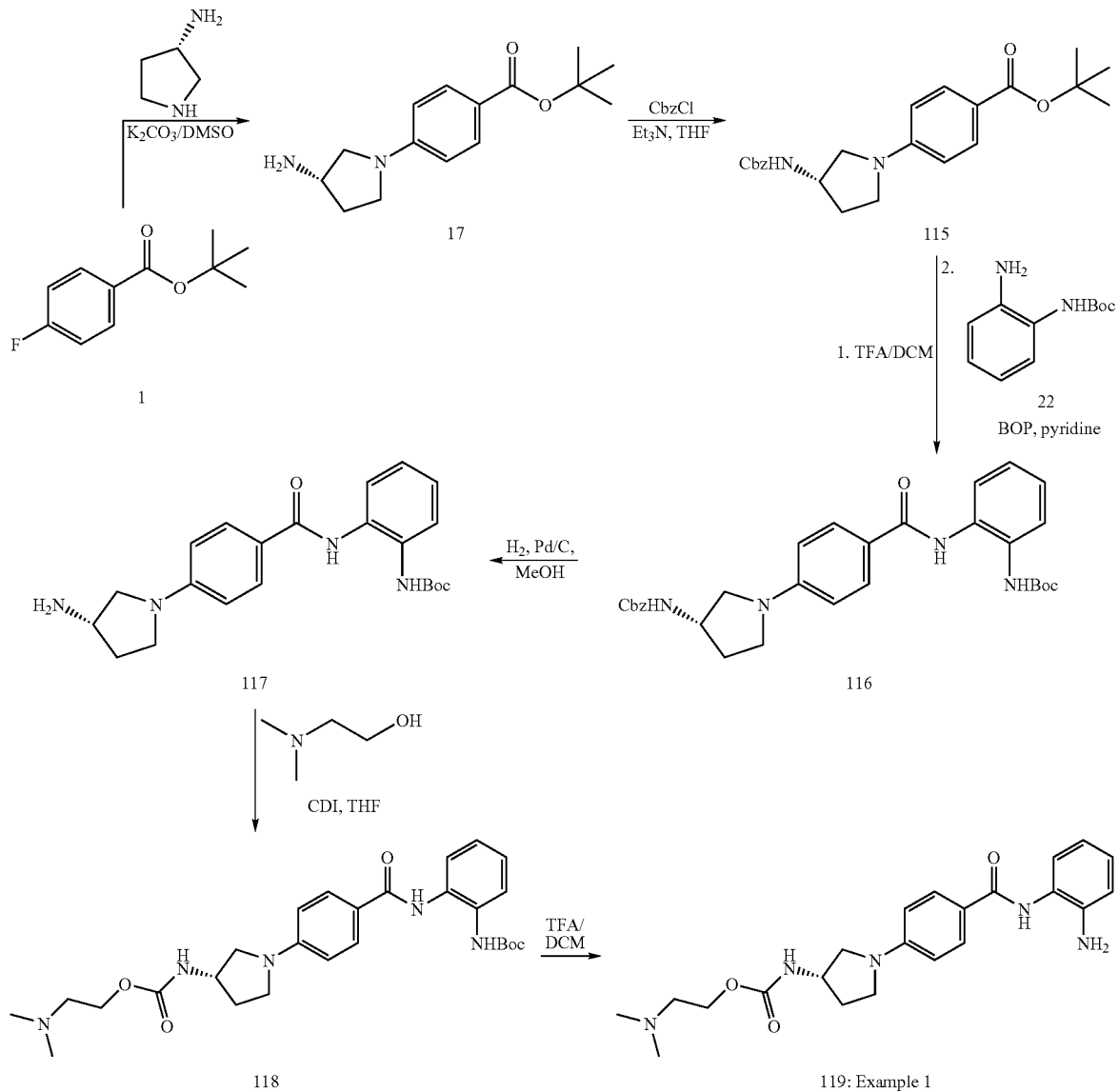

Example 1

(S)-2-(Dimethylamino)ethyl-1-(4-(2-aminophenylcarbamoyl)-phenyl)pyrrolidin-3-ylcarbamate (119)

Starting material: (S)-tert-butyl 4-(3-aminopyrrolidin-1-yl)benzoate (17)

A mixture of tert-butyl 4-fluorobenzoate (1, 1.00 g, 5.1 mmol), (S)-3-aminopyrrolidine (1.5 eq) and K$_2$CO$_3$ (0.84 g, 6.1 mmol, 1.2 eq.) is suspended in 4 mL of anhydrous DMSO. The suspension is stirred at 135° C. under N$_2$ for 16 h in a 2.91 (dd, J=9.8, 4.7 Hz, 1H), 2.03 (sext, J=5.9 Hz, 1H), 1.74-1.63 (m, 3H), 1.48 (s, 9H). m/z: 263.1 (MH$^+$).

Step 1: (S)-tert-Butyl 4-(3-(benzyloxycarbonylamino)pyrrolidin-1-yl)benzoate (115)

A solution of compound 17 (4.37 g, 16.72 mmol) in THF (30 mL) was cooled to 0° C. and treated successively with Et$_3$N (4.6 mL, 3.38 g, 33 mmol) and benzylchloroformate (2.8 mL, 3.42 g, 20 mmol). The reaction mixture was allowed to stir for 2 hrs at 0° C., quenched by adding an aqueous saturated NH$_4$Cl solution (30 mL) and extracted with EtOAc.

The extract was dried over Na₂SO₄, filtered and concentrated. Crude product was purified by flash chromatography using 30% EtOAc in hexanes as an eluent to provide title compound 115 (3 g, 45% yield). LRMS (ESI): (calc) 396.20 (found) 397.2 (MH)+.

Step 2: (S)-tert-Butyl 2-(2-(4-(3-(benzyloxycarbonylamino)pyrrolidin-1-yl)benzamido) phenyl)carbamate (116)

To a suspension of compound 115 (3 g, 7.57 mmol) in dichloromethane (100 mL) was added trifluoroacetic acid (30 mL). The solution was stirred at r.t. for 1.5 hrs and concentrated in vacuo. The residue was dissolved in pyridine (20 mL) and BOP (3.67 g, 8.32 mmol) was added. The mixture was stirred for 10 min, treated with (2-amino-phenyl)-carbamic acid tert-butyl ester (22) (Seto, C. T.; Mathias, J. P.; Whitesides, G. M.; J. Amer. Chem. Soc., (1993), 115, 1321-1329.) (1.73 g, 8.38 mmol) and stirred overnight at room temperature. The pyridine was removed under reduced pressure and the crude product was purified by flash chromatography using a gradient 50-100% EtOAc in hexanes as an eluent, to afford title compound 116 (2.2 g, 55% yield). LRMS (ESI): (calc) 530.25 (found) 531.4 (MH)+.

Step 3: (S)-tert-Butyl 2-(4-(3-aminopyrrolidin-1-yl)benzamido)phenylcarbamate (117)

A solution of 116 (2.2 g, 4.15 mmol) and Pd/C (300 mg, 10% on charcoal) in MeOH (10 mL) was stirred under hydrogen atmosphere for 5 hrs. The reaction mixture was filtered through a Celite® pad and concentrated to provide title compound 117 (1.5 g, 91% yield) which was used in the next step without further purification. ¹H NMR (MeOH-d4) δ(ppm): 7.82 (d, 2H, J=8.8 Hz), 7.55 (m, 1H), 7.40 (m, 1H), 7.18 (m, 2H,), 6.56 (d, 2H, J=9.0 Hz), 3.63 (m, 1H), 3.50 (m, 2H), 3.08 (dd, 1H, J=4.8 Hz, J=10.0 Hz), 2.21 (m, 1H), 1.85 (m, 1H), 1.48 (s, 9H), (a signal corresponding to 1H is missing due to overlapping with the signals of the solvent). LRMS (ESI) (calc) 396.22 (found) 397.2 (MH)+.

Step 4: S-tert-Butyl 2-(2-(4-(3-((2-(dimethylamino)ethoxy)carbonylamino)pyrrolidin-1-yl)benzamido) phenyl)carbamate (118)

A solution of 2-(dimethylamino)ethanol (57 μL, 55 mg, 0.52 mmol) in THF (1.5 mL) was cooled to 0° C., treated with carbonyl diimidazole (84 mg, 0.52 mmol) and stirred for 1 h at 0° C. To the reaction mixture was then added compound 117 (50 mg, 0.13 mmol). The reaction mixture was stirred at room temperature overnight, concentrated, and the residue was purified by flash chromatography (5-10% MeOH in dichloromethane), to provide title compound 118 (52 mg, 76% yield). LRMS (ESI): (calc) 511.28 (found) 512.3 (MH)+.

Alternatively, commercially available chloroformates or thiocarbonyl diimidazoles were used in the synthesis of analogues of compound 118 ultimately leading to the target molecules shown in Table 2.

Step 5: (S)-2-(Dimethylamino)ethyl 1-(4-(2-aminophenylcarbamoyl)phenyl)pyrrolidin-3-ylcarbamate (119)

A solution of compound 118 (92 mg, 0.18 mmol) in dichloromethane (5 mL) and TFA (2 mL) was stirred at room temperature for 1 h and concentrated. The residue was diluted with EtOAc (5 mL), washed with saturated NaHCO₃ solution (5 mL), dried over Na₂SO₄, filtered and concentrated. Crude product was purified by flash chromatography using 30% MeOH in dichloromethane as an eluent to provide title compound 119 (44 mg, 59% yield). ¹H NMR (MeOH-d4) δ(ppm): 7.86 (d, 2H, J=8.8 Hz), 7.68 (s, 1H), 7.15 (d, 1H, J=7.8 Hz), 7.05 (m, 2H,), 6.89 (d, 1H, J=8.0 Hz), 6.75 (t, 1H, J=7.6 Hz), 6.60 (d, 2H, J=9.0 Hz), 4.29 (m, 1H), 4.17 (m, 2H), 3.61 (m, 1H), 3.41 (m, 1H), 3.23 (dd, 1H, J=4.3 Hz, J=10.2 Hz), 2.62 (m, 2H), 2.32 (m, 7H), 2.01 (m, 1H), (a signal corresponding to 1H is missing due to overlapping with the signals of the solvent). LRMS (ESI): (calc) 411.23 (found) 412.2 (MH)+.

Compounds in Table 2 were prepared using procedures analogous to those described above for compound 119.

TABLE 2

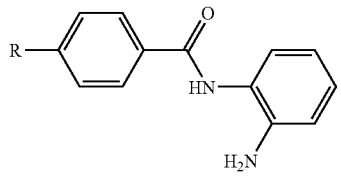

| Ex. | Cpd. | R | Name | Characterization |
|---|---|---|---|---|
| 2 | 120 | MeO-NH-C(O)-pyrrolidin-3-yl-N- | (S)-Methyl 1-(4-(2-aminophenylcarbamoyl)phenyl)pyrrolidin-3-yl carbamate | ¹H NMR: (MeOH-d4) δ (ppm): 8.08 (d, 2 H, J = 8.6 Hz), 7.41 (d, 1 H, J = 7.8 Hz), 7.29 (t, 1 H, J = 8.0 Hz), 7.10 (d, 1 H, J = 8.0 Hz), 7.02 (t, 1 H, J = 7.6 Hz), 6.79 (d, 2 H, J = 9.0 Hz), 4.55 (m, 1 H), 3.86 (s, 3 H), 3.6-3.8 (m, 3 H), 3.46 (m, 1 H), 2.53 (m, 1 H), 2.26 (m, 1 H), m/z: 355.1 (MH⁺). |

TABLE 2-continued

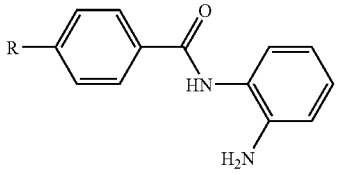

| Ex. | Cpd. | R | Name | Characterization |
|---|---|---|---|---|
| 3 | 121 | 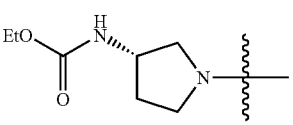 | (S)-Ethyl 1-(4-(2-aminophenyl-carbamoyl)phenyl)pyrrolidin-3-yl carbamate | 1H NMR: (DMSO) δ (ppm): 9.35 (s, 1 H), 8.85 (d, J = 8.8 2 H), 7.51 (d, J = 7.0 Hz, 1 H), 7.14 (dd, J = 7.8, 1.2 Hz, 1 H), 6.94 (td, J = 7.6, 1.6 Hz, 1 H), 6.77 (dd, J = 7.8, 1.2 Hz, 1 H), 6.59 (td, J = 7.4, 1.2 Hz, 1 H), 6.56 (d, J = 9.0 Hz, 2 H), 4.82 (s, 2 H), 4.20 (q, J = 6.0 Hz, 2 H), 4.0 (q, J = 7.0, 2 H), 3.54 (q, J = 5.5 Hz, 1 H), 3.44 (q, J = 7.9 Hz, 1 H), 3.36-3.30 (m, 1 H, overlap with water), 3.15 (q, J = 5.0, Hz 1 H), 2.22-2.14 (m, 1 H), 1.97-1.89 (m, 1 H). MS: 468.2 (calc), 469.3 (obs) (MH+). |
| 4 | 122 | 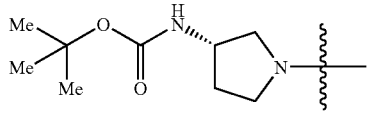 | (S)-tert-Butyl 1-(4-(2-aminophenyl-carbamoyl)phenyl)pyrrolidin-3-yl carbamate | $^1$H NMR: (CDCl$_3$) δ (ppm): 7.87 (s, 1 H), 7.76 (d, 2 H, J = 8.6 Hz), 7.24 (d, 1 H, J = 10.5 Hz), 7.03 (t, 1 H, J = 7.6 Hz), 6.79 (m, 2 H), 6.48 (d, 2 H, J = 8.6 Hz), 4.93 (d, 1 H, J = 7.4 Hz), 4.34 (br.s, 1 H), 3.59 (m, 1 H), 3.3-3.5 (m, 3 H), 3.18 (m, 1 H), 2.26 (m, 1 H), 1.97 (m, 1 H), 1.46 (s, 9 H), m/z: 397.2 (MH+). |
| 5 | 123 | 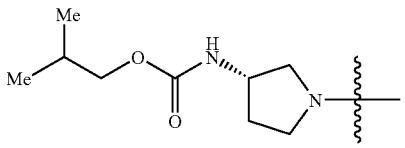 | (S)-Isobutyl 1-(4-(2-aminophenyl-carbamoyl)phenyl)pyrrolidin-3-yl carbamate | $^1$H NMR: (CDCl$_3$) δ (ppm): 7.79 (d, 2 H, J = 8.8 Hz), 7.74 (s, 1 H), 7.26 (d, 1 H, J = 8.0 Hz), 7.05 (t, 1 H, J = 7.6 Hz), 6.82 (m, 2 H), 6.53 (d, 2 H, J = 9.0 Hz), 4.96 (m, 1 H), 4.40 (br.s, 1 H), 3.88 (m, 3 H), 3.63 (m, 1 H), 3.45 (m, 2 H), 3.23 (m, 1 H), 2.30 (m, 1 H), 2.00 (m, 1 H), 1.89 (m, 1 H), 0.92 (d, 6 H, J = 6.5 Hz), m/z: 397.1 (MH+). |
| 6 | 124 | 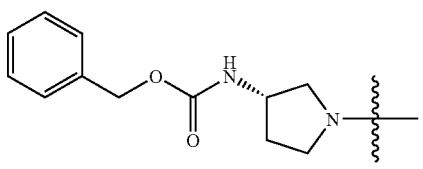 | (S)-Benzyl 1-(4-(2-aminophenyl-carbamoyl)phenyl)pyrrolidin-3-yl carbamate | $^1$H NMR: (MeOH-d4) δ (ppm): 8.16 (d, 2 H, J = 8.8 Hz), 7.82 (m, 5 H), 7.51 (d, 1 H, J = 7.8 Hz), 7.38 (t, 1 H, J = 7.5 Hz), 7.18 (d, 1 H, J = 8.1 Hz), 7.11 (t, 1 H, J = 7.8 Hz), 6.88 (d, 2 H, J = 9.0 Hz), 5.41 (s, 2 H), 4.67 (m, 1 H), 3.98 (m, 1 H), 3.6-3.9 (m, 5 H), 3.57 (m, 1 H), 2.62 (m, 1 H), 2.36 (m, 1 H), m/z: 431.1 (MH+). |
| 7 | 126 | 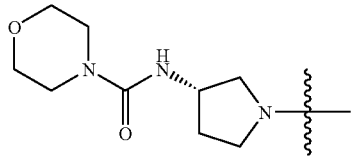 | (S)-N-(1-(4-(2-Aminophenyl-carbamoyl)phenyl)pyrrolidin-3-yl)morpholine-4-carboxamide | $^1$H NMR: (MeOH-d4) δ (ppm): 7.83 (d, 2 H, J = 8.8 Hz), 7.15 (t, 1 H, J = 7.8 Hz), 7.04 (t, 1 H, J = 7.8 Hz), 6.86 (d, 1 H, J = 8.0 Hz), 6.76 (t, 1 H, J = 7.6 Hz), 6.56 (d, 2 H, J = 8.8 Hz), 4.42 (m, 1 H), 3.65 (m, 4 H), 3.49 (m, 1 H), 3.36 (m, 5 H), 3.20 (dd, 1 H, J = 5.7 Hz, J = 10.0 Hz), 2.30 (m, 1 H), 2.03 (m, 1 H), m/z: 410.1 (MH+). |
| 8 | 127 | 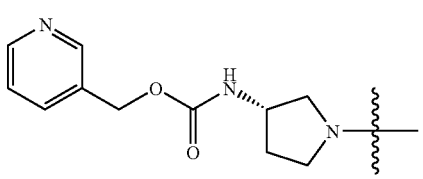 | ((S)-Pyridin-3-ylmethyl-1-(4-(2-aminophenyl-carbamoyl)phenyl)pyrrolidin-3-yl carbamate | $^1$H NMR: (MeOH-d4) δ (ppm): 8.50 (s, 1 H), 8.42 (d, 1 H, J = 4.7 Hz), 7.80 (d, 2 H, J = 8.8 Hz), 7.77 (m, 1 H), 7.35 (m, 1 H), 7.12 (d, 1 H, J = 7.8 Hz), 7.01 (t, 1 H, J = 7.4 Hz), 6.82 (d, 1 H, J = 8.0 Hz), 6.74 (t, 1 H, J = 7.8 Hz), 6.53 (d, 2 H, J = 9.0 Hz), 5.09 (s, 2 H), 4.29 (m, 1 H), 3.61 (m, 1 H), 3.47 (m, 1 H), 3.36 (m, 1 H), 3.27 (m, 2 H), 3.20 (dd, 1 H, J = 5.7 Hz, J = 10.0 Hz), 2.26 (m, 1 H), 2.01 (m, 1 H), m/z: 432.2 (MH+). |

TABLE 2-continued

| Ex. | Cpd. | R | Name | Characterization |
|---|---|---|---|---|
| 9 | 128 | [pyridin-3-ylmethyl-NH-C(O)-NH-pyrrolidin-3-yl (S)] | (S)-N-(2-Aminophenyl)-4-(3-(3-(pyridin-3-ylmethyl)ureido)pyrrolidin-1-yl)benzamide | ¹H NMR: (MeOH-d4) δ (ppm): 8.44 (s, 1 H), 8.38 (d, 1 H, J = 4.1 Hz), 7.84 (d, 2 H, J = 8.8 Hz), 7.73 (d, 1 H, J = 7.8 Hz), 7.67 (s, 2 H), 7.35 (m, 1 H), 7.15 (d, 1 H, J = 7.8 Hz), 7.04 (m, 3 H), 6.86 (d, 1 H, J = 8.0 Hz), 6.76 (t, 1 H, J = 7.8 Hz), 6.57 (d, 2 H, J = 9.0 Hz), 4.40 (m, 1 H), 4.34 (s, 2 H), 3.63 (m, 1 H), 3.49 (m, 2 H), 3.30 (m, 1 H), 3.20 (dd, 1 H, J = 4.4 Hz, J = 10.2 Hz), 2.29 (m, 1 H), 1.98 (m, 1 H), m/z: 431.2 (MH⁺). |
| 10 | 129 | MeO-CH₂CH₂-O-C(O)-NH-pyrrolidin-3-yl (S) | (S)-2-Methoxyethyl-1-(4-(2-aminophenylcarbamoyl)phenyl)pyrrolidin-3-yl carbamate | ¹H NMR: (MeOH-d4) δ (ppm): 7.86 (d, 2 H, J = 9.0 Hz), 7.15 (d, 1 H, J = 8.0 Hz), 7.05 (t, 1 H, J = 7.8 Hz), 6.89 (d, 1 H, J = 8.0 Hz), 6.76 (t, 1 H, J = 7.5 Hz), 6.60 (d, 2 H, J = 9.0 Hz), 4.30 (m, 1 H), 4.16 (m, 2 H), 3.3-3.7 (m, 7 H), 3.24 (dd, 1 H, J = 4.7 Hz, J = 10.0 Hz), 2.28 (m, 1 H), 2.00 (m, 1 H), m/z: 399.1 (MH⁺). |
| 11 | 130 | MeO-CH₂CH₂-O-C(O)-NH-pyrrolidin-3-yl (R) | (R)-2-Methoxyethyl 1-(5-(2-aminophenylcarbamoyl)pyridin-2-yl)pyrrolidin-3-yl carbamate | ¹H NMR: (DMSO) δ (ppm): 9.35 (s, 1 H), 7.86 (d, J = 9.08, 2 H), 7.65 (d, J = 6.7 Hz, 1 H), 7.14 (dd, J = 7.8, 1.4 Hz, 1 H), 6.94 (td, J = 7.6, 1.6 Hz, 1 H), 6.77 (dd, J = 7.80, 1.4 Hz, 1 H), 6.59 (td, J = 7.6, 1.42 Hz, 1 H), 6.56 (d, J = 9.0 Hz, 2 H), 4.82 (s, 2 H), 4.19 (q, J = 5.9 Hz, 1 H), 4.08 (t, J = 4.5 Hz, 2 H), 3.54 (dd, J = 10.0, 6.5 Hz, 1 H), 3.49 (t, J = 4.7 Hz, 2 H), 3.46-3.42 (m, 1 H), 3.37-3.30 (m, overlap with water, 1 H), 3.25 (s, 3 H), 3.16 (q, J = 5.0 Hz, 1 H), 2.23-2.15 (m, 1 H), 1.979-1.89 (m, 1 H). MS: 398.2 (calc), 399.3 (obs) (MH⁺). |
| 12 | 131 | [pyridin-3-ylmethyl-NH-C(S)-NH-pyrrolidin-3-yl (S)] | (S)-N-(2-Aminophenyl)-4-(3-(3-(pyridin-3-ylmethyl)thioureido)pyrrolidin-1-yl)benzamide | ¹H NMR: (MeOH-d4) δ (ppm): 8.50 (s, 1 H), 8.40 (d, 1 H, J = 3.8 Hz), 7.78 (m, 3 H), 7.39 (dd, 1 H, J = 5.0 Hz, J = 8.0 Hz), 7.15 (d, 1 H, J = 7.8 Hz), 7.05 (t, 1 H, J = 7.8 Hz), 6.89 (d, 1 H, J = 8.0 Hz), 6.76 (t, 1 H, J = 7.6 Hz), 6.59 (d, 2 H, J = 8.8 Hz), 4.49 (dd, 2 H, J = 15.7 Hz, J = 27.2 Hz), 4.29 (m, 1 H), 3.49 (dd, 1 H, J = 7.5 Hz, J = 10.8 Hz), 3.20 (t, 1 H, J = 7.0 Hz), 3.10 (dd, 1 H, J = 6.0 Hz, J = 10.8 Hz), 1.8-2.0 (m, 2 H), m/z: 447.1 (MH⁻). |
| 13 | 135 | MeO-C(S)-NH-pyrrolidin-3-yl (S) | (S)-O-Methyl 1-(4-(2-aminophenylcarbamoyl)phenyl)pyrrolidin-3-yl carbamothioate | ¹H NMR: (DMSO) δ (ppm): 9.52 (d, 1 H, J = 6.9 Hz), 9.35 (s, 1 H), 7.84 (d, 2 H, J = 8.8 Hz), 7.12 (d, 1 H, J = 7.9 Hz), 6.92 (t, 1 H, J = 8.4 Hz), 6.75 (d, 1 H, 8.0 Hz), 6.5-6.6 (m, 3 H), 4.81 (s, 2 H), 4.67 (m, 0.78 H), 4.4 (m, 0.22 H), 3.94 (s, 0.6 H), 3.85 (s, 2.4 H), 3.3.2-3.7 (m, 4 H), 2.0-2.4 (m, 2 H), m/z: 371.0 (MH⁺). |

Scheme 2

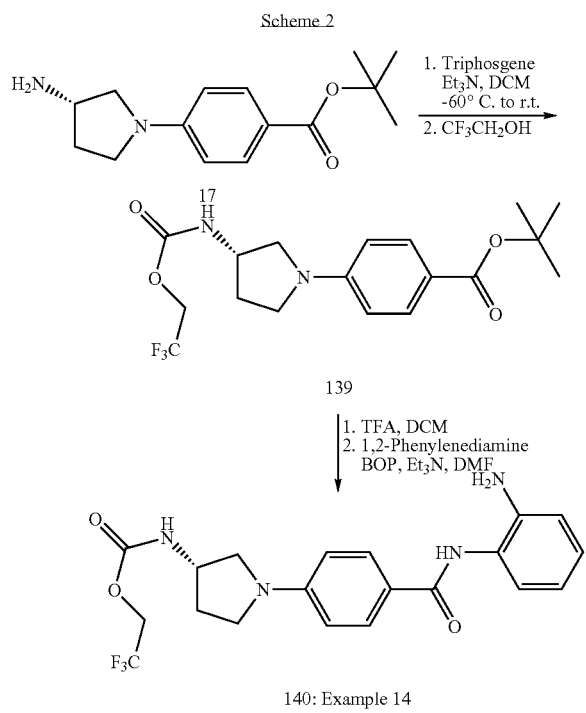

140: Example 14

Example 14

(S)-2,2,2-Trifluoroethyl 1-(4-(2-aminophenylcarbamoyl)phenyl) -pyrrolidin-3-ylcarbamate (140)

Step 1: (S)-tert-Butyl 4-(3-((2,2,2-trifluoroethoxy)carbonylamino)pyrrolidin-1-yl)benzoate (139)

The compound 17 (400 mg, 1.52 mmol) and Et$_3$N (850 ml, 6.10 mmol) were added to a stirring solution of triphosgene (181 mg, 0.61 mmol) in dichloromethane (8 mL) at −60° C. The reaction mixture was allowed to warm to room temperature and stirred for additional 2 h. 2,2,2-Trifluoroethanol (133 µl, 1.82 mmol) was added and the reaction mixture was stirred for 16 h, diluted with dichloromethane, washed with saturated aqueous NH$_4$Cl, NaHCO$_3$ and brine, dried over MgSO$_4$, filtered and concentrated in vacuo. The solid residue was purified by flash chromatography (eluent 0.5-1% MeOH-dichloromethane) to afford the title compound 139 as a white solid (375 mg, 64% yield). $^1$H NMR: (DMSO) δ(ppm): 8.09 (d, J=6.8 Hz, 1H), 7.70 (d, J=8.8 Hz, 2H), 6.52 (d, J=8.8, 2H), 4.66 (q, J=9.1 Hz, 2H), 4.24-4.20 (m, 1H), 3.57-3.53 (m, 1H), 3.47-3.41 (m, 1H), 3.36-3.30 (m, 1H, overlap with water), 3.19-3.16 (m, 1H), 2.21-2.16 (m, 1H), 1.99-1.93 (m, 1H), 1.50 (s, 9H). LRMS (ESI): (calc.) 388.2; (obt.) 389.2 (M+H)$^+$.

Steps 2 and 3: (S)-2,2,2-Trifluoroethyl 1-(4-(2-aminophenylcarbamoyl)phenyl)pyrrolidin-3-ylcarbamate (140)

A solution of 139 (0.404 g, 0.95 mmol) in a mixture of dichloromethane-trifluoroacetic acid (5 mL per 0.95 mmol of 139) was stirred at room temperature for 16 h, concentrated to afford the corresponding intermediatecarboxylic acid as its trifluoroacetate salt (the structure is not shown in the scheme 2), which was stored under vacuum and used without further purification (assumed quantitative yield).

A solution of the carboxylic acid in pyridine (4 mL), 1,2-phenylenediamine (1.7 eq) and BOP reagent (1.4 eq) was stirred at room temperature for 24 h, treated with water (1 mL) and stirred for an additional 20 min. The resultant mixture was diluted with ethyl acetate, washed with aqueous sodium bicarbonate solution, dried over MgSO$_4$ and concentrated. The residue was purified by flash column chromatography on silica gel (eluent: a gradient of isopropyl alcohol from 3% to 7%, in dichloromethane) followed by reverse phase preparative HPLC (Aquasil C18 column, elution with a gradient of MeOH 15% to 95%, in water) to afford title compound 140 as an off-white solid in 61% yield. $^1$H NMR: (DMSO) δ (ppm): 9.37 (s, 1H), 8.11 (d, J=6.8 Hz, 1H), 7.86 (d, J=8.8 Hz, 2H), 7.14 (dd, J=7.6, 1.4 Hz, 1H), 6.94 (td, J=7.6, 1.6 Hz, 1H), 6.77 (dd, J=8.0, 1.4 Hz, 1H), 6.61-6.56 (m, 3H), 4.83 (s, 2H), 4.67 (q, J=9.1 Hz, 2H), 4.23 (m, 1H), 3.56 (q, J=5.4 Hz, 1H), 3.46-3.42 (m, 1H), 3.39 (m, 1H, overlap with water), 3.19 (q, J=5.0 Hz, 1H), 2.24-2.20 (m, 1H), 1.99-1.96 (m, 1H). LRMS (ESI): (calc.) 422.2; (obt.) 423.0 (M+H)$^+$ The skilled artisan will appreciate that instead of pyridine other solvents, such as DMF, may be used if a suitable base, such as triethylamine, is added.

Compounds in Table 3 were prepared using procedures analogous to those described above for compound 140.

TABLE 3

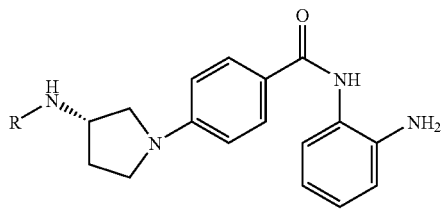

| Ex | Cpd | R | Name | Characterization |
|---|---|---|---|---|
| 15 | 141 | (dimethylaminoacetyl group) | (S)-N-(2-Aminophenyl)-4-(3-(2-(dimethylamino)acetamido)pyrrolidin-1-yl)benzamide | 1H NMR: (DMSO) δ (ppm): 9.33 (s, 1 H), 8.01 (d, J = 7.2 Hz, 1 H), 7.86 (d, J = 9.0, 2 H), 7.14 (dd, J = 7.8, 2.3 Hz, 1 H), 6.93 (t, J = 8.2 Hz, 1 H), 6.77 (dd, J = 7.8, 1.4 Hz, 1 H), 6.61-6.56 (m, 3 H), 4.83 (s, 2 H), 4.45 (q, J = 6.5 Hz, 1 H), 3.57-3.53 (m, 1 H), 3.43-3.41 (m, 1 H), 3.39-3.29 (m, 1 H, overlap with water), 3.21-3.17 (m, 1 H), 2.87 (s, 2 H), 2.19-2.16 (m, 7 H), 2.02-1.99 (m, 1 H). MS: 381.1 (calc), 382.2 (obs) (MH$^+$). |

TABLE 3-continued

| Ex | Cpd | R | Name | Characterization |
|---|---|---|---|---|
| 16 | 142 | (pyridin-4-ylmethyl carbamate group) | (S)-Pyridin-4-ylmethyl 1-(4-(2-aminophenyl carbamoyl)phenyl) pyrrolidin-3-yl carbamate | 1H NMR: (DMSO) δ (ppm): 9.37 (s, 1 H), 8.56 (d, J = 6.1 Hz, 2 H), 7.87-7.85 (m, 3 H), 7.33 (d, J = 5.7 Hz, 1 H), 7.14 (dd, J = 7.8, 1.6 Hz, 1 H), 6.94 (td, J = 7.5, 1.4 Hz, 1 H), 6.77 (dd, J = 8.0, 1.4 Hz, 1 H), 6.61-6.56 (m, 3 H), 5.10 (s, 2 H), 4.83 (s, 2 H), 4.26-4.22 (m, 1 H), 3.59-3.55 (m, 1 H), 3.47-3.42 (m, 1 H), 3.3 (m, overlap with water, 1 H), 3.22-3.16 (m, 1 H), 2.24-2.19 (m, 1 H), 1.99-1.94 (m, 1 H). MS: 431.1 (calc), 432.1 (obs) (MH+). |
| 17 | 143 | (pyridin-2-ylmethyl carbamate group) | (S)-Pyridin-2-ylmethyl 1-(4-(2-aminophenyl carbamoyl)phenyl) pyrrolidin-3-yl carbamate | 1H NMR: (DMSO) δ (ppm): 9.37 (s, 1 H), 8.55 (d, J = 4.3, 1 H), 7.87-7.80 (m, 4 H), 7.38 (d, J = 8.0 Hz, 1 H), 7.33 (dd, J = 7.4, 4.7 Hz, 1 H), 7.14 (dd, J = 7.8, 1.4 Hz, 1 H), 6.94 (td, J = 7.5, 1.6 Hz, 1 H), 6.77 (dd, J = 8.0, 1.4 Hz, 1 H), 6.61-6.56 (m, 3 H), 5.10 (s, 2 H), 4.83 (s, 2 H), 4.26-4.22 (m, 1 H), 3.59-3.55 (m, 1 H), 3.49-3.43 (m, 1 H), 3.3 (m, overlap with water, 1 H), 3.21-3.18 (m, 1 H), 2.24-2.19 (m, 1 H), 1.99-1.95 (m, 1 H). MS: 431.1 (calc), 432.1 (obs) (MH+). |
| 18 | 144 | (3-(dimethylamino)propyl carbamate group) | (S)-3-(Dimethyl amino)propyl 1-(4-(2-aminophenyl-carbamoyl)phenyl) pyrrolidin-3-yl carbamate | 1H NMR: (DMSO) δ (ppm): 9.39 (s, 1 H), 7.87 (d, J = 9.4, 2 H), 7.64 (d, J = 6.8 Hz, 1 H), 7.15 (dd, J = 7.8, 1.4 Hz, 1 H), 6.95 (td, J = 7.56, 1.4 Hz, 1 H), 6.78 (dd, J = 8.0, 1.4 Hz, 1 H), 6.61-6.56 (m, 3 H), 4.84 (s, 2 H), 4.23-4.19 (m, 1 H), 4.02 (t, J = 6.1 Hz, 2 H), 3.57-3.53 (m, 1 H), 3.46-3.40 (m, 1 H), 3.35 (m, 1 H, overlap with water), 3.19 (m, 1 H, overlap with MeOH), 2.97 (m, 2 H), 2.66 (s, 6 H), 2.22-2.17 (m, 1 H), 1.99-1.91 (m, 3 H). MS: 425.2 (calc), 425.1 (obs) (MH+). |
| 19 | 145 | (furan-3-ylmethyl carbamate group) | (S)-Furan-3-ylmethyl 1-(4-(2-aminophenyl-carbamoyl)phenyl) pyrrolidin-3-yl carbamate | 1H NMR: (DMSO) δ (ppm): 9.36 (s, 1 H), 7.85 (d, J = 8.8 Hz, 2 H), 7.71 (s, 1 H), 7.65-7.62 (m, 2 H), 7.13 (dd, J = 6.5, 3.5 Hz, 1 H), 6.94 (td, J = 7.6, 1.6 Hz, 1 H), 6.77 (dd, J = 8.0, 1.4 Hz, 1 H), 6.61-6.51 (m, 4 H), 4.89 (s, 2 H), 4.83 (s, 2 H), 4.24-4.20 (m, 1 H), 3.57-3.53 (m, 1 H), 3.45-3.41 (m, 1 H), 3.3 (m, overlap with water, 1 H), 3.18-3.14 (m, 1 H), 2.21-2.17 (m, 1 H), 1.95-1.91 (m, 1 H). MS: 420.2 (calc), 421.0 (obs) (MH+). |

TABLE 3-continued
| Ex | Cpd | R | Name | Characterization |
|---|---|---|---|---|
| 20 | 146 | (R)-1-methylpyrrolidin-3-yl group | (R)-1-Methylpyrrolidin-3-yl (S)-1-(4-(2-aminophenyl-carbamoyl)phenyl)pyrrolidin-3-yl carbamate | 1H NMR: (DMSO) δ (ppm): 9.37 (s, 1 H), 9.17 (s, 1 H), 7.86 (d, J = 8.8 Hz, 2 H), 7.60 (d, J = 6.8 Hz, 1 H), 7.14 (dd, J = 7.8, 1.4 Hz, 1 H), 6.94 (td, J = 7.6, 1.3 Hz, 1 H), 6.77 (dd, J = 8.0, 1.4 Hz, 1 H), 6.61-6.55 (m, 3 H), 5.02-4.98 (m, 1 H), 4.21-4.16 (m, 1 H), 3.56-3.52 (m, 1 H), 3.47-3.41 (m, 1 H), 3.35-3.29 (m, 1 H), 3.15-3.13 (m, 1 H), 2.71-2.65 (m, 2 H), 2.89-2.56 (m, 1 H), 2.37-2.31 (m, 1 H). 2.27 (s, 3 H), 2.27-2.12 (m, 2 H), 1.96-1.88 (m, 1 H), 1.73-1.67 (m, 1 H). MS: 424.2 (calc), 424.1 (obs) (MH+). |
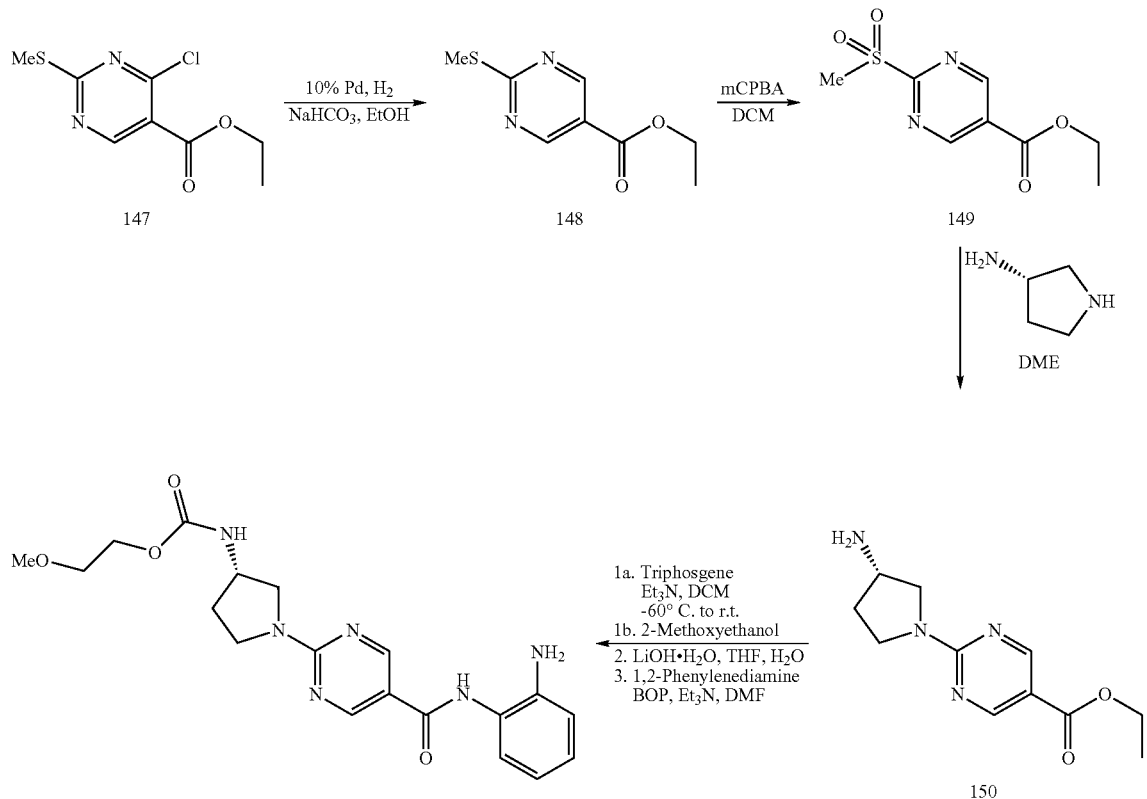
Scheme 3

Example 21

(S)-2-Methoxyethyl 1-(5-(2-aminophenylcarbamoyl)pyrimidin-2-yl)pyrrolidin-3-ylcarbamate (151)

Step 1: Ethyl 2-(methylthio)pyrimidine-5-carboxylate (148)

A solution of 147 (3.00 g, 12.9 mmol) and NaHCO$_3$ (1.08 g, 12.9 mmol) in EtOH (60 ml) was hydrogenated over Pd/C 10% (2.3 g, 11.6 mmol) for 2 days. The suspension was filtered through a Celite® pad (rinsed with MeOH after the filtration). The filtrate and washings were collected, evaporated and the crude product was purified by flash chromatography (eluent 5-85 (AcOEt/Hexane) to afford the title compound 148 as transparent oil (1.79 g, 70% yield). LRMS (ESI): (calc.) 198.1; (obt.) 199.1 (M+H)$^+$.

Step 2: Ethyl 2-(methylsulfonyl)pyrimidine-5-carboxylate (149)

A suspension of mCPBA (5.47 g, 31.68 mmol) in dichloromethane (30 ml) was added to a solution of 148 (1.57 g, 7.92 mmol) in dichloromethane (20 ml) at 0° C. The reaction mixture was allowed to warm to room temperature, stirred for an additional 3 h and quenched with an aqueous solution of Na$_2$S$_2$O$_3$. The mixture was extracted with dichloromethane and the extract was washed with saturated aqueous NaHCO$_3$ and brine, dried over MgSO$_4$, filtered and concentrated in vacuo. The solid residue was purified by flash chromatography (eluent 0.5-1% MeOH/dichloromethane) to afford the title compound 149 as a white solid (1.23 g, 67% yield). $^1$H NMR: (DMSO) δ (ppm): 9.48 (s, 2H), 4.42 (q, J=7.1 Hz, 2H), 3.47 (s, 3H), 1.36 (t, J=7.0 Hz, 3H). LRMS (ESI): (calc.) 230.0; (obt.) 231.0 (M+H)$^+$.

Step 3: (S)-Ethyl 2-(3-aminopyrrolidin-1-yl)pyrimidine-5-carboxylate (150)

The methylsulfone 149 (450 mg, 1.95 mmol) was added to a solution of 3-(S)(−) aminopyrrolidine (253 mg, 2.93 mmol) in DME (10 ml). The reaction mixture was stirred for 10 min at room temperature and the solvent was evaporated. The remaining solid was dissolved in dichloromethane, the solution was washed with saturated aqueous NaHCO$_3$ and brine, dried over MgSO$_4$, filtered and concentrated in vacuo to afford the title compound 150 as a yellow solid (416 mg, 90% yield). $^1$H NMR: (DMSO) δ (ppm): 8.76 (s, 2H), 4.26 (q, J=7.1 Hz, 2H), 3.70-3.53 (m, 4H), 3.26 (dd, J=11.3, 3.9 Hz, 1H), 2.07-1.98 (m, 1H), 1.75-1.67 (m, 3H), 1.29 (t, J=7.0 Hz, 3H). LRMS (ESI): (calc.) 236.1; (obt.) 237.2 (M+H)$^+$.

Steps 4 to 6: (S)-2-Methoxyethyl 1-(5-(2-aminophenylcarbamoyl)pyrimidin-2-yl)pyrrolidin-3-ylcarbamate (151)

Following the procedures described above for the synthesis of compound 140 (example 14, scheme 2) but substituting compound 17 for compound 150 and 2,2,2-trifluoroethanol for 2-methoxyethanol title compound 151 was obtained. $^1$H NMR: (DMSO) δ (ppm): 9.49 (s, 1H), 8.88 (s, 2H), 7.67 (d, J=6.5 Hz, 1H), 7.13 (d, J=7.8 Hz, 1H), 6.96 (td, J=7.5, 1.4 Hz, 1H), 6.76 (d, J=8.0 Hz, 1H), 6.57 (td, J=7.4, 1.2 Hz, 1H), 4.93 (s, 2H), 4.16 (q, J=5.7 Hz, 1H), 4.07 (t, J=4.5 Hz, 2H), 3.76-3.72 (m, 1H), 3.69-3.64 (m, 1H), 3.62-3.55 (m, 1H). 3.50-3.44 (m, 3H), 3.24 (s, 3H), 2.212-2.134 (m, 1H), 1.95-1.89 (m, 1H). LRMS (ESI): (calc.) 400.2; (obt.) 401.2 (M+H)$^+$.

Compounds in Table 4 were prepared using procedures analogous to those described above for compound 151.

TABLE 4

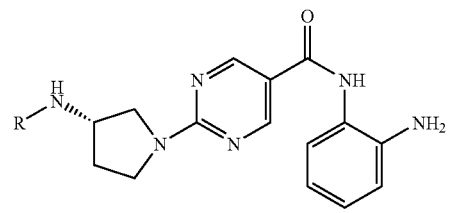

| Ex | Cpd | R | Name | Characterization |
|----|-----|---|------|-----------------|
| 22 | 152 | (H$_3$CO-C(O)-) | (S)-Methyl 1-(5-(2-aminophenyl carbamoyl)pyrimidin-2-yl) pyrrolidin-3-yl carbamate | 1H NMR: (DMSO) δ (ppm): 9.49 (s, 1 H), 8.88 (s, 2 H), 8.57 (d, J = 5.7, 1 H), 7.13 (d, J = 7.6 Hz, 1 H), 6.96 (t, J = 7.6 Hz, 1 H), 6.76 (d, J = 7.0 Hz, 1 H), 6.57 (t, J = 7.7 Hz, 1 H), 4.94 (s, 2 H), 4.17-4.14 (m, 1 H), 3.77-72 (m, 1 H), 3.68-3.59 (m, 2 H), 3.55 (s, 1 H), 3.47-3.44 (m, 3 H), 2.19-2.13 (m, 1 H), 1.94-1.89 (m, 1 H). MS: 356.2 (calc), 356.2 (obs) (MH$^+$). |

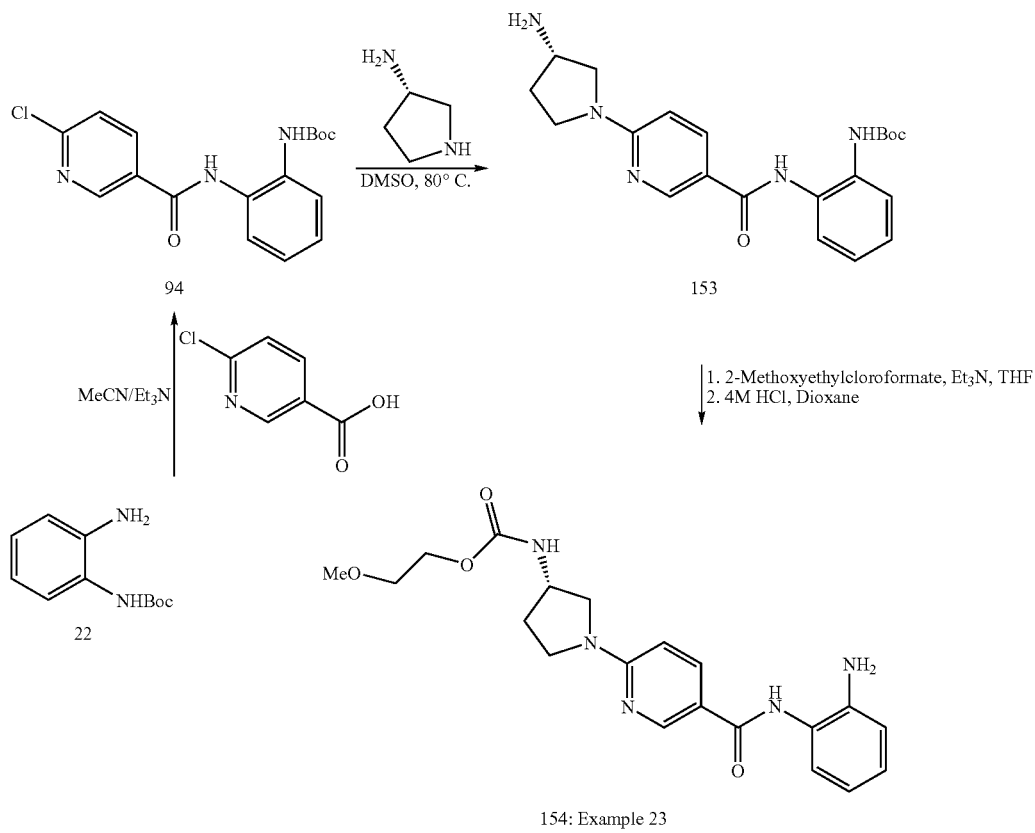

Scheme 4

154: Example 23

Example 23

(S)-2-Methoxyethyl 1-(5-(2-aminophenylcarbamoyl)pyridin-2-yl)pyrrolidin-3-ylcarbamate (154)

Step 1: tert-Butyl 2-(6-chloronicotinamido)phenylcarbamate (94)

To solution of (2-amino-phenyl)-carbamic acid tert-butyl ester (22) (Seto, C. T.; Mathias, J. P.; Whitesides, G. M.; J. Amer. Chem. Soc., (1993), 115, 1321-1329.) (1.56 g, 7.49 mmol) in MeCN (40 mL) is added triethylamine (2.60 mL, 18.7 mmol) and 6-chloronicotinic acid (1.42 g 8.99 mmol). The mixture is stirred for 18 h at r.t. Upon completion of the reaction, the solvent is removed in vacuo and the residue is partitioned between EtOAc and an $NH_4Cl$ solution. The organic phase is collected and the aqueous layer is then extracted with EtOAc; the combined organic layers are washed with brine, dried over $MgSO_4$ and evaporated. The residue is purified by flash chromatography using EtOAc/Hexane (a gradient of 20:80 to 50:50) as an eluent, to afford the title compound 94 (2.39 g, 92% yield). $^1$H NMR (DMSO-$d_6$) δ(ppm): 10.01 (s, 1H), 8.96 (d, J=2.0 Hz, 1H), 8.71 (s, 1H), 8.35 (dd, J=8.4, 2.4 Hz, 1H), 7.73 (d, J=8.0 Hz, 1H), 7.62 (d, J=8.0 Hz, 1H), 7.48 (d, J=7.6 Hz, 1H), 7.22 (td, J=7.8, 1.4 Hz, 1H), 7.13 (t, J=7.6 Hz, 1H), 1.44 (s, 9H). LRMS (ESI): (calc) 347.10 (found) 370.1 (M+Na$^+$).

Step 2 (S)-tert-Butyl 2-(6-(3-aminopyrrolidin-1-yl)nicotinamido)phenylcarbamate (153)

A solution of compound 94 (1.00 g, 2.88 mmol) and 3-(S)(−)aminopyrrolidine (495 mg, 5.75 mmol) in DMSO (5 ml) was heated to 80° C. for 3 h. The reaction mixture was cooled to room temperature and stirred for an additional 16 h and diluted with water. The aqueous solution was extracted with AcOEt/dichloromethane mixture, washed with saturated aqueous $NaHCO_3$ and brine, dried over $MgSO_4$, filtered and concentrated in vacuo to afford the title compound 153 as an orange solid (981 mg, 86% yield). $^1$H NMR: (DMSO) δ (ppm): 8.76 (s, 2H), 4.26 (q, J=7.1 Hz, 2H), 3.70-3.53 (m, 4H), 3.26 (dd, J=11.3, 3.9 Hz, 1H), 2.07-1.98 (m, 1H), 1.75-1.67 (m, 3H), 1.29 (t, J=7.0 Hz, 3H). LRMS (ESI): (calc.) 397.2; (obt.) 398.3 (M+H)$^+$.

Steps 3 and 4: (S)-2-Methoxyethyl 1-(5-(2-aminophenylcarbamoyl)pyridin-2-yl)pyrrolidin-3-ylcarbamate (154)

Following the procedures described above for the synthesis of compound 119 (Scheme 1, Example 1, steps 4 and 5) but replacing compound 117 with the compound 153, and TFA for HCl/dioxane, title compound 154 was obtained as a beige solid. $^1$H NMR: (DMSO) δ (ppm): 9.42 (s, 1H), 8.72 (d, J=2.3 Hz, 1H), 8.05 (dd, J=8.8, 2.3 Hz, 1H), 7.65 (d, J=6.5 Hz, 1H), 7.13 (d, J=7.8 Hz, 1H), 6.95 (td, J=7.6, 1.4 Hz, 1H), 6.77 (dd, J=8.0, 1.2 Hz, 1H), 6.58 (td, J=7.5, 1.4 Hz, 1H), 6.49 (d, J=8.8 Hz, 1H), 4.87 (s, 2H), 4.17 (q, J=5.7 Hz, 1H), 4.08 (t, J=4.6 Hz, 2H), 3.67 (q, J=5.7 Hz, 1H), 3.57-3.55 (m, 1H), 3.50-3.47 (m, 3H). 3.3 (m, overlap with water, 1H), 3.25 (s, 3H), 2.22-2.14 (m, 1H), 1.96-1.88 (m, 1H). LRMS (ESI): (calc.) 399.2; (obt.) 400.3 (M+H)$^+$.

Compounds in Table 5 were prepared using procedures analogous to those described above for compound 154.

TABLE 5

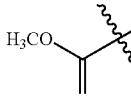

| Ex | Cpd | R | Name | Characterization |
|---|---|---|---|---|
| 24 | 155 | H₃CO-C(=O)-C(CH₃)- | (S)-Methyl 1-(5-(2-aminophenyl-carbamoyl)pyridin-2-yl)pyrrolidin-3-ylcarbamate | ¹H NMR: (DMSO) δ (ppm): 9.42 (s, 1 H), 8.72 (d, J = 2.2, 1 H), 8.05 (dd, J = 8.8, 2.2 Hz, 1 H), 7.55 (d, J = 6.5 Hz, 1 H), 7.14 (d, J = 7.6 Hz, 1 H), 6.95 (t, J = 5.5 Hz, 1 H), 6.77 (d, J = 7.6 Hz, 1 H), 6.58 (t, J = 7.6 Hz, 1 H), 6.50 (d, J = 9.0 Hz, 1 H), 4.87 (s, 2 H), 4.20-4.17 (m, 1 H), 3.70-65 (m, 1 H), 3.56-3.47 (m, 5 H), 3.33-3.31 (m, overlap with water, 1 H), 2.22-2.13 (m, 1 H), 1.94-1.89 (m, 1 H). MS: 355.1 (calc), 356.2 (obs) (MH⁺). |
| 25 | 156 | C₂H₅O-C(=O)-C(CH₃)- | (S)-Ethyl 1-(5-(2-aminophenyl-carbamoyl)pyridin-2-yl)pyrrolidin-3-ylcarbamate | ¹H NMR: (DMSO) δ (ppm): 9.42 (s, 1 H), 8.72 (d, J = 2.3, 1 H), 8.05 (dd, J = 9.0, 2.5 Hz, 1 H), 7.51 (d, J = 6.7 Hz, 1 H), 7.14 (d, J = 7.8 Hz, 1 H), 6.95 (td, J = 7.6, 1.4 Hz, 1 H), 6.77 (dd, J = 7.8, 1.2 Hz, 1 H), 6.59 (td, J = 7.5, 1.2 Hz, 1 H), 6.50 (d, J = 8.8 Hz, 1 H), 4.87 (s, 2 H), 4.17 (q, J = 5.6 Hz, 1 H), 4.00 (q, J = 7.0 Hz, 2 H), 3.68-3.65 (m, 1 H), 3.57-3.55 (m, 1 H), 3.50-3.47 (m, 1 H). 3.3 (m, overlap with water, 1 H), 2.20-2.13 (m, 1 H), 1.96-1.89 (m, 1 H), 1.16 (t, J = 7.0 Hz, 3 H). MS: 369.2 (calc), 370.1 (obs) (MH⁺). |

Scheme 5

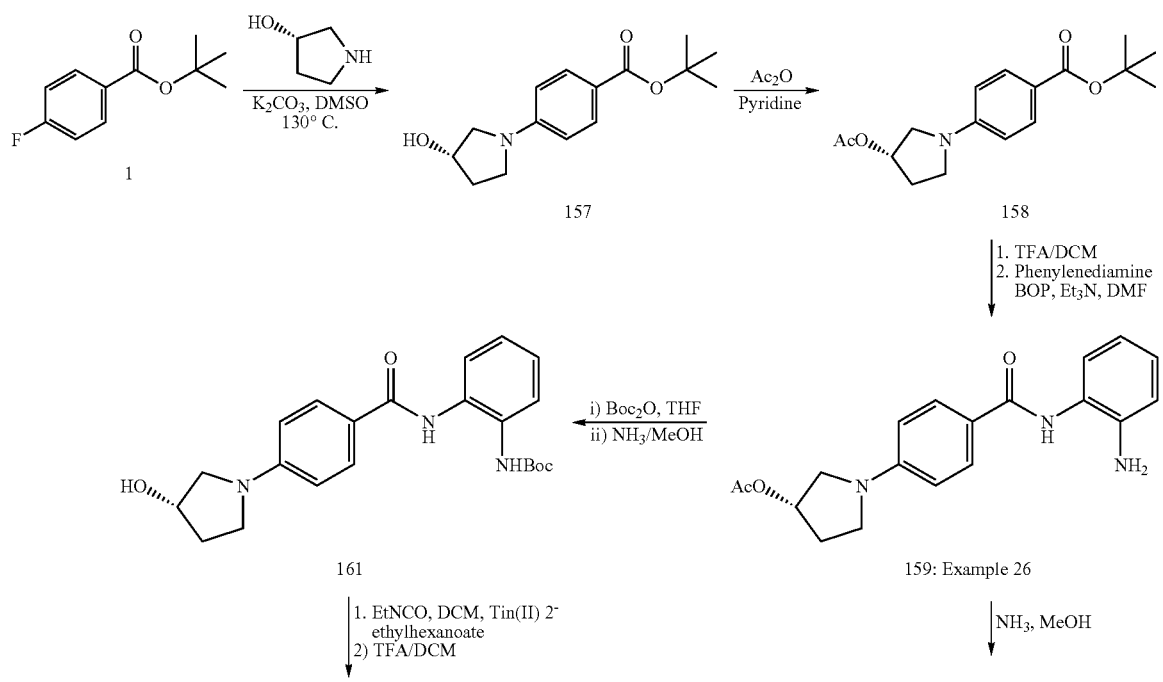

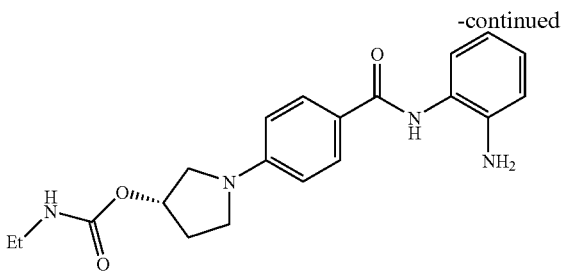

162: Example 28

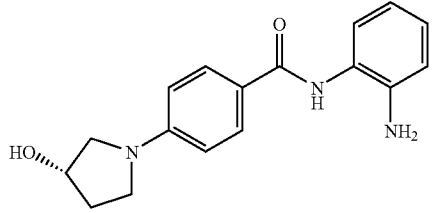

160: Example 27

Example 26

(S)-1-(4-(2-Aminophenylcarbamoyl)phenyl)pyrrolidin-3-yl acetate (159)

Example 27

(S)-N-(2-Aminophenyl)-4-(3-hydroxypyrrolidin-1-yl)benzamide (160)

Example 28

(S)-1-(4-(2-Aminophenylcarbamoyl)phenyl)pyrrolidin-3-yl ethyl carbamate (162)

Step 1: (S)-tert-Butyl 4-(3-hydroxypyrrolidin-1-yl)benzoate (157)

To a solution of tert-butyl 4-fluorobenzoate (1 g, 5.1 mmol) and (S)-pyrrolidin-3-ol (462 mg, 5.3 mmol) in DMSO (10 mL) was added powdered potassium carbonate (705 mg, 5.1 mmol). The mixture was stirred at 130° C. for 4 h and allowed to cool down to room temperature. The mixture was diluted with EtOAc (300 mL) and the solution was washed with water (2×100 mL), dried over $Na_2SO_4$, filtered and concentrated to provide title compound 157 (1.23 g, 88% yield) that was used in the next step without further purification. LRMS (ESI): (calc) 263.15 (found) 264.1 (MH$^+$).

Step 2: (S)-tert-Butyl 4-(3-hydroxypyrrolidin-1-yl)benzoate (158)

To a solution of 157 (1.23 g, 4.67 mmol) in pyridine (20 mL) was added acetic anhydride (10 mL) and the reaction mixture was stirred for 2.5 hrs at r.t. The mixture was then concentrated in vacuo, the residue was re-dissolved in toluene. The toluene solution was evaporated in vacuo, to provide title compound 158 (1.47 g, quant. yield) that was used in the next step without further purification. LRMS (ESI): (calc) 305.16 (found) 306.1 (MH$^+$).

Step 3: (S)-1-(4-(2-Aminophenylcarbamoyl)phenyl)pyrrolidin-3-yl acetate (159)

Title compound 159 was obtained following the same procedures as described for the synthesis of compound 116 (Scheme 1, Example 1, step 2) but substituting compound 115 for compound 158 and compound 22 for benzene-1,2-diamine. $^1$H NMR: (CDCl$_3$) δ(ppm): 7.81 (d, 2H, J=8.8 Hz), 7.74 (s, 1H), 7.25 (d, 1H, J=8.2 Hz), 7.05 (t, 1H, J=8.0 Hz), 6.84 (d, 2H, J=7.4 Hz), 6.56 (d, 2H, J=9.0 Hz), 5.43 (m, 1H), 3.65 (m, 1H), 3.4-3.6 (m, 4H), 2.23 (m, 2H), 2.06 (s, 3H). LRMS (ESI): (calc) 339.16 (found) 340.1 (MH$^+$).

Step 4: (S)-N-(2-Aminophenyl)-4-(3-hydroxypyrrolidin-1-yl)benzamide (160)

Ammonia gas was bubbled into a solution of compound 159 (300 mg, 0.88 mmol) in methanol (10 mL) at 0° C. for 5 min. The reaction mixture was then stirred for 3 hrs at r.t. and concentrated. The residue was purified by flash chromatography using a gradient 75-100% EtOAc in hexanes as an eluent, to afford title compound 160 (135 mg, 51% yield). $^1$H NMR: (MeOH-d4) δ(ppm): 7.91 (s, 1H), 7.86 (d, 2H, J=7.0 Hz), 7.16 (d, 1H, J=7.8 Hz), 7.05 (t, 1H, J=7.2 Hz), 6.89 (d, 1H, J=8.0 Hz), 6.76 (t, 1H, J=7.6 Hz), 6.62 (d, 2H, J=9.0 Hz), 4.56 (m, 1H), 3.54 (m, 2H), 3.46 (m, 1H), 2.98 (s, 1H), 2.85 (s, 1H), 2.17 (m, 1H), 2.05 (m, 1H), LRMS (ESI): (calc): 297.15 (found) 298.1 (MH$^+$).

Step 5: (S)-tert-Butyl 2-(4-(3-hydroxypyrrolidin-1-yl)benzamido)phenylcarbamate (161)

A solution of 159 (3.7 g, 10.9 mmol) and Boc anhydride (3.6 g, 16.4 mmol) in THF (20 mL) was stirred at r.t. for 1 h. The reaction mixture was concentrated and the crude product was purified by flash chromatography using 60% EtOAc in hexanes as an eluent. The material obtained was dissolved in MeOH (20 mL) and ammonia gas was bubbled in. The reaction mixture was allowed to stir overnight and concentrated to provide title compound 161 (2.5 g, 57% yield) that was used in the next step without further purification. LRMS (ESI): (calc) 397.20 (found) 398.1 (MH$^+$).

Step 6: (S)-1-(4-(2-Aminophenylcarbamoyl)phenyl)pyrrolidin-3-yl ethylcarbamate (162)

A solution of 161 (100 mg, 0.25 mmol) and ethyl isocyanate (29 µL, 28 mg, 0.375 mmol) in dichloromethane (5 mL) was treated with tin(II) 2-ethylhexanoate (44 µL, 55 mg, 0.135 mmol). The reaction mixture was stirred overnight at r.t. under nitrogen, concentrated and the residue was purified by flash chromatography using gradient 70 to 90% EtOAc in hexanes as an eluent. The material obtained was then dissolved in 2:1 mixture of dichloromethane and TFA (3 mL), stirred for 30 min and concentrated. The residue was then dissolved in EtOAc (5 mL) and washed with saturated NaHCO$_3$ solution (5 mL), dried over Na$_2$SO$_4$, filtered and concentrated to afford title compound 162 (39 mg, 42% yield). $^1$H NMR: CDCl$_3$ δ(ppm): 7.7 (d J=8.8 Hz, 2H), 7.6 (s, 1H), 7.2 (d, J=7.6 Hz, 1H), 7.0 (t, J=8.8 Hz, 1H), 6.8 (t, J=7.8 Hz, 2H), 6.5 (d, J=8.8 Hz, 2H), 5.3 (s, 1H), 4.6 (s, 1H), 3.9 (s, 2H), 3.6 (m, 1H), 3.4 (m, 3H), 3.1 (m, 2H), 2.2 (m, 2H), 1.2 (s, 1H), 1.1 (m, 3H). LRMS (ESI): (calc) 368.18 (found) 369.1 (MH$^+$).

TABLE 6

Compound 163 (example 29) was prepared using the same procedures as described for compound 162.

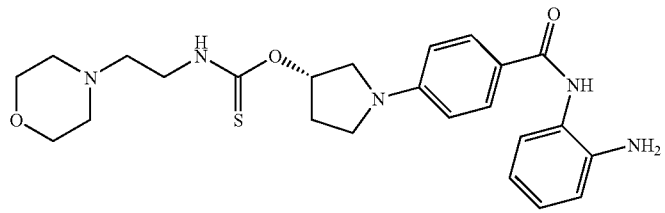

| Ex | Cpd | Name | Characterization |
|---|---|---|---|
| 29 | 163 | (S)-O-1-(4-(2-Aminophenylcarbamoyl)phenyl)pyrrolidin-3-yl 2-morpholinoethyl-carbamothioate | $^1$H NMR: (MeOH-d4) δ (ppm): 7.87 (d, 2 H, J = 8.8 Hz), 7.15 (d, 1 H, J = 7.8 Hz), 7.05 (t, 1 H, J = 8.0 Hz), 6.89 (d, 1 H, J = 8.0 Hz), 6.76 (t, 1 H, J = 7.8 Hz), 6.62 (d, 2 H, J = 9.0 Hz), 4.30 (m, 1 H), 4.19 (m, 2 H), 3.67 (m, 5 H), 3.50 (m, 1 H), 3.43 (m, 1 H), 3.28 (m, 1 H), 2.64 (m, 2 H), 2.52 (br.s, 4 H), 2.31 (m, 1 H), 2.03 (m, 1 H), m/z: 454.1 (MH$^+$). |

Scheme 6

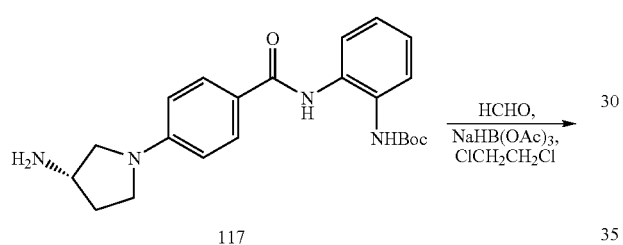

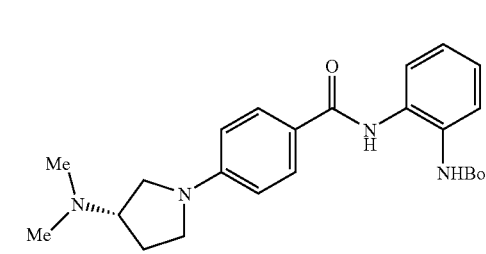

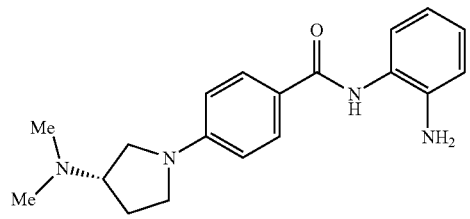

165: Example 30

Example 30

(S)-N-(2-Aminophenyl)-4-(3-(dimethylamino)pyrrolidin-1-yl)benzamide (165)

Step 1: (S)-tert-Butyl 2-(4-(3-(dimethylamino)pyrrolidin-1-yl)benzamido)phenyl carbamate (164)

A solution of 117 (scheme 1) (50 mg, 0.13 mmol) and formaldehyde (40 μL 37% water solution, 0.50 mmol) in 1,2-dichloroethane (1 mL) was treated with NaBH(OAc)$_3$ (82 mg, 0.39 mmol) and stirred for 1 h at room temperature. The reaction mixture was quenched by adding saturated NaHCO$_3$ solution (5 mL) and then extracted with dichloromethane (2×5 mL). The organic extract was dried over Na$_2$SO$_4$, filtered and concentrated. The residue was purified by flash chromatography using 5% MeOH in dichloromethane as an eluent, to provide title compound 164 (40 mg, 75% yield). LRMS (ESI): (calc) 424.25 (found) 425.2 (MH$^+$).

Step 2: (S)-N-(2-Aminophenyl)-4-(3-(dimethylamino)pyrrolidin-1-yl)benzamide (165)

Title compound 165 was obtained in 46% yield by following the same procedure as described above for the synthesis of compound 119 (Scheme 1, Example 1, step 5). The crude product was purified by flash chromatography using 5% MeOH in dichloromethane as an eluent. $^1$H NMR: (MeOH-d4) δ(ppm): 7.87 (d, 2H, J=8.6 Hz), 7.15 (d, 1H, J=7.5 Hz), 7.05 (t, 1H, J=8.0 Hz), 6.89 (d, 1H, J=8.0 Hz), 6.76 (t, 1H, J=7.4 Hz), 6.63 (d, 2H, J=8.8 Hz), 3.62 (t, 1H, J=7.6 Hz), 3.54 (t, 1H, J=7.4 Hz), 3.36 (m, 1H), 3.20 (t, 1H, J=8.4 Hz), 2.96 (m, 1H), 2.35 (m, 7H), 2.17 (m, 1H), 1.95 (m, 1H). LRMS (ESI): (calc) 324.2 (found): 325.1 (MH$^+$).

Using procedures analogous to those outlined above, the compounds in Table 7 were also prepared.

TABLE 7

| Ex. No. | Cpd. No. | Name | Structure |
| --- | --- | --- | --- |
| 31 | 194 | (S)-N-(2-Aminophenyl)-4-(3-(phenylmethyl-sulfonamido)pyrrolidin-1-yl)benzamide | 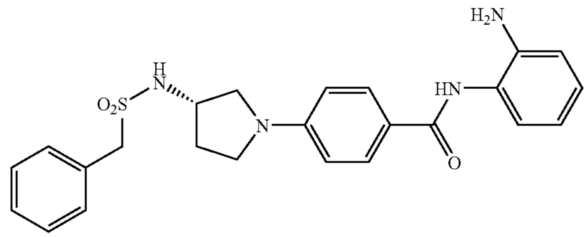 |
| 32 | 195 | (S)-2-morpholinoethyl 1-(4-(2-aminophenylcarbamoyl)-phenyl)pyrrolidin-3-ylcarbamate | 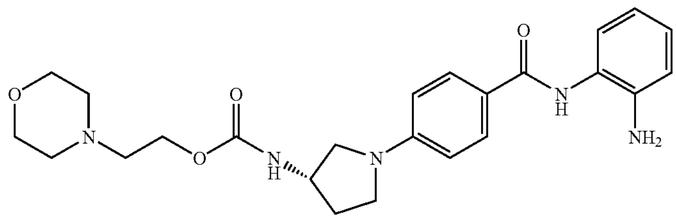 |
| 33 | 196 | (S)-methyl 1-(4-(2-aminophenylcarbamoyl)phenyl)-pyrrolidin-3-yl(pyridin-3-ylmethyl)carbamate | 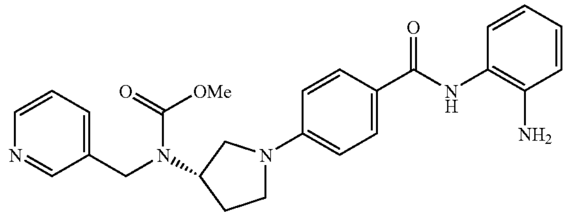 |
| 34 | 197 | (S)-benzyl 1-(4-(2-aminophenylcarbamoyl)phenyl)-pyrrolidin-3-yl(3,4,5-trimethoxybenzyl)carbamate | 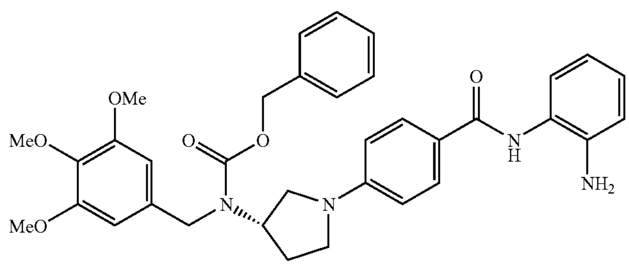 |
| 35 | 198 | (S)-isopropyl 1-(4-(2-aminophenylcarbamoyl)phenyl)-pyrrolidin-3-ylcarbamate | 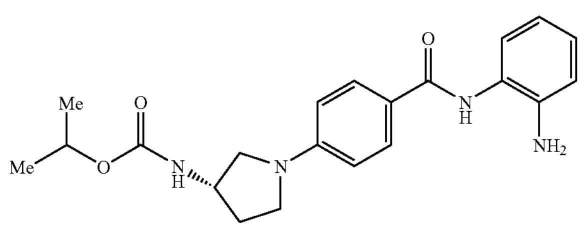 |
| 36 | 199 | (S)-cyclopropylmethyl 1-(4-(2-aminophenylcarbamoyl)phenyl)-pyrrolidin-3-ylcarbamate | 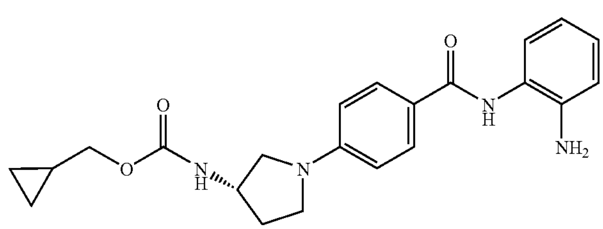 |

TABLE 7-continued

| | | | |
|---|---|---|---|
| 37 | 200 | (S)-tetrahydro-2H-pyran-4-yl 1-(4-(2-aminophenylcarbamoyl)phenyl)-pyrrolidin-3-ylcarbamate | |
| 38 | 201 | (S)-(9H-fluoren-9-yl)methyl 1-(4-(2-aminophenylcarbamoyl)-phenyl)pyrrolidin-3-ylcarbamate | |

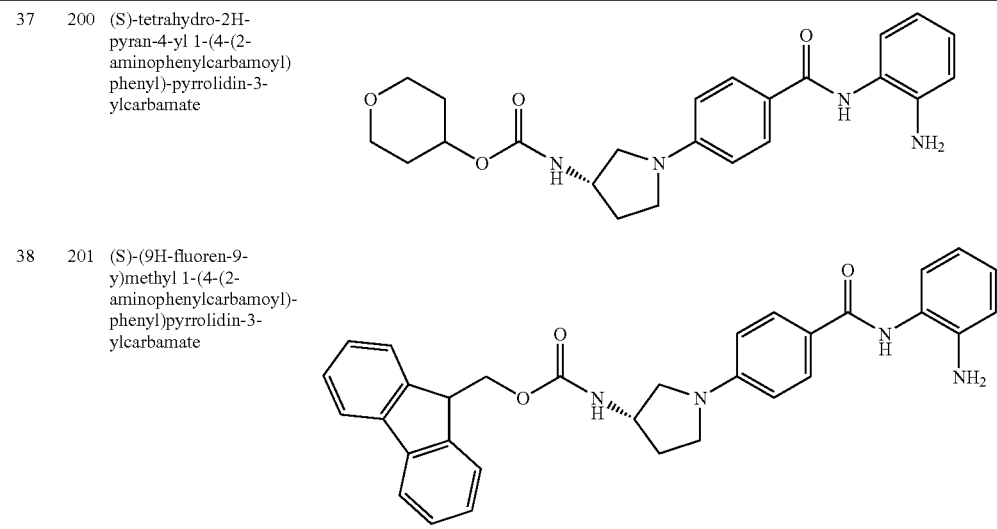

| Ex. No. | Reference scheme | Characterization |
|---|---|---|
| 31 | 1 and 3 | $^1$H NMR: (DMSO) δ (ppm): 9.38 (s, 1 H), 7.86 (d, J = 8.8 Hz, 2 H), 7.41-7.35 (m, 5 H), 7.14 (d, J = 7.8 Hz, 1 H), 6.94 (td, J = 7.5, 1.4 Hz, 1 H), 6.77 (dd, J = 8.0, 1.4 Hz, 1 H), 6.61-6.551 (m, 3 H), 4.83 (s, 2 H), 4.42 (s, 2 H), 4.01-3.98 (m, 1 H), 3.54-3.50 (m, 1 H), 3.42-3.39 (m, 1 H), 3.31-3.25 (m, 1 H), 3.15-3.11 (m, 1 H), 2.24-2.19 (m, 1 H), 1.99-1.90 (m, 1 H). MS: 450.2 (calc), 451.0 (found) (MH$^+$). |
| 32 | 1 | $^1$H NMR: (MeOH-d4) δ (ppm): 7.86 (d, 2 H, J = 8.8 Hz), 7.15 (dd, 1 H, J = 1.4 Hz, J = 7.9 Hz), 7.05 (m, 1 H), 6.89 (dd, 1 H, J = 1.4 Hz, J = 8.0 Hz), 6.76 (dt, 1 H, 1.4 Hz, J = 7.8 Hz), 6.61 (d, 2 H, J = 9.0 Hz), 4.29 (m, 1 H), 4.18 (m, 2 H), 3.2-3.7 (m, 10 H), 2.63 (m, 2 H), 2.52 (br.s, 4 H), 2.30 (m, 1 H), 2.03 (m, 1 H). MS 453.2 (calc), 454.1 (found) (MH$^+$) |
| 33 | 1 | $^1$H NMR: (DMSO-d6) δ (ppm): 9.34 (s, 1 H), 8.45 (d, J = 1.6 Hz, 2 H), 7.82 (d, J = 9.0 Hz, 2 H), 7.63 (d, J = 8.0 Hz, 1 H), 7.36 (ddd, J = 7.8, 2.9, 0.8 Hz, 1 H), 7.11 (dd, J = 7.4, 1.4 Hz, 1 H), 6.92 (td, J = 8.0, 1.6 Hz, 1 H), 7.75 (dd, J = 7.8, 1.4 Hz, 1 H), 6.57 (td, J = 7.6, 1.4 Hz, 1 H), 6.52 (d, J = 8.8 Hz, 2 H), 4.81 (s, 2 H), 4.75 (quint, J = 9.0 Hz, 1 H), 4.55 (d, J = 16.8 Hz, 1 H), 4.50 (d, J = 16.8 Hz, 1 H), 3.64 (s, 3 H), 3.48 (dd, J = 9.6, 8.0 Hz, 1 H), 3.43-3.37 (m, 1 H), 3.30-3.21 (m, 2 H), 2.13-2.06 (m, 2 H). MS. 445.52 (calc), 446.1 (found) (MH$^+$). |
| 34 | 1 | MS. 610.3 (calc.), 611.4 (found) (MH)+ |
| 35 | 1 | $^1$H NMR: (DMSO-d6) δ (ppm): 9.36 (s, 1 H), 7.85 (d, J = 8.8 Hz, 2 H), 7.44 (d, J = 6.8 Hz, 1 H), 7.14 (dd, J = 7.8, 1.4 Hz, 1 H), 6.94 (td, J = 7.5, 1.2 Hz, 1 H), 6.77 (dd, J = 8.0, 1.2 Hz, 1 H), 6.59 (td, J = 7.5, 1.6 Hz, 1 H), 6.56 (d, J = 8.8 Hz, 2 H), 4.82 (bs, 2 H), 4.77 (pent, J = 6.3 Hz, 1 H), 4.19 (q, J = 5.9 Hz, 1 H), 3.54 (dd, J = 10.0, 6.4 Hz, 1 H), 3.43 (m, 1 H), 3.31 (m, 1 H), 3.13 (dd, J = 10.0, 4.8 Hz, 1 H), 2.18 (sext, J = 6.6 Hz, 1 H), 1.92 (sext, J = 6.5 Hz, 1 H), 1.17 (dd, J = 6.2, 3.4 Hz, 6 H). (calc.) MS. (calc) 382.20, (found) 383.3 (MH)+ |
| 36 | 1 | $^1$H NMR: (DMSO-d6) δ (ppm): 9.36 (s, 1 H), 7.86 (d, J = 8.8 Hz, 2 H), 7.57 (d, J = 6.8 Hz, 1 H), 7.14 (dd, J = 8.0, 1.6 Hz, 1 H), 6.94 (td, J = 7.6, 1.3 Hz, 1 H), 6.77 (dd, J = 8.0, 1.6 Hz, 1 H), 6.60 (dd, J = 7.8, 1.2 Hz, 1 H), 6.56 |

TABLE 7-continued

| | | |
|---|---|---|
| | | (d, J = 8.8 Hz, 2 H), 4.82 (s, 2 H), 4.20 (sext, J = 6.0 Hz, 1 H), 3.79 (d, J = 7.2 Hz, 2 H), 3.45 (dd, J = 10.0, 6.4 Hz, 1 H), 3.44 (m, 1 H), 3.30 (m, 1 H), 3.16 (dd, J = 10.0, 5.2 Hz, 1 H), 2.19 (sext, J = 6.5 Hz, 1 H), 1.93 (sext, J = 6.4 Hz, 1 H), 1.05 (m, 1 H), 0.49 (m, 2 H), 0.25 (m, 2 H). MS. (calc.) 394.20 (found) 395.3 (MH)+ |
| 37 | 1 | ¹H NMR: (DMSO-d6) δ (ppm): 9.36 (s, 1 H), 7.86 (d, J = 8.8 Hz, 2 H), 7.57 (d, J = 6.8 Hz, 1 H), 7.14 (dd, J = 8.0, 1.6 Hz, 1 H), 6.94 (td, J = 7.4, 1.6 Hz, 1 H), 6.77 (dd, J = 8.0, 1.2 Hz, 1 H), 6.59 (td, J = 7.6, 1.6 Hz, 1 H), 6.56 (d, J = 8.8 Hz, 2 H), 4.82 (s, 2 H), 4.71 (sept, J = 4.4 Hz, 1 H), 4.20 (sext, J = 6.0 Hz, 1 H), 3.80 (m, 2 H), 3.55 (dd, J = 10.0, 6.4 Hz, 1 H), 3.44 (m, 3 H), 3.30 (m, 1 H), 3.15 (dd, 10.0, 4.8 Hz, 1 H), 2.19 (sext, 6.6 Hz, 1 H), 1.93 (sext, J = 6.5 Hz, 1 H), 1.86 (m, 2 H), 1.53-1.45 (m, 2 H). MS (calc.) 424.21, (found) 425.2 (MH)+ |
| 38 | 1 | ¹H NMR: (MeOH-d4) δ (ppm): 7.87 (d, J = 8.0 Hz, 2 H), 7.77 (d, J = 7.0 Hz, 2 H), 7.63 (d, J = 7.0 Hz, 2 H), 7.49 (d, J = 5.5 Hz, 1 H), 7.37 (t, J = 6.7 Hz, 2 H), 7.31-7.27 (m, 2 H), 7.16 (d, J = 7.6 Hz, 1 H), 7.06 (t, J = 7.4 Hz, 1 H), 6.90 (d, J = 8.0 Hz, 1 H), 6.77 (t, J = 7.4 Hz, 1 H), 6.59 (d, J = 8.2 Hz, 2 H), 4.38 (d, J = 5.9 Hz, 2 H), 4.29-4.26 (m, 1 H), 4.20-4.16 (m, 1 H), 3.60-3.57 (m, 1 H), 3.51-3.43 (m, 1 H), 3.40-3.32 (m, 1 H), 3.23-3.19 (m, 1 H), 2.28-2.21 (m, 1 H), 2.20-1.97 (m, 1 H). MS (calc.) 518.61, (found) 519.3 (MH)+ |

Scheme 7

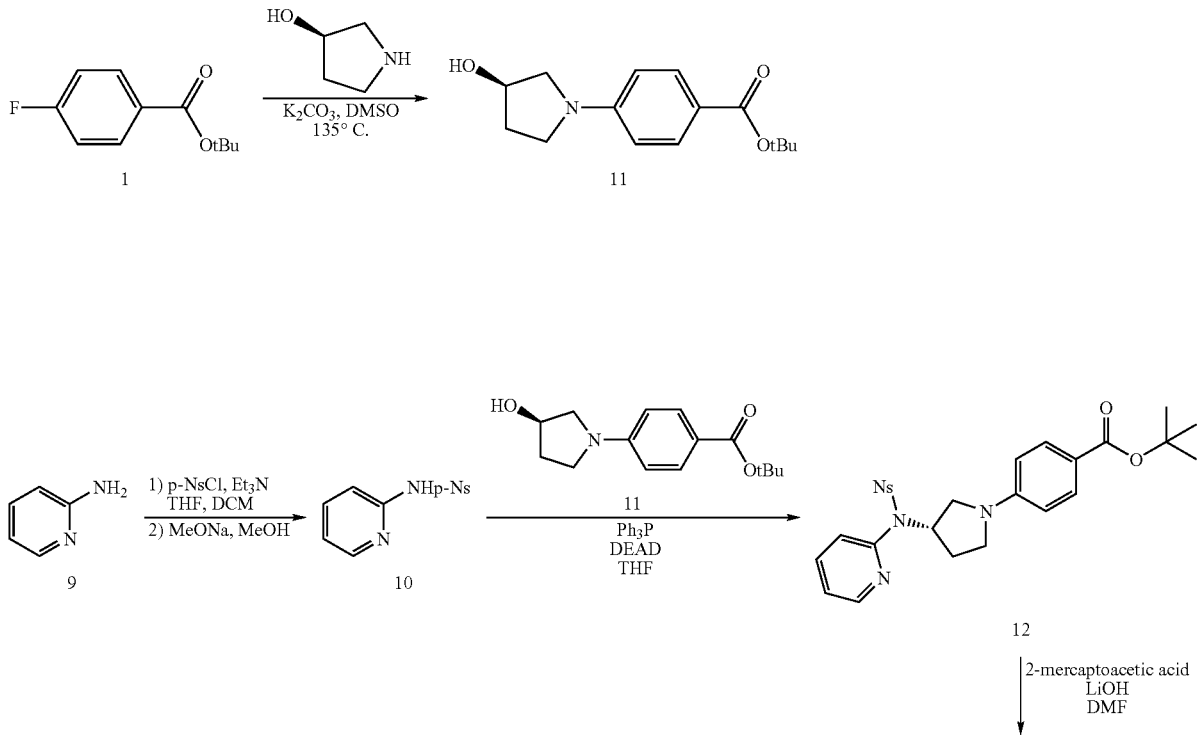

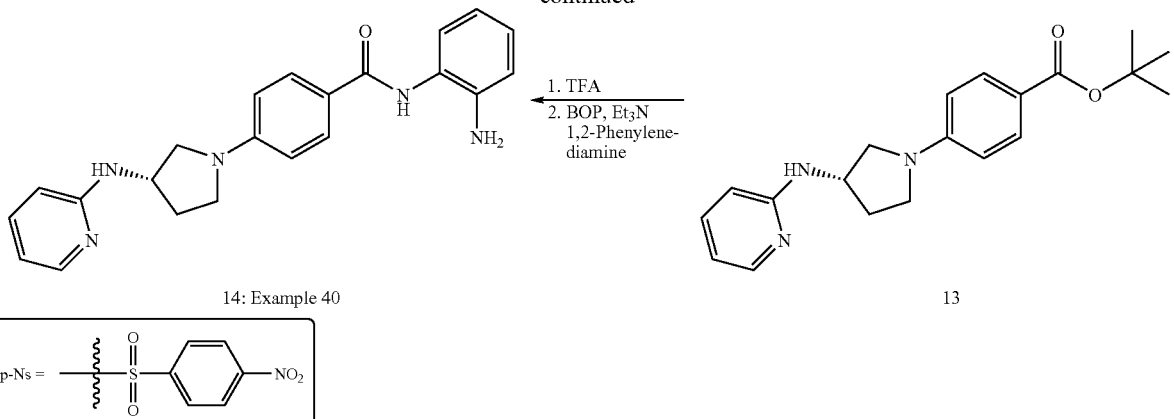

14: Example 40 p-Ns = (4-nitrobenzenesulfonyl group)

Example 40

(S)-N-(2-Aminophenyl)-4-(3-(pyridin-2-ylamino)pyrrolidin-1-yl)benzamide (14)

Step 1a: (R)-tert-Butyl 4-(3-hydroxypyrrolidin-1-yl)benzoate (11)

Title compound II was obtained in 91% yield by following the procedure described above for the synthesis of compound 157 (scheme 5, step 1) but substituting (S)-hydroxypyrrolidine for (R)-3-hydroxypyrrolidine. $^1$H NMR (DMSO-d$_6$) δ(ppm): 7.69 (d, J=8.8 Hz, 2H), 6.51 (d, J=8.8 Hz, 2H), 5.02 (d, J=2.4 Hz, 1H), 4.40 (bs, 1H), 3.43 (dd, J=10.6, 4.6 Hz, 1H), 3.37 (m, 1H), 3.32 (m, 1H), 3.14 (d, J=10.8, 1H), 2.03 (m, 1H), 1.91 (m, 1H), 1.50 (s, 9H). LRMS (ESI): (calc) 263.15 (found) 264.1 (MH$^+$).

Step 1: 4-Nitro-N-(pyridin-2-yl)benzenesulfonamide (10)

To a stirring solution of 2-aminopyridine 9 (2.00 g, 21.3 mmol) in THF (45 mL) were successively added dichloromethane (88 mL), 4-nitrobenzenesulfonyl chloride (9.89 g, 44.6 mmol), and triethylamine (6.51 mL, 46.75 mmol). The solution was heated to reflux for 2 h and the resultant light yellow solid was collected by filtration. This material was suspended in 200 mL of methanol and a large excess (>10 eq) of sodium methoxide was added. The mixture was stirred at r.t. for 6 h, treated with HCl 1N (2 mL) and concentrated in vacuo at 80° C. to 50 mL volume. This solution was transferred into an Erlenmeyer flask and further neutralized with 1N HCl. A precipitate was formed which was collected by filtration, washed with water and dried, to afford the title compound 10 (2.8 g, 47% yield). $^1$H NMR (DMSO-d$_6$) δ (ppm): 8.32 (d, J=6.8 Hz, 2H), 8.07 (d, J=7.0 Hz, 2H), 7.92 (bs, 1H), 7.80 (bs, 1H), 7.26 (bs, 1H), 6.85 (bs, 1H). LRMS (ESI): (calc) 279.03 (found) 280.0 (MH$^+$).

Step 2: (S)-tert-Butyl 4-(3-(4-nitro-N-(pyridin-2-yl)phenylsulfonamido)pyrrolidin-1-yl)benzoate (12)

To a suspension of compound 10 (2.54 g, 9.11 mmol) in THF (45 mL), were successively added compound II (2.64 g, 10.03 mmol), triphenylphosphine (3.11 g, 11.84 mmol) and diethyl azodicarboxylate (1.72 mL, 10.93 mmol). The mixture was stirred at 0° C. for 2 h and at r.t. for an additional 2 h and then treated with excess of both triphenylphosphine (3.11 g, 11.84 mmol) and diethyl azodicarboxylate (1.72 mL, 10.93 mmol). After stirring for 16 h another portion of diethyl azodicarboxylate (1.72 mL, 10.93 mmol) was added and the solution was stirred for 4 h at r.t. The solvent was removed in vacuo and the residue was partitioned between EtOAc and H$_2$O. The organic layer was collected, dried over MgSO$_4$ and concentrated in vacuo. The residue was purified by flash chromatography using EtOAc/Hex (30:70) to afford the title compound 12 (1.60 g, 33% yield). $^1$H NMR (DMSO-d$_6$) δ(ppm): 8.50 (d, J=9.0 Hz, 2H), 8.46 (dd, J=3.5, 1.2 Hz, 1H), 8.21 (d, J=9.0 Hz, 2H), 7.98 (dd, J=7.6, 2.0 Hz, 1H), 7.69 (d, J=9.0 Hz, 2H), 7.54 (d, J=8.0 Hz, 1H), 7.50 (ddd, J=7.4, 4.9, 1.0 Hz, 1H), 6.41 (d, J=9.0 Hz, 2H), 4.95 (quint, J=5.7 Hz, 1H), 3.63 (dd, J=10.6, 7.2 Hz, 1H), 3.49 (dd, J=10.6, 5.9 Hz, 1H), 3.18 (q, J=8.0 Hz, 1H), 2.96 (sext, J=5.7 Hz, 1H), 2.25 (sext, J=7.0 Hz, 1H), 2.02-1.96 (m, 1H), 1.63 (s, 9H). LRMS (ESI): (calc) 524.17 (found) 525.0 (MH$^+$).

Step 3: (S)-tert-Butyl 4-(3-(pyridin-2-ylamino)pyrrolidin-1-yl)benzoate (13)

To a solution of compound 12 (1.41 g, 2.68 mmol) in DMF (13 mL), were successively added lithium hydroxide (382 mg, 9.09 mmol) and thioglycolic acid (274 μL, 3.94 mmol). The mixture was stirred for 18 h at r.t., the solvent was removed in vacuo at 80° C. and the residue was partitioned between EtOAc and H$_2$O. The organic layer was collected, washed with brine, dried over MgSO$_4$, and concentrated in vacuo. The residue was purified by flash chromatography using EtOAc/Hexanes (40:60) as an eluent, to afford the title compound 13 (511 mg, 47% yield) as a light yellow oil. $^1$H NMR: (DMSO-d$_6$) d (ppm): 7.98 (dd, J=5.5, 1.6 Hz, 1H), 7.68 (d, J=8.8 Hz, 2H), 7.35 (td, J=7.0, 2.0 Hz, 1H), 6.80 (d, J=6.3 Hz, 1H), 6.52 (d, J=9.0 Hz, 2H), 6.49-6.46 (m, 2H), 4.52-4.49 (m, 1H), 3.64 (dd, J=10.5, 6.5 Hz, 1H), 3.48-3.44 (m, 1H), 3.39-3.33 (m, 1H), 3.16 (dd, J=10.0, 4.5 Hz, 1H), 2.30-2.24 (m, 1H), 2.00-2.19 (m, 1H), 1.48 (s, 9H). LRMS (ESI): (calc.) 339.19; (found) 340.1 (MH)+

Steps 4 and 5: (S)-N-(2-Aminophenyl)-4-(3-(pyridin-2-ylamino)pyrrolidin-1-yl)benzamide (14)

Title compound 14 was obtained in 36% yield following the same procedures as described in Scheme 2, example 14 (steps 2 and 3) but substituting compound 139 for compound 13. $^1$H NMR: (DMSO-d$_6$) δ(ppm): 9.33 (s, 1H), 7.99 (dd, J=4.3, 0.4 Hz, 1H), 7.84 (d, J=8.8 Hz, 2H), 7.37 (td, J=7.6, 2.2 Hz, 1H), 7.13 (d, J=6.8 Hz, 1H), 6.92 (t, J=6.8 Hz, 1H), 6.81 (bs, 1H), 6.75 (d, J=8.0 Hz, 1H), 6.58 (d, J=5.5 Hz, 1H), 6.57 (d, J=8.8 Hz, 2H), 6.49 (d, J=7.6 Hz, 2H), 4.81 (bs, 2H), 4.51 (sext, J=4.7 Hz, 1H), 3.66 (dd, J=10.2, 6.3 Hz, 1H), 3.49 (q, J=8.8 Hz, 1H), 3.39-3.32 (m, 1H), 3.18 (dd, J=10.0, 4.1 Hz, 1H), 2.31-2.26 (m, 1H), 2.00-1.97 (m, 1H). LRMS (ESI): (calc) 373.19 (found) 374.1 (MH+).

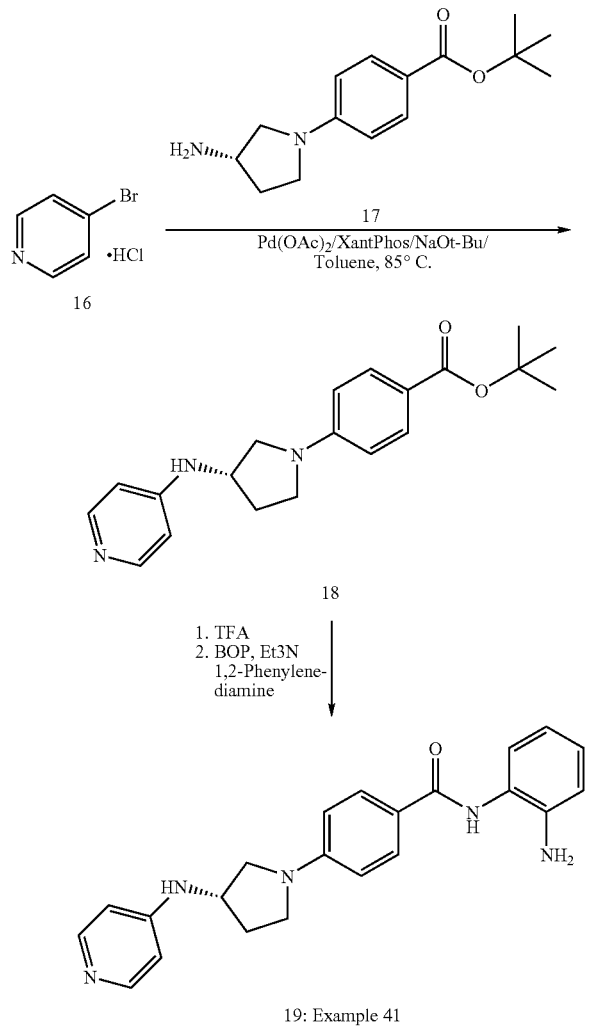

Example 41

(S)-N-(2-aminophenyl)-4-(3-(pyridin-4-ylamino) pyrrolidin-1-yl)benzamide

Step 11: (S)-tert-Butyl 4-(3-(pyridin-4-ylamino)pyrrolidin-1-yl)benzoate (18)

Staring from 4-bromopyridine hydrochloride (16) (356 mg, 1.83 mmol) and compound 17 (400 mg, 1.52 mmol) title compound 18 was obtained (398 mg, 77% yield) according to the known procedure (Harris, M. C.; Geis, O.; Buchwald, S. L.*; *J. Org. Chem.*, 1999, 64, 6019-6022). ¹H NMR: (DMSO-d₆) δ(ppm): 8.58 (d, J=6.5 Hz, 1H), 8.18 (d, J=6.5 Hz, 2H), 7.72 (d, J=8.8 Hz, 2H), 6.91 (d, J=6.8 Hz, 2H), 6.58 (d, J=9.0 Hz, 2H), 4.46-4.40 (m, 1H), 3.71 (dd, J=10.6, 6.3 Hz, 1H), 3.48 (dt, J=9.6, 7.6 Hz, 1H), 4.42 (td, J=9.8, 4.9 Hz, 1H), 3.27 (dd, J=10.4, 3.3 Hz, 1H), 2.35 (sext, J=7.2 Hz, 1H), 2.05-1.98 (m, 1H), 1.50 (s, 9H). LRMS (ESI): (calc) 339.19 (found) 340.2 (MH+).

Steps 2 and 3: (S)-N-(2-Aminophenyl)-4-(3-(pyridin-4-ylamino)pyrrolidin-1-yl)benzamide (19)

The title compound 19 was obtained by following the same procedures as described in Scheme 7, example 40 (steps 4 and 5) but substituting compound 13 for compound 18. ¹H NMR: (DMSO-d6) d (ppm): 9.36 (s, 1H), 8.04 (d, J=6.3 Hz, 2H), 7.86 (d, J=8.6 Hz, 2H), 7.14 (d, J=8.2 Hz, 1H), 6.93 (t, J=7.4 Hz, 1H), 6.81 (d, J=6.8 Hz, 1H), 6.76 (d, J=8.2 Hz, 1H), 6.61-6.55 (m, 5H), 4.82 (s, 2H), 4.24-4.18 (m, 1H), 3.68 (dd, J=10.2, 5.3 Hz, 1H), 3.52-3.36 (m, 2H), 3.19 (d, J=6.3 Hz, 1H), 2.35-2.28 (m, 1H), 2.01-1.93 (m, 1H). LRMS (ESI): (calc) 373.19 (found) 374.1 (MH+).

Compound 14 (example 40) also can be obtained similarly to the compound 19 (example 41) according to the scheme 8.

Assay Examples

Assay Example I

Inhibition of Histone Deacetylase Enzymatic Activity

Inhibition of Histone Deacetylase Enzymatic (HDAC-1) Activity

The following protocol is used to assay the compounds of the invention. In the assay, the buffer used is 25 mM HEPES, pH 8.0, 137 mM NaCl, 2.7 mM KCl, 1 mM MgCl₂ and the substrate is Boc-Lys(Ac)-AMC in a 50 mM stock solution in DMSO. The enzyme stock solution is 4.08 μg/mL in buffer.

The compounds are pre-incubated (2 μl in DMSO diluted to 13 μl in buffer for transfer to assay plate) with enzyme (20 μl of 4.08 μg/ml) for 10 minutes at room temperature (35 μl pre-incubation volume). The mixture is pre-incubated for 5 minutes at room temperature. The reaction is started by bringing the temperature to 37° C. and adding 15 μl substrate. Total reaction volume is 50 μl. The reaction is stopped after 20 minutes by addition of 50 μl developer, prepared as directed by Biomol (Fluor-de-Lys developer, Cat. # KI-105). A plate is incubated in the dark for 10 minutes at room temperature before reading (λ_{Ex}=360 nm, λ_{Em}=470 nm, Cutoff filter at 435 nm). Similar assays are performed to measure HDAC-2 inhibitory activity Assay Example II MTT Assay HCT116 cells (2000/well) are plated into 96-well tissue culture plates one day before compound treatment. Representative compounds at various concentrations were added to the cells. The cells are incubated for 72 hours at 37° C. in 5% CO₂ incubator. MTT (3-[4,5-dimethylthiazol-2-yl]-2,5 diphenyl tetrazolium bromide, Sigma) is added at a final concentration of 0.5 mg/ml and incubated with the cells for 4 hours before one volume of solubilization buffer (50% N,N-dimethylformamide, 20% SDS, pH 4.7) is added onto the cultured cells. After overnight incubation, solubilized dye is quantified by calorimetric reading at 570 nM using a reference at 630 nM. OD values are converted to cell numbers according to a standard growth curve of the relevant cell line. The concentration which reduces cell numbers to 50% of that of solvent treated cells is determined as MTT IC$_{50}$. A similar assay is performed on HMEC cells.

IC$_{50}$ values for these assays are presented in Table 8. In Table 8, "a" indicates activity of ≦0.1 μM, "b" indicates activity of ≦0.5 μM, "c" indicates activity of ≦1 μM, "d" indicates activity of ≦5 μM, "e" indicates activity of ≦10 μM, "f" indicates activity of ≦50 μM, and "g" indicates activity of >50 μM.

| Example No. | Compound No. | IC$_{50}$ HDAC-1 | IC$_{50}$ HDAC-2 | IC$_{50}$ MTT HCT116 | IC$_{50}$ MTT HMEC |
|---|---|---|---|---|---|
| 1 | 119 | b | b | c | g |
| 2 | 120 | b | b | — | g |
| 3 | 121 | b | b | c | f |
| 4 | 122 | b | b | c | f |
| 5 | 123 | b | d | b | f |
| 6 | 124 | b | a | — | d |
| 7 | 126 | b | c | c | g |
| 8 | 127 | c | d | d | g |
| 9 | 128 | d | c | d | f |
| 10 | 129 | — | — | c | f |
| 11 | 130 | d | d | d | — |
| 12 | 131 | b | d | c | — |
| 13 | 135 | a | b | b | e |
| 14 | 140 | b | b | c | e |
| 15 | 141 | b | d | d | g |
| 16 | 142 | a | b | c | f |
| 17 | 143 | b | b | c | f |
| 18 | 144 | b | b | c | — |
| 19 | 145 | a | b | b | f |
| 20 | 146 | b | b | d | — |
| 21 | 151 | c | — | f | — |
| 22 | 152 | c | — | e | — |
| 23 | 154 | b | d | d | — |
| 24 | 155 | b | d | d | f |
| 25 | 156 | b | c | c | f |
| 26 | 159 | b | c | — | — |
| 27 | 160 | c | c | — | — |
| 28 | 162 | b | d | d | g |
| 29 | 163 | b | d | d | f |
| 30 | 165 | c | d | — | — |
| 32 | 195 | b | c | d | — |
| 33 | 196 | b | b | d | — |
| 34 | 197 | b | b | c | g |
| 35 | 198 | b | b | c | f |
| 36 | 199 | a | b | b | f |
| 37 | 200 | b | b | b | g |
| 38 | 201 | a | b | — | — |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:
1. A compound of formula (1):

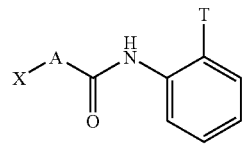

(1)

or an N-oxide, hydrate, solvate, pharmaceutically acceptable salt, complex or prodrug thereof, or a racemic or scalemic mixture, diastereomer, enantiomer or tautomer thereof, wherein
T is NH$_2$ or OH;
A is arylene, which is optionally substituted; and
X is

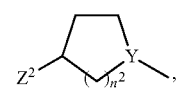

(b)

(a) wherein
Y=N or CH,
n$^2$=0 or 2-4 and
Z$^2$ is selected from the group consisting of R$^{15}$—, R$^{15}$—C(O)—, R$^{13}$—C(S)—, R$^{15}$—N(R$^2$)—, R$^{15}$—O—, R$^{15}$—S—, R$^{15}$—S(O)$_{1-2}$, R$^{15}$—C(O)—O—, R$^{15}$—O—C(O)—, R$^{15}$—C(O)—S—, R$^{15}$—S—C(O)—, R$^{15}$—C(O)—N(R$^2$)—, R$^{15}$—N(R$^2$)—C(O)—, R$^{15}$—C(S)—O—, R$^{15}$—O—C(S)—, R$^{15}$—C(S)—S—, R$^{15}$—S—C(S)—, R$^{15}$—C(S)—N(R$^2$)—, R$^{15}$—N(R$^2$)—C(S)—, R$^{15}$—O—C(O)—O—, R$^{15}$—O—C(O)—S—, R$^{15}$—S—C(O)—O—, R$^{15}$—O—C(O)—N(R$^2$)—, R$^{15}$—N(R$^2$)—C(O)—O—, R$^{15}$—O—C(S)—O—, R$^{15}$—O—C(S)—S—, R$^{15}$—S—C(S)—O—, R$^{15}$—O—C(S)—N(R$^2$)—, R$^{15}$—N(R$^2$)—C(S)—O—, R$^{15}$—S—C(O)—S—, R$^{15}$—S—C(O)—N(R$^2$)—, R$^{15}$—N(R$^2$)—C(O)—S—, R$^{15}$—S—C(S)—S—, R$^{15}$—N(R$^2$)—C(O)—N(R$^2$)—, R$^{15}$—N(R$^2$)—C(S)—N(R$^2$)—, R$^{15}$—N(R$^2$)—C(S)—S—, R$^{15}$—S—C(S)—N(R$^2$)—, R$^{15}$—NH—C(N(R$^2$))—NH—, R$^{15}$—S(O)$_{0-2}$—N(R$^2$)—, R$^{15}$—N(R$^2$)—S(O)$_{0-2}$— and R$^{15}$—N(R$^2$)—S(O)$_{0-2}$—N(R$^2$)—;

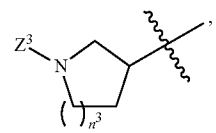

(c)

(b) wherein
n$^3$=0-4 and
Z$^3$ is selected from the group consisting of R$^{15}$—, R$^{15}$—C(O)—, R$^{13}$—C(S)—, R$^{15}$—N(R$^2$)—, R$^{15}$—O—, R$^{15}$—S—, R$^{15}$—S(O)$_{1-2}$, R$^{15}$—C(O)—O—, R$^{15}$—O—C(O)—, R$^{15}$—C(O)—S—, R$^{15}$—S—C(O)—, R$^{15}$—C(O)—N(R$^2$)—, R$^{15}$—N(R$^2$)—C(O)—, R$^{15}$—C(S)—O—, R$^{15}$—O—C(S)—, R$^{15}$—C(S)—S—, R$^{15}$—S—C(S)—, R$^{15}$—C(S)—N(R$^2$)—, R$^{15}$—N(R$^2$)—C(S)—, R$^{15}$—O—C(O)—O—, R$^{15}$—O—C(O)—S—, R$^{15}$—S—C(O)—O—, R$^{15}$—O—C(O)—N(R$^2$)—, R$^{15}$—N(R$^2$)—C(O)—O—, R$^{15}$—O—C(S)—O—, R$^{15}$—O—C(S)—S—, R$^{15}$—S—C(S)—O—, R$^{15}$—O—C(S)—N(R$^2$)—, R$^{15}$—N(R$^2$)—C(S)—O—, R$^{15}$—S—C(O)—S—, R$^{15}$—S—C(O)—N(R$^2$)—, R$^{15}$—N(R$^2$)—C(O)—S—, R$^{15}$—S—C(S)—S—, R$^{15}$—N(R$^2$)—C(O)—N(R$^2$)—, R$^{15}$—N(R$^2$)—C(S)—N(R$^2$)—, R$^{15}$—N(R$^2$)—C(S)—S—, R$^{15}$—S—C(S)—N(R$^2$)—, R$^{15}$—NH—C(N(R$^2$))—NH—, R$^{15}$—S(O)$_{0-2}$—N(R$^2$)—, R$^{15}$—N(R$^2$)—S(O)$_{0-2}$— and R$^{15}$—N(R$^2$)—S(O)$_{0-2}$—N(R$^2$)—, with the proviso that if n$^3$ is 2 and A is phenyl, then Z$^3$ is not R$^{15}$—, R$^{15}$—C(O)—, R$^{15}$—N(R$^2$)—, R$^{15}$—O—, R$^{15}$—S—, R$^{15}$—S(O)$_{1-2}$, R$^{15}$—C(O)—O—, R$^{15}$—O—C(O)—, R$^{15}$—C(O)—N(R$^2$)—, R$^{15}$—N(R$^2$)—C(O)—, R$^{15}$—O—C(O)—N(R$^2$)—, R$^{15}$—N(R$^2$)—C(O)—O—, R$^{15}$—S(O)$_2$—N(R$^2$)— or R$^{15}$—N(R$^2$)—S(O)$_2$—;

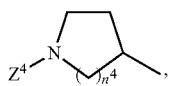

(c) wherein
n$^4$=0, 2, 3 or 4 and
Z$^4$ is selected from the group consisting of R$^{15}$—, R$^{15}$—C(O)—, R$^{13}$—C(S)—, R$^{15}$—N(R$^2$)—, R$^{15}$—O—, R$^{15}$—S—, R$^{15}$—S(O)$_{1-2}$, R$^{15}$—C(O)—O—, R$^{15}$—O—C(O)—, R$^{15}$—C(O)—S—, R$^{15}$—S—C(O)—, R$^{15}$—C(O)—N(R$^2$)—, R$^{15}$—N(R$^2$)—C(O)—, R$^{15}$—C(S)—O—, R$^{15}$—O—C(S)—, R$^{15}$—C(S)—S—, R$^{15}$—S—C(S)—, R$^{15}$—C(S)—N(R$^2$)—, R$^{15}$—N(R$^2$)—C(S)—, R$^{15}$—O—C(O)—O—, R$^{15}$—O—C(O)—S—, R$^{15}$—S—C(O)—O—, R$^{15}$—O—C(O)—N(R$^2$)—, R$^{15}$—N(R$^2$)—C(O)—O—, R$^{15}$—O—C(S)—O—, R$^{15}$—O—C(S)—S—, R$^{15}$—S—C(S)—O—, R$^{15}$—O—C(S)—N(R$^2$)—, R$^{15}$—N(R$^2$)—C(S)—O—, R$^{15}$—S—C(O)—S—, R$^{15}$—S—C(O)—N(R$^2$)—, R$^{15}$—N(R$^2$)—C(O)—S—, R$^{15}$—S—C(S)—S—, R$^{15}$—N(R$^2$)—C(O)—N(R$^2$)—, R$^{15}$—N(R$^2$)—C(S)—N(R$^2$)—, R$^{15}$—N(R$^2$)—C(S)—S—, R$^{15}$—S—C(S)—N(R$^2$)—, R$^{15}$—NH—C(N(R$^2$))—NH—, R$^{15}$—S(O)$_{0-2}$—N(R$^2$)—, R$^{15}$—N(R$^2$)—S(O)$_{0-2}$— and R$^{15}$—N(R$^2$)—S(O)$_{0-2}$—N(R$^2$)—, with the proviso that if n$^4$ is 2 and A is phenyl, then Z$^4$ is not R$^{15}$—, R$^{15}$—C(O)—, R$^{15}$—N(R$^2$)—, R$^{15}$—O—, R$^{15}$—S—, R$^{15}$—S(O)$_{1-2}$, R$^{15}$—C(O)—O—, R$^{15}$—O—C(O)—, R$^{15}$—C(O)—N(R$^2$)—, R$^{15}$—N(R$^2$)—C(O)—, R$^{15}$—O—C(O)—N(R$^2$)—, R$^{15}$—N(R$^2$)—C(O)—O—, R$^{15}$—S(O)$_2$—N(R$^2$)— or R$^{15}$—N(R$^2$)—S(O)$_2$—;

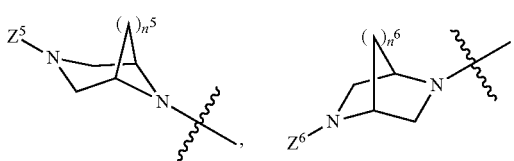

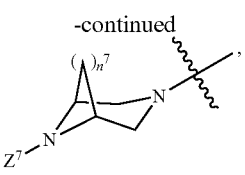

(d) wherein
n$^5$=1-4,
n$^6$=1-4,
n$^7$=1-4,
Z$^5$ is selected from the group consisting of R$^{15}$—, R$^{15}$—C(O)—, R$^{13}$—C(S)—, R$^{15}$—N(R$^2$)—, R$^{15}$—O—, R$^{15}$—S—, R$^{15}$—S(O)$_{1-2}$, R$^{15}$—C(O)—O—, R$^{15}$—O—C(O)—, R$^{15}$—C(O)—S—, R$^{15}$—S—C(O)—, R$^{15}$—C(O)—N(R$^2$)—, R$^{15}$—N(R$^2$)—C(O)—, R$^{15}$—C(S)—O—, R$^{15}$—O—C(S)—, R$^{15}$—C(S)—S—, R$^{15}$—S—C(S)—, R$^{15}$—C(S)—N(R$^2$)—, R$^{15}$—N(R$^2$)—C(S)—, R$^{15}$—O—C(O)—O—, R$^{15}$—O—C(O)—S—, R$^{15}$—S—C(O)—O—, R$^{15}$—O—C(O)—N(R$^2$)—, R$^{15}$—N(R$^2$)—C(O)—O—, R$^{15}$—O—C(S)—O—, R$^{15}$—O—C(S)—S—, R$^{15}$—S—C(S)—O—, R$^{15}$—O—C(S)—N(R$^2$)—, R$^{15}$—N(R$^2$)—C(S)—O—, R$^{15}$—S—C(O)—S—, R$^{15}$—S—C(O)—N(R$^2$)—, R$^{15}$—N(R$^2$)—C(O)—S—, R$^{15}$—S—C(S)—S—, R$^{15}$—N(R$^2$)—C(O)—N(R$^2$)—, R$^{15}$—N(R$^2$)—C(S)—N(R$^2$)—, R$^{15}$—N(R$^2$)—C(S)—S—, R$^{15}$—S—C(S)—N(R$^2$)—, R$^{15}$—NH—C(N(R$^2$))—NH—, R$^{15}$—S(O)$_{0-2}$—N(R$^2$)—, R$^{15}$—N(R$^2$)—S(O)$_{0-2}$— and R$^{15}$—N(R$^2$)—S(O)$_{0-2}$—N(R$^2$)—;

Z$^6$ is selected from the group consisting of R$^{15}$—, R$^{15}$—C(O)—, R$^{13}$—C(S)—, R$^{15}$—N(R$^2$)—, R$^{15}$—O—, R$^{15}$—S—, R$^{15}$—S(O)$_{1-2}$, R$^{15}$—C(O)—O—, R$^{15}$—O—C(O)—, R$^{15}$—C(O)—S—, R$^{15}$—S—C(O)—, R$^{15}$—C(O)—N(R$^2$)—, R$^{15}$—N(R$^2$)—C(O)—, R$^{15}$—C(S)—O—, R$^{15}$—O—C(S)—, R$^{15}$—C(S)—S—, R$^{15}$—S—C(S)—, R$^{15}$—C(S)—N(R$^2$)—, R$^{15}$—N(R$^2$)—C(S)—, R$^{15}$—O—C(O)—O—, R$^{15}$—O—C(O)—S—, R$^{15}$—S—C(O)—O—, R$^{15}$—O—C(O)—N(R$^2$)—, R$^{15}$—N(R$^2$)—C(O)—O—, R$^{15}$—O—C(S)—O—, R$^{15}$—O—C(S)—S—, R$^{15}$—S—C(S)—O—, R$^{15}$—O—C(S)—N(R$^2$)—, R$^{15}$—N(R$^2$)—C(S)—O—, R$^{15}$—S—C(O)—S—, R$^{15}$—S—C(O)—N(R$^2$)—, R$^{15}$—N(R$^2$)—C(O)—S—, R$^{15}$—S—C(S)—S—, R$^{15}$—N(R$^2$)—C(O)—N(R$^2$)—, R$^{15}$—N(R$^2$)—C(S)—N(R$^2$)—, R$^{15}$—N(R$^2$)—C(S)—S—, R$^{15}$—S—C(S)—N(R$^2$)—, R$^{15}$—NH—C(N(R$^2$))—NH—, R$^{15}$—S(O)$_{0-2}$—N(R$^2$)—, R$^{15}$—N(R$^2$)—S(O)$_{0-2}$— and R$^{15}$—N(R$^2$)—S(O)$_{0-2}$—N(R$^2$)—; and Z$^7$ is selected from the group consisting of R$^{15}$—, R$^{15}$—C(O)—, R$^{13}$—C(S)—, R$^{15}$—N(R$^2$)—, R$^{15}$—O—, R$^{15}$—S—, R$^{15}$—S(O)$_{1-2}$, R$^{15}$—C(O)—O—, R$^{15}$—O—C(O)—, R$^{15}$—C(O)—S—, R$^{15}$—S—C(O)—, R$^{15}$—C(O)—N(R$^2$)—, R$^{15}$—N(R$^2$)—C(O)—, R$^{15}$—C(S)—O—, R$^{15}$—O—C(S)—, R$^{15}$—C(S)—S—, R$^{15}$—S—C(S)—, R$^{15}$—C(S)—N(R$^2$)—, R$^{15}$—N(R$^2$)—C(S)—, R$^{15}$—O—C(O)—O—, R$^{15}$—O—C(O)—S—, R$^{15}$—S—C(O)—O—, R$^{15}$—O—C(O)—N(R$^2$)—, R$^{15}$—N(R$^2$)—C(O)—O—, R$^{15}$—O—C(S)—O—, R$^{15}$—O—C(S)—S—, R$^{15}$—S—C(S)—O—, R$^{15}$—O—C(S)—N(R$^2$)—, R$^{15}$—N(R$^2$)—C(S)—O—, R$^{15}$—S—C(O)—S—, R$^{15}$—S—C(O)—N(R$^2$)—, R$^{15}$—N(R$^2$)—C(O)—S—, R$^{15}$—S—C(S)—S—, R$^{15}$—N(R$^2$)—C(O)—N(R$^2$)—, R$^{15}$—N(R$^2$)—C(S)—N(R$^2$)—, R$^{15}$—N(R$^2$)—C(S)—S—, R$^{15}$—S—C(S)—N(R$^2$)—, R$^{15}$—NH—C $(N(R^2))$—NH—, $R^{15}$—$S(O)_{0-2}$—$N(R^2)$—, $R^{15}$—$N(R^2)$—$S(O)_{0-2}$— and $R^{15}$—$N(R^2)$—$S(O)_{0-2}$—$N(R^2)$—; or (f)

$$Z^8-N\underset{}{\overset{}{\bigcirc}}N-\xi$$

(e) wherein $Z^8$ is selected from the group consisting of $R^{15}$—, $R^{15}$—C(O)—, $R^{13}$—C(S)—, $R^{15}$—$N(R^2)$—, $R^{15}$—O—, $R^{15}$—S—, $R^{15}$—$S(O)_{1-2}$, $R^{15}$—C(O)—O—, $R^{15}$—O—C(O)—, $R^{15}$—C(O)—S—, $R^{15}$—S—C(O)—, $R^{15}$—C(O)—$N(R^2)$—, $R^{15}$—$N(R^2)$—C(O)—, $R^{15}$—C(S)—O—, $R^{15}$—O—C(S)—, $R^{15}$—C(S)—S—, $R^{15}$—S—C(S)—, $R^{15}$—C(S)—$N(R^2)$—, $R^{15}$—$N(R^2)$—C(S)—, $R^{15}$—O—C(O)—O—, $R^{15}$—O—C(O)—S—, $R^{15}$—S—C(O)—O—, $R^{15}$—O—C(O)—$N(R^2)$—, $R^{15}$—$N(R^2)$—C(O)—O—, $R^{15}$—O—C(S)—O—, $R^{15}$—O—C(S)—S—, $R^{15}$—S—C(S)—O—, $R^{15}$—O—C(S)—$N(R^2)$—, $R^{15}$—$N(R^2)$—C(S)—O—, $R^{15}$—S—C(O)—S—, $R^{15}$—S—C(O)—$N(R^2)$—, $R^{15}$—$N(R^2)$—C(O)—S—, $R^{15}$—S—C(S)—S—, $R^{15}$—$N(R^2)$—C(O)—$N(R^2)$—, $R^{15}$—$N(R^2)$—C(S)—$N(R^2)$—, $R^{15}$—$N(R^2)$—C(S)—S—, $R^{15}$—S—C(S)—$N(R^2)$—, $R^{15}$—NH—$C(N(R^2))$—NH—, $R^{15}$—$S(O)_{0-2}$—$N(R^2)$—, $R^{15}$—$N(R^2)$—$S(O)_{0-2}$— and $R^{15}$—$N(R^2)$—$S(O)_{0-2}$—$N(R^2)$—, with the proviso that if A is phenyl, then $Z^8$ is not $R^{15}$—, $R^{15}$—C(O)—, $R^{15}$—$N(R^2)$—, $R^{15}$—O—, $R^{15}$—S—, $R^{15}$—$S(O)_{1-2}$, $R^{15}$—C(O)—O—, $R^{15}$—O—C(O)—, $R^{15}$—C(O)—$N(R^2)$—, $R^{15}$—$N(R^2)$—C(O)—, $R^{15}$—O—C(O)—$N(R^2)$—, $R^{15}$—$N(R^2)$—C(O)—O—, $R^{15}$—$S(O)_2$—$N(R^2)$— or $R^{15}$—$N(R^2)$—$S(O)_2$—, in which each $R^2$ is independently selected from the group consisting of hydrogen, ($C_1$-$C_5$ alkyl)-, Ar—($C_0$-$C_4$ alkyl)-, Het-($C_0$-$C_4$ alkyl)-, Hca-($C_0$-$C_4$ alkyl)-, Cak-($C_0$-$C_4$ alkyl)-, $R^{14}$—CO—, $R^{14}$—SO2—, $R^{14}$—CO—NH— and $R^{14}$—CO—O—, in which each alkyl is optionally substituted;

each $R^5$ is independently selected from the group consisting of H—, optionally substituted ($C_1$-$C_6$ hydrocarbyl)-, Ar—($C_1$-$C_6$ hydrocarbyl)-, Het-($C_1$-$C_6$ hydrocarbyl)-, Hca-($C_0$-$C_6$ hydrocarbyl)- and Cak-($C_0$-$C_6$ hydrocarbyl)-;

each $R^6$ is independently selected from the group consisting of H—, substituted ($C_1$-$C_6$ hydrocarbyl)- with the proviso that if the ($C_1$-$C_6$ hydrocarbyl) has only one substituent, it is not halo or amino, Hca-($C_0$-$C_1$ or $C_3$-$C_6$ hydrocarbyl)- and Cak-($C_0$-$C_6$ hydrocarbyl)-;

each $R^7$ is independently selected from the group consisting of H, optionally substituted ($C_1$-$C_6$ hydrocarbyl)-, Hca-($C_0$-$C_1$ or $C_3$-$C_6$ hydrocarbyl)- and Cak-($C_0$-$C_6$ hydrocarbyl)-;

each $R^8$ is independently selected from the group consisting of optionally substituted ($C_1$-$C_6$ hydrocarbyl)-, Ar—($C_1$-$C_6$ hydrocarbyl)-, Het-($C_1$-$C_6$ hydrocarbyl)-, Hca-($C_0$-$C_6$ hydrocarbyl)-, Cak-($C_0$-$C_6$ hydrocarbyl)-, with the proviso that $R^8$ is not 2(morpholin-4-yl)ethyl;

each $R^9$ is independently selected from the group consisting of Hca-($C_0$-$C_6$ hydrocarbyl)- and Cak-($C_0$-$C_6$ hydrocarbyl)-;

each $R^{10}$ is independently selected from the group consisting of H—, Hca-($C_0$-$C_6$ hydrocarbyl)- and Cak-($C_0$-$C_6$ hydrocarbyl)-;

each $R^{11}$ is independently selected from the group consisting of H—, ($C_1$-$C_6$ hydrocarbyl)-, Hca-($C_0$-$C_6$ hydrocarbyl)- and Cak-($C_0$-$C_6$ hydrocarbyl)-;

each $R^{12}$ is independently selected from the group consisting of optionally substituted ($C_1$-$C_6$ hydrocarbyl)-, Ar—($C_1$-$C_6$ hydrocarbyl)-, Het-($C_1$-$C_6$ hydrocarbyl)-, Hca-($C_0$-$C_6$ hydrocarbyl)-, Cak-($C_0$-$C_6$ hydrocarbyl)-;

each $R^{13}$ is independently selected from the group consisting of H—, optionally substituted ($C_1$-$C_6$ hydrocarbyl)-, Hca-($C_0$-$C_6$ hydrocarbyl)- and Cak-($C_0$-$C_6$ hydrocarbyl)-;

each $R^{14}$ is independently selected from the group consisting of Ar—and optionally substituted ($C_1$-$C_6$ hydrocarbyl)-; and each $R^{15}$ is independently selected from the group consisting of H—, optionally substituted ($C_1$-$C_6$ hydrocarbyl)-, Ar—($C_0$-$C_6$ hydrocarbyl)-, Het-($C_0$-$C_6$ hydrocarbyl)-, Hca-($C_0$-$C_6$ hydrocarbyl)- and Cak-($C_0$-$C_6$ hydrocarbyl)-;

in which any ($C_1$-$C_6$ hydrocarbyl)- moiety is optionally substituted, and each Ar is independently an optionally substituted aryl, each Het is independently an optionally substituted heteroaryl, each Hca is independently an optionally substituted heterocycloalkyl, and each Cak is independently an optionally substituted cycloalkyl.

2. The compound according to claim 1, wherein T is $NH_2$.

3. The compound according to claim 1, wherein A is unsubstituted or optionally-substituted phenyl.

4. The compound according to claim 1, wherein A is a 6-membered ring and the X— and carbonyl moieties are arranged in a 1,4-manner relative to one another on the ring.

5. The compound according to claim 1, wherein A is unsubstituted arylene.

6. The compound according to claim 1, wherein A is unsubstituted phenylene.

7. The compound according to claim 1, wherein X is $$Z^2\underset{}{\overset{}{\bigcirc}}_{n^2}N-,$$

wherein $n^2$=0 or 2-4 and $Z^2$ is selected from the group consisting of $R^{15}$—, $R^{15}$—C(O)—, $R^{13}$—C(S)—, $R^{15}$—$N(R^2)$—, $R^{15}$—O—, $R^{15}$—S—, $R^{15}$—$S(O)_{1-2}$, $R^{15}$—C(O)—O—, $R^{15}$—O—C(O)—, $R^{15}$—C(O)—S—, $R^{15}$—S—C(O)—, $R^{15}$—C(O)—$N(R^2)$—, $R^{15}$—$N(R^2)$—C(O)—, $R^{15}$—C(S)—O—, $R^{15}$—O—C(S)—, $R^{15}$—C(S)—S—, $R^{15}$—S—C(S)—, $R^{15}$—C(S)—$N(R^2)$—, $R^{15}$—$N(R^2)$—C(S)—, $R^{15}$—O—C(O)—O—, $R^{15}$—O—C(O)—S—, $R^{15}$—S—C(O)—O—, $R^{15}$—O—C(O)—$N(R^2)$—, $R^{15}$—$N(R^2)$—C(O)—O—, $R^{15}$—O—C(S)—O—, $R^{15}$—O—C(S)—S—, $R^{15}$—S—C(S)—O—, $R^{15}$—O—C(S)—$N(R^2)$—, $R^{15}$—$N(R^2)$—C(S)—O—, $R^{15}$—S—C(O)—S—, $R^{15}$—S—C(O)—$N(R^2)$—, $R^{15}$—$N(R^2)$—C(O)—S—, $R^{15}$—S—C(S)—S—, $R^{15}$—$N(R^2)$—C(O)—$N(R^2)$—, $R^{15}$—$N(R^2)$—C(S)—$N(R^2)$—, $R^{15}$—$N(R^2)$—C(S)—S—, $R^{15}$—S—C(S)—$N(R^2)$—, $R^{15}$—NH—$C(N(R^2))$—NH—, $R^{15}$—$S(O)_{0-2}$—$N(R^2)$—, $R^{15}$—$N(R^2)$—$S(O)_{0-2}$— and $R^{15}$—$N(R^2)$—$S(O)_{0-2}$—$N(R^2)$—.

8. The compound according to claim 1, wherein X is

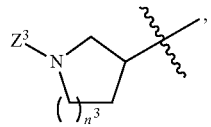

wherein
$n^3$=0-4 and
$Z^3$ is selected from the group consisting of $R^{15}$—, $R^{15}$—C(O)—, $R^{13}$—C(S)—, $R^{15}$—N($R^2$)—, $R^{15}$—O—, $R^{15}$—S—, $R^{15}$—S(O)$_{1\text{-}2}$, $R^{15}$—C(O)—O—, $R^{15}$—O—C(O)—, $R^{15}$—C(O)—S—, $R^{15}$—S—C(O)—, $R^{15}$—C(O)—N($R^2$)—, $R^{15}$—N($R^2$)—C(O)—, $R^{15}$—C(S)—O—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^{15}$—O—C(O)—O—, $R^{15}$—O—C(O)—S—, $R^{15}$—S—C(O)—O—, $R^{15}$—O—C(O)—N($R^2$)—, $R^{15}$—N($R^2$)—C(O)—O—, $R^{15}$—O—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0\text{-}2}$—N($R^2$)—, $R^{15}$—N($R^2$)—S(O)$_{0\text{-}2}$— and $R^{15}$—N($R^2$)—S(O)$_{0\text{-}2}$—N($R^2$)—, with the proviso that if $n^3$ is 2 and A is phenyl, then $Z^3$ is not $R^{15}$—, $R^{15}$—C(O)—, $R^{15}$—N($R^2$)—, $R^{15}$—O—, $R^{15}$—S—, $R^{15}$—S(O)$_{1\text{-}2}$, $R^{15}$—C(O)—O—, $R^{15}$—O—C(O)—, $R^{15}$—C(O)—N($R^2$)—, $R^{15}$—N($R^2$)—C(O)—, $R^{15}$—O—C(O)—N($R^2$)—, $R^{15}$—N($R^2$)—C(O)—O—, $R^{15}$—S(O)$_2$—N($R^2$)— or $R^{15}$—N($R^2$)—S(O)$_2$—.

9. The compound claim 1, wherein X is

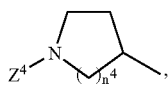

wherein
$n^4$=0 or 2-4 and
$Z^4$ is selected from the group consisting of $R^{15}$—, $R^{15}$—C(O)—, $R^{13}$—C(S)—, $R^{15}$—N($R^2$)—, $R^{15}$—O—, $R^{15}$—S—, $R^{15}$—S(O)$_{1\text{-}2}$, $R^{15}$—C(O)—O—, $R^{15}$—O—C(O)—, $R^{15}$—C(O)—S—, $R^{15}$—S—C(O)—, $R^{15}$—C(O)—N($R^2$)—, $R^{15}$—N($R^2$)—C(O)—, $R^{15}$—C(S)—O—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^{15}$—O—C(O)—O—, $R^{15}$—O—C(O)—S—, $R^{15}$—S—C(O)—O—, $R^{15}$—O—C(O)—N($R^2$)—, $R^{15}$—N($R^2$)—C(O)—O—, $R^{15}$—O—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0\text{-}2}$—N($R^2$)—, $R^{15}$—N(R)—S(O)$_{0\text{-}2}$— and $R^{15}$—N($R^2$)—S(O)$_{0\text{-}2}$—N($R^2$)—, with the proviso that if $n^4$ is 2 and A is phenyl, then $Z^4$ is not $R^{15}$—, $R^{15}$—C(O)—, $R^{15}$—N($R^2$)—, $R^{15}$—O—, $R^{15}$—S—, $R^{15}$—S(O)$_{1\text{-}2}$, $R^{15}$—C(O)—O—, $R^{15}$—O—C(O)—, $R^{15}$—C(O)—N($R^2$)—, $R^{15}$—N($R^2$)—C(O)—, $R^{15}$—O—C(O)—N($R^2$)—, $R^{15}$—N($R^2$)—C(O)—O—, $R^{15}$—S(O)$_2$—N($R^2$)— or $R^{15}$—N($R^2$)—S(O)$_2$—.

10. The compound according to claim 1, wherein X is

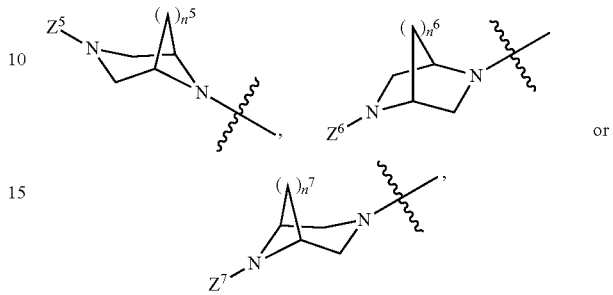

wherein
$n^5$=1-4,
$n^6$=1-4,
$n^7$=1-4,
$Z^5$ is selected from the group consisting of $R^{15}$—, $R^{15}$—C(O)—, $R^{13}$—C(S)—, $R^{15}$—N($R^2$)—, $R^{15}$—O—, $R^{15}$—S—, $R^{15}$—S(O)$_{1\text{-}2}$, $R^{15}$—C(O)—O—, $R^{15}$—O—C(O)—, $R^{15}$—C(O)—S—, $R^{15}$—S—C(O)—, $R^{15}$—C(O)—N($R^2$)—, $R^{15}$—N($R^2$)—C(O)—, $R^{15}$—C(S)—O—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^{15}$—O—C(O)—O—, $R^{15}$—O—C(O)—S—, $R^{15}$—S—C(O)—O—, $R^{15}$—O—C(O)—N($R^2$)—, $R^{15}$—N($R^2$)—C(O)—O—, $R^{15}$—O—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0\text{-}2}$—N($R^2$)—, $R^{15}$—N(R)—S(O)$_{0\text{-}2}$— and $R^{15}$—N($R^2$)—S(O)$_{0\text{-}2}$—N($R^2$)—;

$Z^6$ is selected from the group consisting of $R^{15}$—, $R^{15}$—C(O)—, $R^{13}$—C(S)—, $R^{15}$—N($R^2$)—, $R^{15}$—O—, $R^{15}$—S—, $R^{15}$—S(O)$_{1\text{-}2}$, $R^{15}$—C(O)—O—, $R^{15}$—O—C(O)—, $R^{15}$—C(O)—S—, $R^{15}$—S—C(O)—, $R^{15}$—C(O)—N($R^2$)—, $R^{15}$—N($R^2$)—C(O)—, $R^{15}$—C(S)—O—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^{15}$—O—C(O)—O—, $R^{15}$—O—C(O)—S—, $R^{15}$—S—C(O)—O—, $R^{15}$—O—C(O)—N($R^2$)—, $R^{15}$—N($R^2$)—C(O)—O—, $R^{15}$—O—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0\text{-}2}$—N($R^2$)—, $R^{15}$—N(R)—S(O)$_{0\text{-}2}$— and $R^{15}$—N($R^2$)—S(O)$_{0\text{-}2}$—N($R^2$)—; and $Z^7$ is selected from the group consisting of $R^{15}$—, $R^{15}$—C(O)—, $R^{13}$—C(S)—, $R^{15}$—N($R^2$)—, $R^{15}$—O—, $R^{15}$—S—, $R^{15}$—S(O)$_{1\text{-}2}$, $R^{15}$—C(O)—O—, $R^{15}$—O—C(O)—, $R^{15}$—C(O)—S—, $R^{15}$—S—C(O)—, $R^{15}$—C(O)—N($R^2$)—, $R^{15}$—N($R^2$)—C(O)—, $R^{15}$—C(S)—O—, $R^{15}$—O—C(S)—, $R^{15}$—C(S)—S—, $R^{15}$—S—C (S)—, $R^{15}$—C(S)—N($R^2$)—, $R^{15}$—N($R^2$)—C(S)—, $R^{15}$—O—C(O)—O—, $R^{15}$—O—C(O)—S—, $R^{15}$—S—C(O)—O—, $R^{15}$—O—C(O)—N($R^2$)—, $R^{15}$—N($R^2$)—C(O)—O—, $R^{15}$—O—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0-2}$—N($R^2$)—, $R^{15}$—N($R^2$)—S(O)$_{12}$— and $R^{15}$—N($R^2$)—S(O)$_{0-2}$—N($R^2$)—.

11. The compound according to claim 1, wherein X is

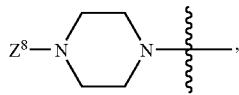

wherein
$Z^8$ is selected from the group consisting of $R^{15}$—, $R^{15}$—C(O)—, $R^{13}$—C(S)—, $R^{15}$—N($R^2$)—, $R^{15}$—O—, $R^{15}$—S—, $R^{15}$—S(O)$_{1-2}$, $R^{15}$—C(O)—O—, $R^{15}$—O—C(O)—, $R^{15}$—C(O)—S—, $R^{15}$—S—C(O)—, $R^{15}$—C(O)—N($R^2$)—, $R^{15}$—N($R^2$)—C(O)—, $R^{15}$—C(S)—O—, $R^{15}$—O—C(S)—, $R^{15}$—C(S)—S—, $R^{15}$—S—C(S)—, $R^{15}$—C(S)—N($R^2$)—, $R^{15}$—N($R^2$)—C(S)—, $R^{15}$—O—C(O)—O—, $R^{15}$—O—C(O)—S—, $R^{15}$—S—C(O)—O—, $R^{15}$—O—C(O)—N($R^2$)—, $R^{15}$—N($R^2$)—C(O)—O—, $R^{15}$—O—C(S)—O—, $R^{15}$—O—C(S)—S—, $R^{15}$—S—C(S)—O—, $R^{15}$—O—C(S)—N($R^2$)—, $R^{15}$—N($R^2$)—C(S)—O—, $R^{15}$—S—C(O)—S—, $R^{15}$—S—C(O)—N($R^2$)—, $R^{15}$—N($R^2$)—C(O)—S—, $R^{15}$—S—C(S)—S—, $R^{15}$—N($R^2$)—C(O)—N($R^2$)—, $R^{15}$—N($R^2$)—C(S)—N($R^2$)—, $R^{15}$—N($R^2$)—C(S)—S—, $R^{15}$—S—C(S)—N($R^2$)—, $R^{15}$—NH—C(N($R^2$))—NH—, $R^{15}$—S(O)$_{0-2}$—N($R^2$)—, $R^{15}$—N($R^2$)—S(O)$_{0-2}$— and $R^{15}$—N($R^2$)—S(O)$_{0-2}$—N($R^2$)—, with the proviso that if A is phenyl, then $Z^8$ is not $R^{15}$—, $R^{15}$—C(O)—, $R^{15}$—N($R^2$)—, $R^{15}$—O—, $R^{15}$—S—, $R^{15}$—S(O)$_{1-2}$, $R^{15}$—C(O)—O—, $R^{15}$—O—C(O)—, $R^{15}$—C(O)—N($R^2$)—, $R^{15}$—N($R^2$)—C(O)—, $R^{15}$—O—C(O)—N($R^2$)—, $R^{15}$—N($R^2$)—C(O)—O—, $R^{15}$—S(O)$_2$—N($R^2$)— or $R^{15}$—N($R^2$)—S(O)$_2$—.

12. A composition comprising a compound according to claim 1 present in at least about 30% enantiomeric or diastereomeric excess.

13. The composition according to claim 12 wherein the compound is present in at least about 50% enantiomeric or diastereomeric excess.

14. The composition according to claim 12 wherein the compound is present in at least 80% enantiomeric or diastereomeric excess.

15. The composition according to claim 12 wherein the compound is present in at least 90% enantiomeric or diastereomeric excess.

16. A composition comprising a compound according to claim 1 present as a substantially racemic mixture.

17. A pharmaceutical composition comprising a compound according to claim 1, and a pharmaceutically acceptable, diluent, carrier or excipient.

\* \* \* \* \*